(12) United States Patent
Yegnasubramanian et al.

(10) Patent No.: US 10,196,698 B2
(45) Date of Patent: Feb. 5, 2019

(54) DNA METHYLATION MARKERS FOR METASTATIC PROSTATE CANCER

(71) Applicant: THE JOHNS HOPKINS UNIVERSITY, Baltimore, MD (US)

(72) Inventors: Srinivasan Yegnasubramanian, Ellicott City, MD (US); G. Steven Bova, Baltimore, MD (US); Martin Aryee, Baltimore, MD (US); William B. Isaacs, Glyndon, MD (US); William G. Nelson, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/598,684

(22) Filed: May 18, 2017

(65) Prior Publication Data
US 2018/0100196 A1 Apr. 12, 2018

Related U.S. Application Data

(63) Continuation of application No. 14/162,180, filed on Jan. 23, 2014.

(60) Provisional application No. 61/755,688, filed on Jan. 23, 2013.

(51) Int. Cl.
*C12Q 1/6855* (2018.01)
*C12Q 1/6886* (2018.01)

(52) U.S. Cl.
CPC ......... *C12Q 1/6886* (2013.01); *C12Q 1/6855* (2013.01); *C12Q 2600/154* (2013.01)

(58) Field of Classification Search
None
See application file for complete search history.

(56) References Cited

U.S. PATENT DOCUMENTS

| | | |
|---|---|---|
| 2005/0181375 A1 | 8/2005 | Aziz |
| 2009/0005268 A1 | 1/2009 | Berlin |
| 2009/0305257 A1 | 12/2009 | Guyon |
| 2010/0297641 A1 | 11/2010 | Markl et al. |
| 2010/0303795 A1* | 12/2010 | Sorensen ............ A61K 31/192 424/94.6 |
| 2011/0217706 A1 | 9/2011 | Maloney et al. |
| 2013/0022974 A1* | 1/2013 | Chinnaiyan .......... C12Q 1/6886 435/6.11 |

FOREIGN PATENT DOCUMENTS

| | | |
|---|---|---|
| WO | 2003044232 A1 | 5/2003 |
| WO | 2004063355 A2 | 7/2004 |
| WO | 2007009755 A2 | 1/2007 |
| WO | 2007116417 A1 | 10/2007 |
| WO | 2008110006 A1 | 9/2008 |

OTHER PUBLICATIONS

Sandoval et al. (2011) Validation of a DNA methylation microarray for 450,000 CpG sites in the human genome. Epigenetics, 6(6): 692-702 (Year: 2011).*
Illumina HumanMethylation27 content list (obtained from: <https://support.illumina.com/array/array_kits/infinium_humanmethylation27_beadchip_kit/downloads.html> on Feb. 14, 2018, 2 pages).*
Illumina HumanMethylation450 content list (obtained from: https://support.illumina.com/array/array_kits/infinium_humanmethylation450_beadchip_kit/downloads.html on Feb. 14, 2018, 9 pages).*
Phe et al. (2009) BJU International, 105:1364-1370 (Year: 2009).*
Wang et al. (2005) Neoplasia, 7(8):748-760 (Year: 2005).*
Kumar et al. (2012) Cancers, 4:1252-1299 (Year: 2012).*
Prakash et al (2002) Symptomatic and asymptomatic benign prostatic hyperplasia: molecular differentiation by using microarrays. Proc Natl Arad Sci U S A. May 28, 2002;99(11):7598-603.
Dunn et al (2006) A novel role of myosin VI in human prostate cancer. Am J Pathol. Nov. 2006;169(5):1843-54.
Gentleman et al (2004) Bioconductor: open software development for computational biology and bioinformatics. Genome Biol. 2004;5(10):R80. Epub Sep. 15, 2004.
Kobayashi et al (2011) DNA methylation profiling reveals novel biomarkers and important roles for DNA methyltransferases in prostate cancer. Genome Res. Jul. 2011;21(7):1017-27. doi: 10.1101/gr.119487.110. Epub Apr. 26, 2011.
Aryee et al (2013) DNA methylation alterations exhibit intraindividual stability and interindividual heterogeneity in prostate cancer metastases. Sci Transl Med. Jan. 23, 2013;5(169):169ra10. doi: 10.1126/scitranslmed.3005211.
Laird et al (2003) The power and the promise of DNA methylation markers. Nat Rev Cancer. Apr. 2003;3(4):253-66.
Mahapatra et al (2012) Global methylation profiling for risk prediction of prostate cancer. Clin Cancer Res. May 15, 2012;18(10):2882-95. doi: 10.1158/1078-0432.CCR-11-2090.
Kim et al (2011) Deep sequencing reveals distinct patterns of DNA methylation in prostate cancer. Genome Res. Jul. 2011;21(7):1028-41. doi: 10.1101/gr.119347.110.
Maxwell et al (2009) Recent Advances in the Detection of Prostate Cancer using Epigenetic markers in Commonly Collected Laboratory Samples. LabMedicine 40:171-178.

(Continued)

*Primary Examiner* — Neil P Hammell
(74) *Attorney, Agent, or Firm* — Johns Hopkins Technology Ventures

(57) ABSTRACT

The present invention relates to the field of cancer. More specifically, the present invention provides methods and compositions useful for assessing prostate cancer. In a specific embodiment, present inventors have developed and applied a new technology and associated computation methods enabling simultaneous genome-scale analysis of genetic (copy number) and epigenetic (total methylation (TM) and allele-specific methylation (ASM) alternation, This method, called MBD-SNP, features affinity enrichment or methylated genomic DNA fragments using a methyl-binding domain polypeptide.

1 Claim, 37 Drawing Sheets

(56) References Cited

OTHER PUBLICATIONS

Perry et al (2006) The emerging roles of DNA methylation in the clinical management of prostate cancer. Endocr Relat Cancer. Jun. 2006;13(2):357-77.
Bert et al (2012) Regional activation of the cancer genome by long-range epigenetic remodeling. Cancer Cell. Jan. 14, 2013;23(1):9-22. doi: 10.1016/j.ccr.2012.11.006. Epub Dec. 13, 2012.
Hanahan et al (2011) Hallmarks of cancer: the next generation. Cell. Mar. 4, 2011;144(5):646-74. doi: 10.1016/j.cell.2011.02.013.
Jones et al (2007) The epigenomics of cancer. Cell. Feb. 23, 2007;128(4):683-92.
Probst et al (2009) Epigenetic inheritance during the cell cycle. Nat Rev Mol Cell Biol. Mar. 2009;10(3):192-206. doi: 10.1038/nrm2640.
Feinberg et al (2010) Personalized epigenomic signatures that are stable over time and covary with body mass index. Sci Transl Med. Sep. 15, 2010;2(49):49ra67. doi: 10.1126/scitranslmed.3001262.
Hemberger et al (2009) Epigenetic dynamics of stem cells and cell lineage commitment: digging Waddington's canal. Nat Rev Mol Cell Biol. Aug. 2009;10(8):526-37. doi: 10.1038/nrm2727. Epub Jul. 15, 2009.
Kangaspeska et al (2008) Transient cyclical methylation of promoter DNA. Nature. Mar. 6, 2008;452(7183):112-5. doi: 10.1038/nature06640.
Metivier et al (2008) Cyclical DNA methylation of a transcriptionally active promoter. Nature. Mar. 6, 2008;452(7183):45-50. doi: 10.1038/nature06544.
Rainier et al (1994) Genomic imprinting, DNA methylation, and cancer. J Natl Cancer Inst. May 18, 1994;86(10):753-9.
Li et al (1993) Role for DNA methylation in genomic imprinting. Nature. Nov. 25, 1993;366(6453):362-5.
Tycko et al (2010) Allele-specific DNA methylation: beyond imprinting. Hum Mol Genet. Oct. 15, 2010;19(R2):R210-20. doi: 10.1093/hmg/ddq376. Epub Sep. 20, 2010.
Schuebel et al (2007) Comparing the DNA hypermethylome with gene mutations in human colorectal cancer. PLoS Genet. Sep. 2007;3(9):1709-23. Epub Jul. 31, 2007.
Cross et al (1994) Purification of CpG islands using a methylated DNA binding column. Nat Genet. Mar. 1994;6(3):236-44.
Yegnasubramanian et al (2006) Combination of methylated-DNA precipitation and methylation-sensitive restriction anzymes (COMPARE-MS) for the rapid, sensitive and quantitative detection of DNA methylation. Nucleic Acids Res. Feb. 9, 2006;34(3):e19.
Yegnasubramanian et al (2011) Chromosome-wide mapping of DNA methylation patterns in normal and malignant prostate cells reveals pervasive methylation of gene-associated and conserved intergenic sequences. BMC Genomics. Jun. 13, 2011;12:313. doi: 10.1186/1471-2164-12-313.
Liu et al (2009) Copy Number analysis indicates monoclonal origin of lethal metastatic prostate cancer. Nat Med. May 2009;15(5):559-65. doi: 10.1038/nm.1944. Epub Apr. 12, 2009.
Yachida et al (2010) Distant metastasis occurs late during the genetic evolution of pancreatic cancer. Nature. Oct. 28, 2010;467(7319):1114-7. doi: 10.1038/nature09515.
Campbell et al (2010) The patterns and dynamics of genomic instability in metastatic pancreatic cancer. Nature. Oct. 28, 2010;467(7319):1109-13. doi: 10.1038/nature09460.
Yegnasubramanian et al (2004) Hypermethylation of CpG islands in primary and metastatic human prostate cancer. Dancer Res. Mar. 15, 2004;64(6):1975-86.
Feinberg et al (2006) The epigenetic progenitor origin of human cancer. Nat Rev Genet. Jan. 2006;7(1):21-33.
Jarrard et al (1995) Regional loss of imprinting of the insulin-like growth factor II gene occurs in human prostate tissues. Clin Cancer Res. Dec. 1995;1(12):1471-8.
Issa et al (2004) CpG island methylator phenotype in cancer. Nat Rev Cancer. Dec. 2004;4(12):988-93.

Weisenberger et al (2006) CpG island methylator phenotype underlies sporadic microsatellite instability and is tightly associated with BRAF mutation in colorectal cancer. Nat Genet. Jul. 2006;38(7):787-93. Epub Jun. 25, 2006.
Noushmehr et al (2010) Identification of a CpG island methylator phenotype that defines a distinct subgroup of glioma. Dancer Cell. May 18, 2010;17(5):510-22. doi: 10.1016/j.ccr.2010.03.017. Epub Apr. 15, 2010.
Ashburner et al (2000) Gene ontology: tool for the unification of biology. The Gene Ontology Consortium. Nat Genet. May 2000;25(1):25-9.
Taylor et al (2010) Integrative genomic profiling of human prostate cancer. Cancer Cell. Jul. 13, 2010;18(1):11-22. doi: 10.1016/j.ccr.2010.05.026. Epub Jun. 24, 2010.
Yegnasubramanian et al (2008) DNA hypomethylation arises later in prostate cancer progression than CpG island hypermethylation and contributes to metastatic tumor heterogeneity. Cancer Res. Nov. 1, 2008;68(21):8954-67. doi: 10.1158/0008-5472.CAN-07-6088.
Esteller et al (2008) Epigenetics in cancer. N Engl J Med. Mar. 13, 2008;358(11):1148-59. doi: 10.1056/NEJMra072067.
Herman et al (2003) Gene silencing in cancer in association with promoter hypermethylation. N Engl J Med. Nov. 20, 2003;349(21):2042-54.
Feinberg et al (1983) Hypomethylation distinguishes genes of some human cancers from their normal counterparts. Nature. Jan. 6, 1983;301(5895):89-92.
Goelz et al (1985) Hypomethylation of DNA from benign and malignant human colon neoplasms. Science. Apr. 12, 1985;228(4696):187-90.
Gama-Sosa et al (1983) The 5-methylcytosine content of DNA from human tumors. Nucleic Acids Res. Oct. 11, 1983;11(19):6883-94.
Luo et al (2001) Human prostate cancer and benign prostatic hyperplasia: molecular dissection by gene expression profiling. Cancer Res. Jun. 15, 2001;61(12):4683-8.
Luo et al (2002) Alpha-methylacyl-CoA racemase: a new molecular marker for prostate cancer. Cancer Res. Apr. 15, 2002;62(8):2220-6.
Varambally et al (2002) The polycomb group protein EZH2 is involved in progression of prostate cancer. Nature. Oct. 10, 2002;419(6907):624-9.
Lee et al (1994) Cytidine methylation of regulatory sequences near the pi-class glutathione S-transferase gene accompanies human prostatic carcinogenesis. Proc Natl Acad Sci U S A. Nov. 22, 1994;91(24):11733-7.
Anders et al (2009) Visualization of genomic data with the Hilbert curve. Bioinformatics. May 15, 2009;25(10):1231-5. doi: 10.1093/bioinformatics/btp152. Epub Mar. 17, 2009.
Coolen et al (2010) Consolidation of the cancer genome into domains of repressive chromatin by long-range epigenetic silencing (LRES) reduces transcriptional plasticity. Nat Cell Biol. Mar. 2010;12(3):235-46. doi: 10.1038/ncb2023. Epub Feb. 21, 2010.
Hansen et al (2011) Increased methylation variation in epigenetic domains across cancer types. Nat Genet. Jun. 26, 2011;43(8):768-75. doi: 10.1038/ng.865.
Lee et al (2012) Landscape of somatic retrotransposition in human cancers. Science. Aug. 24, 2012;337(6097):967-71. doi: 10.1126/science.1222077. Epub Jun. 28, 2012.
Su et al (1992) Multiple intestinal neoplasia caused by a mutation in the murine homolog of the APC gene. Science. May 1, 1992;256(5057):668-70.
Laird et al (1995) Suppression of intestinal neoplasia by DNA hypomethylation. Cell. Apr. 21, 1995;81(2):197-205.
Eads et al (2002) Complete genetic suppression of polyp formation and reduction of CpG-island hypermethylation in Apc(Min/+) Dnmt1-hypomorphic Mice. Cancer Res. Mar. 1, 2002;62(5):1296-9.
Sansom et al (2003) Deficiency of Mbd2 suppresses intestinal tumorigenesis. Nat Genet. Jun. 2003;34(2):145-7.
Bakin et al (1999) Role of DNA 5-methylcytosine transferase in cell transformation by fos. Science. Jan. 15, 1999;283(5400):387-90.
Peli et al (1999) Oncogenic Ras inhibits Fas ligand-mediated apoptosis by downregulating the expression of Fas. EMBO J. Apr. 1, 1999;18(7):1824-31.
Gazin et al (2007) An elaborate pathway required for Ras-mediated epigenetic silencing. Nature. Oct. 25, 2007;449(7165)1073-7.

(56) References Cited

OTHER PUBLICATIONS

Berger et al (2011) The genomic complexity of primary human prostate cancer. Nature. Feb. 10, 2011;470(7333):214-20. doi: 10.1038/nature09744.
Rubin et al (2011) Common gene rearrangements in prostate cancer. J Clin Oncol. Sep. 20, 2011;29(27):3659-68. doi: 10.1200/JCO.2011.35.1916. Epub Aug. 22, 2011.
Gerlinger et al (2012) Intratumor heterogeneity and branched evolution revealed by multiregion sequencing. N Engl J Med. Mar. 8, 2012;366(10):883-92. doi: 10.1056/NEJMoa1113205.
Serre et al (2010) MBD-isolated Genome Sequencing provides a high-throughput and comprehensive survey of DNA methylation in the human genome. Nucleic Acids Res. Jan. 2010;38(2):391-9. doi: 10.1093/nar/gkp992. Epub Nov. 11, 2009.

* cited by examiner

B    GENERATION OF MBD-SNP VALIDATION CONTROL SPECIMENS

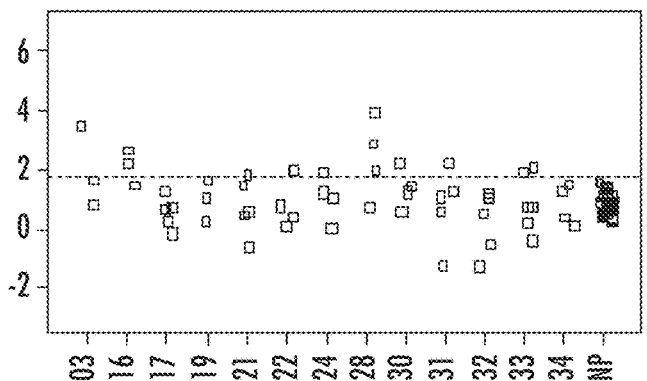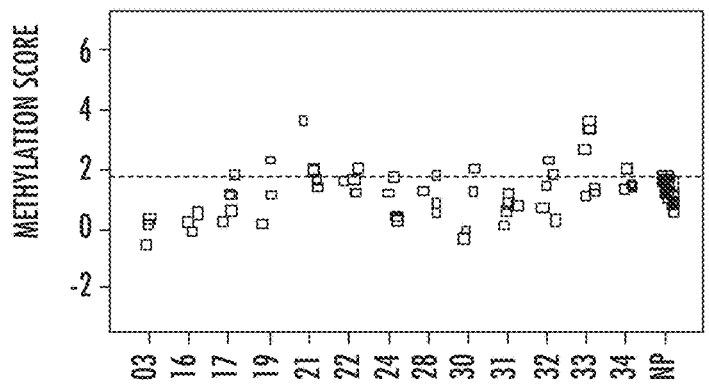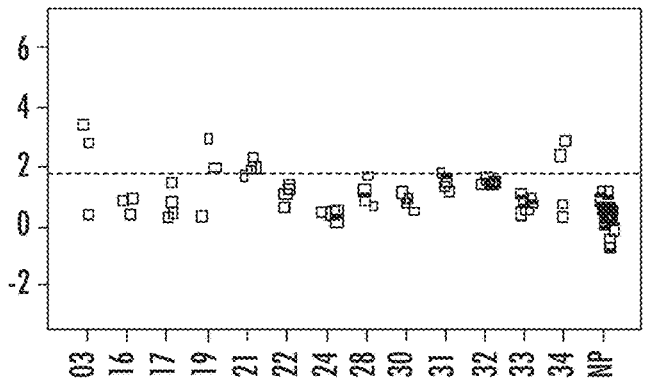
FIG. 24C

DNA METHYLATION MARKERS FOR METASTATIC PROSTATE CANCER

CROSS-REFERENCE TO RELATED APPLICATIONS

This application is a Continuation Application of U.S. application Ser. No. 14/162,180, filed Jan. 23, 2014, which claims the benefit of U.S. Provisional Application No. 61/755,688, filed Jan. 23, 2013, the content of each of the aforementioned applications is herein incorporated by reference in their entirety.

STATEMENT OF GOVERNMENTAL INTEREST

This invention was made with government support under grant no PC073533, CA058236, CA070196, CA113374, CA135008, GM083084, and W81XWH-08-1-0049 awarded by the National Institutes of Health and ARMY Medical Research and Materiel Command. The government has certain rights in the invention.

FIELD OF THE INVENTION

The present invention relates to the field of cancer. More specifically, the present invention provides methods and compositions useful for assessing prostate cancer.

BACKGROUND OF THE INVENTION

Cancer is thought to arise from a series of somatic genome and epigenome defects that allow the cell to evade the rules that control the growth and organization of normal cells (1, 2). In order for genetic and epigenetic somatic genome alterations to drive cancer initiation and progression, the cancer cell would need to maintain those changes in a heritable way throughout disease progression for as long as such changes confer a selective advantage. Genetic alterations are maintained by semiconservative DNA replication and have been implicated in carcinogenesis and disease progression (3). However, epigenetic processes present a fundamental paradox in this regard: They are, by definition, potentially heritable across cell divisions and are stable over time (4, 5), but they can also be plastic (5, 6). For instance, recent reports have suggested that the epigenetic process of DNA methylation can be dynamic and reversible in both replication-dependent [for example, during differentiation and development (6)] and replication independent [for example, cyclical methylation patterns during transcription (7, 8)] processes. Additionally, DNA methylation marks can occur at both copies of a given locus or occur at only one copy, resulting in allele-specific methylation (ASM) (9-11). Unfortunately, most previous reports on DNA methylation in human cancers have only examined total methylation (TM) at an allele-agnostic level, and little is known about the maintenance of ASM in human neoplasia.

Consequently, it is currently unclear which DNA methylation and other epigenetic alterations can be maintained stably as driver genome alterations fueling cancer initiation and progression. A lack of such evidence has dampened enthusiasm for using DNA methylation alterations, which can be more frequent than genetic alterations (12), as targets for biomarker development and therapeutic intervention. Here, we show that, although there is marked heterogeneity in DNA methylation profiles in men with lethal metastatic prostate cancer, each individual's distinct DNA methylation signature is tightly maintained in disseminated metastases.

SUMMARY OF THE INVENTION

Alterations in DNA methylation are a hallmark of human cancers, including prostate cancer. Understanding which of these alterations "drive" cancer initiation and progression to metastatis, and which of these are merely "passengers", not involved in the chain of causation, represents a major translational challenge. To tackle this challenge in the context of metastatic prostate cancer, we carried out genome-scale analyses of DNA methylation alterations in multiple metastases from each of 13 men that died of metastatic prostate cancer. To visualize both the frequency of each methylation alteration in the metastases and the consistency with which each alteration was maintained across all metastases from an individual, we created DNA methylation "cityscape" plots. These analyses revealed that each individual developed a unique DNA methylation signature that was largely maintained across all metastases within that individual. Additionally, a set of DNA "hypermethylation" alterations, defined as regions that were normally unmethylated but acquired cancer-specific DNA methylation, were enriched for prostate cancer "drivers" because they: i) were maintained as hypermethylated across all metastases within each individual despite a strong global tendency for the metastases to lose DNA methylation at normally methylated regions; ii) were highly correlated with alterations in expression of the associated genes; and iii) were enriched near known cancer-related genes and genes involved in differentiation and development. Such DNA hypermethylation alterations are particularly attractive as targets for development of longitudinal markers and therapeutic strategies for prostate cancer management, particularly in the coming era of personalized medicine.

The present inventors have developed a novel method for identification of DNA methylation biomarkers for prostate cancer diagnosis and risk stratification. This strategy involves identification of DNA methylation alterations in prostate cancer that are i) frequently present in prostate cancer; and/or ii) consistently maintained in all metastases from an individual. 2) We have applied this method for the first time and identified novel DNA methylation biomarkers that can help in diagnosis and risk stratification of prostate cancer.

We have identified novel DNA methylation alterations that are either frequently present in metastatic prostate cancer, or consistently maintained across all metastases within an individual. Such alterations are highly correlated with gene expression patterns, and appear to be "drivers" of prostate cancer initiation or progression. These markers can be used to detect aggressive prostate cancer.

The present inventors have also developed and applied a new technology and associated computation methods enabling simultaneous genome-scale analysis of genetic (copy number) and epigenetic (total methylation (TM) and allele-specific methylation (ASM) alternation, This method, called MBD-SNP (see FIG. 1), features affinity enrichment or methylated genomic DNA fragments using a methyl-binding domain polypeptide. In certain embodiments, the methyl-binding domain polypeptide is from the MBD2 protein (MBD2-MBD). The resulting library of methylated DNA fragments and an unenriched total input fraction from the same specimen were then processed and hybridized to Affymetrix SNP 6.0 high-density oligonucleotide microarrays. Comparison of the enriched methylated fraction with the total input using statistical approaches allows parallel genome-scale assessment of TM, ASM, and copy number in a rapid and cost-effective manner.

Accordingly, in one aspect, the present invention provides methods for studying genetic and epigenetic alterations in individuals. In certain embodiments, a method for enabling simultaneous genome-scale analysis of genetic and epigenetic alterations in an individual comprises the steps of (a) digesting a first genomic DNA sample from the individual with a first restriction enzyme; (b) digesting a second genomic DNA sample from the individual with a second restriction enzyme (total input fraction); (c) ligating digested ends of the resulting genomic DNA fragments from steps (a) and (b) with adaptors; (d) enriching the genomic DNA fragments from step (a) for methylated DNA fragments with a methylation-binding domain polypeptide (enriched methylated fraction); (e) amplifying the total input fraction and the enriched methylated fraction using polymerase chain reaction (PCR); (f) labeling the amplified total input fraction and the enriched methylated fraction; (g) hybridizing the amplified total input fraction and the enriched methylated fraction to a single nucleotide polymorphism (SNP) microarray; and (h) analyzing the enriched methylated fraction and total input fraction to assess total methylation (TM) and allele-specific methylation (ASM).

In specific embodiments, the SNP microarray comprises copy number probes to allow for normalization of copy number and probe effects. In a more specific embodiment, the SNP microarray is the Affymetrix® SNP 6.0 high-density oligonucleotide microarray, wherein the first restriction enzyme is Nsp I and wherein the second restriction enzyme is Sty I. In an alternative embodiment, the SNP microarray is the Affymetrix® SNP 6.0 high-density oligonucleotide microarray, wherein the first restriction enzyme is Sty I and wherein the second restriction enzyme is Nsp I.

In one embodiment, the methylation-binding domain polypeptide is from MBD2 (MBD2-MBD). In other embodiments, the TM and ASM are calculated for regions of the genome with ≥2.5% CpG density. In a specific embodiment, the individual has cancer. In a more specific embodiment, the individual has prostate cancer. In such embodiments, the method can further comprise correlating the TM and ASM methylation data with gene expression profiling data from other individuals with prostate cancer and non-prostate cancer to identify potential biomarkers. In another embodiment, the genomic DNA sample is taken from a primary tumor. In yet another embodiment, the genomic DNA sample is taken from a metatstatic tumor. In further embodiments, the method is performed separately on genomic DNA samples taken from a primary tumor and one or more metatstatic tumors.

In another aspect, the present invention provides methods for diagnosing cancer or the likelihood there of. In a specific embodiment, a method for diagnosing prostate cancer in an individual comprises the steps of (a) isolating DNA from a biological sample taken from the individual; (b) contacting the DNA with a primer specific for a SNP biomarker of prostate cancer to form a DNA:primer complex, wherein the SNP biomarker of prostate cancer is a SNP located in the promoter region of one or more genes selected from the group consisting of EY A4, ADAMTS12, ESR1, ESR2 and TNFRSF10D; (c) amplifying the DNA:primer complex using methylation-specific PCR; and (d) identifying the individual as having prostate cancer if the biomarkers are hypermethylated relative to a control.

In another embodiment, the SNP biomarker is a SNP located in the promoter region of one or more genes selected from the group consisting of GSTP1, ESR1, HCN1, ADAMTS12, ESR2, PDDC1, EY A4, TNFRSF10D, and PGR. In an alternative embodiment, the SNP biomarker is a SNP located in the promoter region of one or more genes selected from the group consisting of ALPL; EN1; PTGS2; NHLH2; NRAS; ALOX5; GST02; NKX2-3; BUB3; PAX5; NTRK2; ABCC8; CALCA; BDNF; MIR675,H19; WT1-AS; CD44; TDP1;C13 ORF 143; LOC400236; FOXN3; GSTP1; ESR2; SPA17 SIAE; SSTR1; SESN3; NFATC4; BCAT1; SSPN; HOXC13; SLC5A8; POU 4F1; PT PRR; LGR5; ZNF268; COL2A1; ESD; CDX2; SEPT9; NR0B1; OLIG2; ADAMTS51; CYP251; DPEP1; WFDC1; IRF8; HNF1B; MT1A MT1DP; IL21R; HS3ST2; TU BGCP4 ZSCAN29; SLC26A4.LOC28600_2; SULF1; EXT1; SOX17; FOXE1; TNFRSF10C; TNFRSF10D; SCIN; IGFBP3; CNR1; PT PN3; EY A4; SGK1; ESR1; ISL1; ADAMTS12; APC; PCDH10; WNT5A; CACNA2D3; SLIT2; NNT; UGT3A1; SV2C; CDO1; CRHBP; RASGRF2; and MIR9-2. The biomarkers can comprises any one or more combinations of the foregoing. In other embodiments, the biomarkers can comprise any one of the biomarkers listed in FIG. 5A. In further embodiments, the biomarkers can comprise any one or more combinations of the genes/loci listed in Tables S2, S3, or S4, which are available in Aryee et al., 5(169) SCI. TRANSL. MED. 169ra10 (2013), and are herein incorporated by reference as if fully set forth herein. The biomarkers can be a combination of hypermethylated and hypomethylated regions of the genes described herein.

BRIEF DESCRIPTION OF THE FIGURES

FIG. 24A-24C. Examples of genes in the hypermethylation cityscape (FIG. A). Methylation scores are displayed for multiple tumors from each of 13 lethal metastatic prostate cancer autopsy subjects, and normal prostates (NP) from 24 organ donors. (A) Skyscrapers represent gene promoters that are hypermethylated across almost all tumors. (B) Red mid-rises represent intermediate methylation frequency and high R2 (high maintenance normalized to total variability at the region). (C) Yellow, low- to mid-rises represent low methylation frequency and low R2 (low ratio of inter-subject to intra-subject variability).

DETAILED DESCRIPTION OF THE INVENTION

Figure 1A:
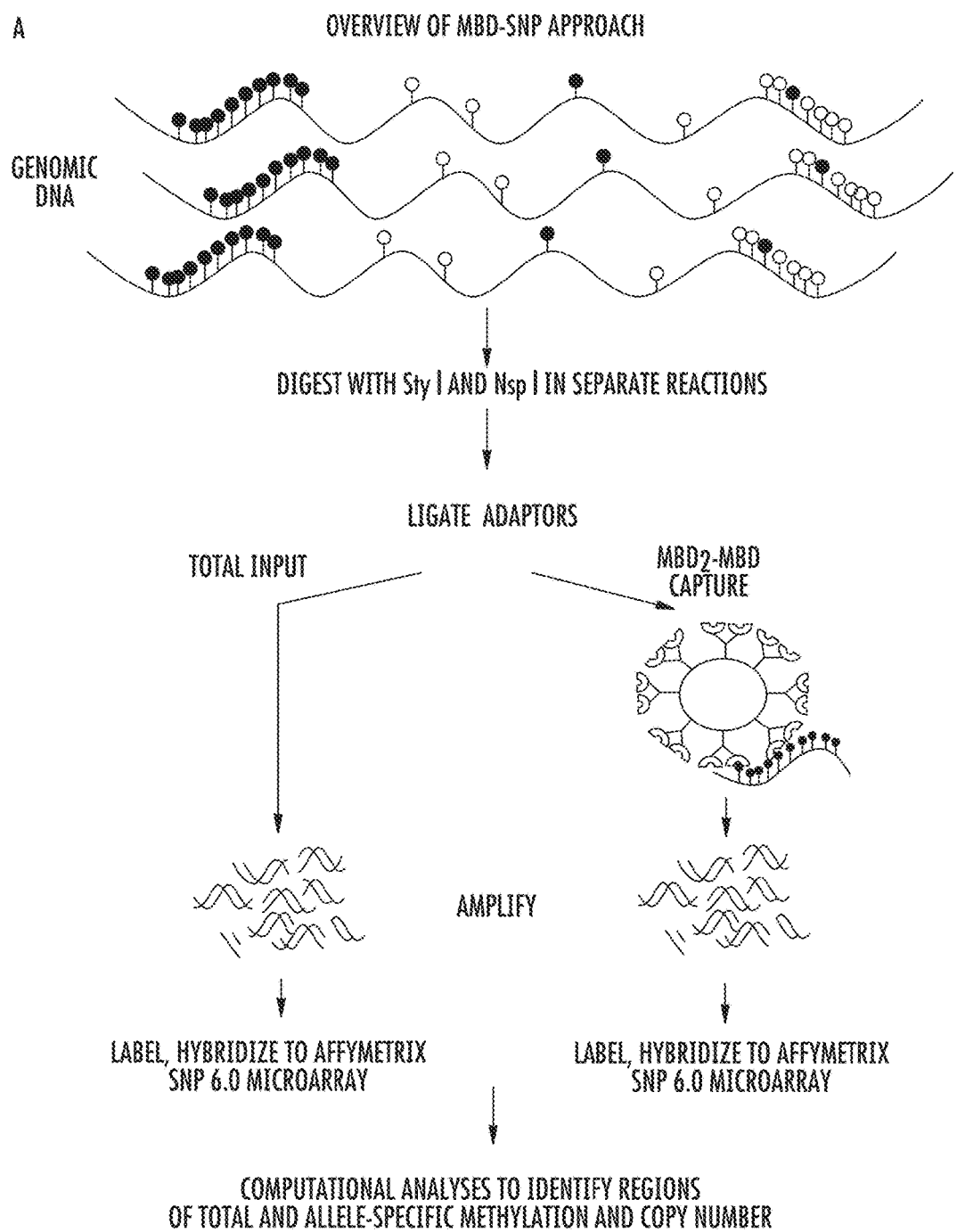
FIG. 1A-1E. Overview and performance of the MBD-SNP method. (A) Overview of MBD-SNP workflow. Genomic DNA is fragmented by Nsp I and Sty I in two separate reactions, and digested ends are ligated to adaptors. These products are then divided into a total input and enriched methylated fraction, the latter of which is subjected to enrichment of methylated DNA fragments by binding to MBD2-MBD immobilized magnetic beads. Both the total and enriched methylated fractions are then subjected to amplification, labeling, and hybridization to Affymetrix SNP 6.0 microarrays. Subsequent computational analyses comparing the enriched methylated and total input fractions allow assessment of TM and ASM. (B) Schematic showing generation of control specimens for testing MBD-SNP performance. (C) Receiver operator characteristic (ROC) curves for classification of TM (allele-agnostic) and ASM, generated by using CS1 (100% methylated), CS3 (0% methylated), and CS2 (50% methylated in individual-specific fashion). (D) ROC curve for array performance as benchmarked against five loci across 44 samples verified by RT-MSP. (E) Concordance between MBD-SNP and Illumina 450 k methylation estimates. There are 13,426 MBD-SNP methylation probes with an Illumina 450 k probe located within 150 base pairs (bp). The MBD-SNP methylation score is plotted against the Illumina 450 k methylation measure for each of the 13,426 probes and each of 12 specimens analyzed on both platforms. Among sites classified as unmethylated (b<0.2) or highly methylated (b>0.8) in the Infinium platform, 86.9% were concordant by the MBD-SNP mixture model-based classification of methylation status ($P \ll 1 \times 10^{-10}$).

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Human cancers almost ubiquitously harbor epigenetic alterations. Although such alterations in epigenetic marks, including DNA methylation, are potentially heritable, they can also be dynamically altered. Given this potential for plasticity, the degree to which epigenetic changes can be subject to selection and act as drivers of neoplasia has been questioned. We carried out genome-scale analyses of DNA methylation alterations in lethal metastatic prostate cancer and created DNA methylation "cityscape" plots to visualize these complex data. We show that somatic DNA methylation alterations, despite showing marked interindividual heterogeneity among men with lethal metastatic prostate cancer, were maintained across all metastases within the same individual. The overall extent of maintenance in DNA methylation changes was comparable to that of genetic copy number alterations. Regions that were frequently hypermethylated across individuals were markedly enriched for cancer- and development/differentiation-related genes. Additionally, regions exhibiting high consistency of hypermethylation across metastases within individuals, even if variably hypermethylated across individuals, showed enrichment for cancer-related genes. Whereas some regions showed intraindividual metastatic tumor heterogeneity in promoter methylation, such methylation alterations were generally not correlated with gene expression. This was despite a general tendency for promoter methylation patterns to be strongly correlated with gene expression, particularly at regions that were variably methylated across individuals. These findings suggest that DNA methylation alterations have the potential for producing selectable driver events in carcinogenesis and disease progression and highlight the possibility of targeting such epigenome alterations for development of longitudinal markers and therapeutic strategies.

I. Definitions

As used herein, the term "comparing" refers to making an assessment of how the methylation status, proportion, level or cellular localization of one or more biomarkers in a sample from a patient relates to the methylation status, proportion, level or cellular localization of the corresponding one or more biomarkers in a standard or control sample. For example, "comparing" may refer to assessing whether the methylation status, proportion, level, or cellular localization of one or more biomarkers in a sample from a patient is the same as, more or less than, or different from the methylation status, proportion, level, or cellular localization of the corresponding one or more biomarkers in standard or control sample. More specifically, the term may refer to assessing whether the methylation status, proportion, level, or cellular localization of one or more biomarkers in a sample from a patient is the same as, more or less than, different from or otherwise corresponds (or not) to the methylation status, proportion, level, or cellular localization of predefined biomarker levels that correspond to, for example, a patient having prostate cancer, at risk for developing prostate cancer, not having prostate cancer, is responding to treatment for prostate cancer, is not responding to treatment for prostate cancer, is/is not likely to respond to a particular prostate cancer treatment, or having/not having another disease or condition. In a specific embodiment, the term "comparing" refers to assessing whether the methylation level of one or more biomarkers of the present invention in a sample from a patient is the same as, more or less than, different from other otherwise correspond (or not) to methylation levels of the same biomarkers in a control sample (e.g., predefined levels that correlate to uninfected individuals, standard prostate cancer levels, etc.).

As used herein, the terms "indicates" or "correlates" (or "indicating" or "correlating," or "indication" or "correlation," depending on the context) in reference to a parameter, e.g., a modulated proportion, level, or cellular localization in a sample from a patient, may mean that the patient has prostate cancer. In specific embodiments, the parameter may comprise the methylation status or level of one or more biomarkers of the present invention. A particular set or pattern of methylation of one or more biomarkers may indicate that a patient has prostate cancer (i.e., correlates to a patient having prostate cancer) or is at risk of developing prostate cancer. In other embodiments, a particular set or pattern of methylation of one or more biomarkers may be correlated to a patient being unaffected. In certain embodiments, "indicating," or "correlating," as used according to the present invention, may be by any linear or non-linear method of quantifying the relationship between methylation levels of biomarkers to a standard, control or comparative value for the assessment of the diagnosis, prediction of prostate cancer or prostate cancer progression, assessment of efficacy of clinical treatment, identification of a patient that may respond to a particular treatment regime or pharmaceutical agent, monitoring of the progress of treatment, and in the context of a screening assay, for the identification of an anti-prostate cancer therapeutic.

The terms "patient," "individual," or "subject" are used interchangeably herein, and refer to a mammal, particularly, a human. The patient may have mild, intermediate or severe disease. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining a patient sample and/or detecting the methylation status or level of a biomarker(s) in a sample. In one embodiment, the terms refer to obtaining a patient sample and detecting the methylation status or level of one or more biomarkers in the sample. In another embodiment, the terms "measuring" and "determining" mean detecting the methylation status or level of one or more biomarkers in a patient sample. Measuring can be accomplished by methods known in the art and those further described herein including, but not limited to, quantitative polymerase chain reaction (PCR). The term "measuring" is also used interchangeably throughout with the term "detecting."

The term "methylation" refers to, for example, cytosine methylation at positions C5 or N4 of cytosine, the N6 position of adenine, or other types of nucleic acid methylation. In vitro amplified DNA is unmethylated because in vitro DNA amplification methods do not retain the methylation pattern of the amplification template. However, "unmethylated DNA" or "methylated DNA" can also refer to amplified DNA whose original template was unmethylated or methylated, respectively. By "hypermethylation" or "elevated level of methylation" is meant an increase in methylation of a region of DNA (e.g., a biomarker of the present invention) that is considered statistically significant over levels of a control population. "Hypermethylation" or "elevated level of methylation" may refer to increased levels seen in a patient over time.

In particular embodiments, a biomarker would be unmethylated in a normal sample (e.g., normal or control tissue without disease, or normal or control body fluid, stool, blood, serum, amniotic fluid), most importantly in healthy stool, blood, serum, amniotic fluid or other body fluid. In other embodiments, a biomarker would be hypermethylated in a sample from a patient having or at risk of prostate cancer, preferably at a methylation frequency of at least about 30%, at least about 40%, at least about 50%, at least about 60%, at least about 70%, at least about 75%, at least about 80%, at least about 85%, at least about 90%, at least about 95%, or about 100%.

A "methylation profile" refers to a set of data representing the methylation states or levels of one or more loci within a molecule of DNA from e.g., the genome of an individual or cells or sample from an individual. The profile can indicate the methylation state of every base in an individual, can comprise information regarding a subset of the base pairs (e.g., the methylation state of specific restriction enzyme recognition sequence) in a genome, or can comprise information regarding regional methylation density of each locus. In some embodiments, a methylation profile refers to the methylation states or levels of one or more biomarkers described herein, including, but not limited to, EY A4, ADAMTS12, ESR1, ESR2 and TNFRSF10D. In more specific embodiments, a methylation profile refers to the methylation states of levels of the promoter regions one or more of GSTP1, ESR1, HCN1, ADAMTS12, ESR2, PDDC1, EY A4, TNFRSF10D, and PGR. In an alternative embodiment, a methylation profile refers to the methylation states of levels of the promoter regions one or more of ALPL; EN1; PTGS2; NHLH2; NRAS; ALOX5; GST02; NKX2-3; BUB3; PAX5; NTRK2; ABCC8; CALCA; BDNF; MIR675, H19; WT1-AS; CD44; TDP1;C13 ORF 143; LOC400236; FOXN3; GSTP1; ESR2; SPA17 SIAE; SSTR1; SESN3; NFATC4; BCAT1; SSPN; HOXC13; SLC5A8; POU 4F1; PT PRR; LGR5; ZNF268; COL2A1; ESD; CDX2; SEPT9; NR0B1; OLIG2; ADAMTS51; CYP251; DPEP1; WFDC1; IRF8; HNF1B; MT1A MT1DP; IL21R; HS3ST2; TU BGCP4 ZSCAN29; SLC26A4.LOC28600_2; SULF1; EXT1; SOX17; FOXE1; TNFRSF10C; TNFRSF10D; SCIN; IGFBP3; CNR1; PT PN3; EY A4; SGK1; ESR1; ISL1; ADAMTS12; APC; PCDH10; WNT5A; CACNA2D3; SLIT2; NNT; UGT3A1; SV2C; CDO1; CRHBP; RASGRF2; and MIR9-2.

The terms "methylation status" or "methylation level" refers to the presence, absence and/or quantity of methylation at a particular nucleotide, or nucleotides within a portion of DNA. The methylation status of a particular DNA sequence (e.g., a DNA biomarker or DNA region as described herein) can indicate the methylation state of every base in the sequence or can indicate the methylation state of a subset of the base pairs (e.g., of cytosines or the methylation state of one or more specific restriction enzyme recognition sequences) within the sequence, or can indicate information regarding regional methylation density within the sequence without providing precise information of where in the sequence the methylation occurs. The methylation status can optionally be represented or indicated by a "methylation value" or "methylation level." A methylation value or level can be generated, for example, by quantifying the amount of intact DNA present following restriction digestion with a methylation dependent restriction enzyme. In this example, if a particular sequence in the DNA is quantified using quantitative PCR, an amount of template DNA approximately equal to a mock treated control indicates the sequence is not highly methylated whereas an amount of template substantially less than occurs in the mock treated sample indicates the presence of methylated DNA at the sequence. Accordingly, a value, i.e., a methylation value, for example from the above described example, represents the methylation status and can thus be used as a quantitative indicator of methylation status. This is of particular use when it is desirable to compare the methylation status of a sequence in a sample to a threshold value.

A "methylation-dependent restriction enzyme" refers to a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., DpnI) and enzymes that cut at a sequence near but not at the recognition sequence (e.g., McrBC). For example, McrBC's recognition sequence is 5' RmC (N40-3000) RmC 3' where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC, McrA, MrrA, BisI, GlaI and DpnI. One of skill in the art will appreciate that any methylation-dependent restriction enzyme, including homologs and orthologs of the restriction enzymes described herein, is also suitable for use in the present invention.

A "methylation-sensitive restriction enzyme" refers to a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al., 22(17) NUCLEIC ACIDS RES. 3640-59 (1994). Suitable methylation-sensitive restriction enzymes that do not cleave DNA at or near their recognition sequence when a cytosine within the recognition sequence is methylated at position $C^5$ include, e.g., Aat II, Aci I, Acd I, Age I, Alu I, Asc I, Ase I, AsiS I, Bbe I, BsaA I, BsaH I, BsiE I, BsiW I, BsrF I, BssH II, BssK I, BstB I, BstN I, BstU I, Cla I, Eae I, Eag I, Fau I, Fse I, Hha I, HinP1 I, HinC II, Hpa II, Hpy99 I, HpyCH4 IV, Kas I, Mbo I, Mlu I, MapA1 I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes that do not cleave DNA at or near their recognition sequence when an adenosine within the recognition sequence is methylated at position $N^6$ include, e.g., Mbo I. One of skill in the art will appreciate that any methylation-sensitive restriction enzyme, including homologs and orthologs of the restriction enzymes described herein, is also suitable for use in the present invention. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3AI is sensitive (i.e., fails to cut)to the presence of a methylated cytosine at or near its recognition sequence, but is insensitive (i.e., cuts) to the presence of a methylated adenosine at or near its recognition sequence. One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of prostate cancer. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, urine, saliva, amniotic fluid, stool and synovial fluid), solid tissue samples such as a biopsy specimen or tissue cultures or cells derived therefrom and the progeny thereof. In a specific embodiment, a sample comprises a blood sample. In another embodiment, a serum sample is used. In another embodiment, a sample comprises amniotic fluid. In yet another embodiment, a sample comprises amniotic fluid. The definition also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

Various methodologies of the instant invention include a step that involves comparing a value, level, feature, characteristic, property, etc. to a "suitable control," referred to interchangeably herein as an "appropriate control" or a "control sample." A "suitable control," "appropriate control" or a "control sample" is any control or standard familiar to one of ordinary skill in the art useful for comparison purposes. In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the biomarkers of the present invention may be assayed for their methylation level in a sample from an unaffected individual (UI) or a normal control individual (NC) (both terms are used interchangeably herein). In another embodiment, a "suitable control" or "appropriate control" is a value, level, feature, characteristic, property, etc. determined prior to performing a therapy (e.g., a prostate cancer treatment) on a patient. In yet another embodiment, a methylation status/level, transcription rate, mRNA level, translation rate, protein level, biological activity, cellular characteristic or property, genotype, phenotype, etc. can be determined prior to, during, or after administering a therapy into a cell, organ, or patient. In a further embodiment, a "suitable control" or "appropriate control" is a predefined value, level, feature, characteristic, property, etc. A "suitable control" can be a methylation profile of one or more biomarkers of the present invention that correlates to prostate cancer, to which a patient sample can be compared. The patient sample can also be compared to a negative control, i.e., a methylation profile that correlates to not having prostate cancer.

II. Hypermethylated Biomarkers and Detection Thereof

The biomarkers of the present invention are differentially methylated in prostate cancer versus normal tissue. Such biomarkers can be used individually as diagnostic tool, or in combination as a biomarker panel. In particular embodiments, the biomarkers include one or more of EY A4, ADAMTS12, ESR1, ESR2 and TNFRSF10D. In more specific embodiments, biomarkers comprise a SNP located in the promoter region of one or more of GSTP1, ESR1, HCN1, ADAMTS12, ESR2, PDDC1, EY A4, TNFRSF10D, and PGR. In an alternative embodiment, the biomarkers comprise a SNP located in the promoter region of one or more of ALPL; EN1; PTGS2; NHLH2; NRAS; ALOX5; GST02; NKX2-3; BUB3; PAX5; NTRK2; ABCC8; CALCA; BDNF; MIR675,H19; WT1-AS; CD44; TDP1; C13 ORF 143; LOC400236; FOXN3; GSTP1; ESR2; SPA17 SIAE; SSTR1; SESN3; NFATC4; BCAT1; SSPN; HOXC13; SLC5A8; POU 4F1; PT PRR; LGR5; ZNF268; COL2A1; ESD; CDX2; SEPT9; NR0B1; OLIG2; ADAMTS51; CYP251; DPEP1; WFDC1; IRF8; HNF1B; MT1A MT1DP; IL21R; HS3ST2; TU BGCP4 ZSCAN29; SLC26A4.LOC28600_2; SULF1; EXT1; SOX17; FOXE1; TNFRSF10C; TNFRSF10D; SCIN; IGFBP3; CNR1; PT PN3; EY A4; SGK1; ESR1; ISL1; ADAMTS12; APC; PCDH10; WNT5A; CACNA2D3; SLIT2; NNT; UGT3A1; SV2C; CDO1; CRHBP; RASGRF2; and MIR9-2. The sequences of these biomarkers are publicly available.

The DNA biomarkers of the present invention comprise fragments of a polynucleotide (e.g., regions of genome polynucleotide or DNA) which likely contain CpG island(s), or fragments which are more susceptible to methylation or demethylation than other regions of genome DNA. The term "CpG islands" is a region of genome DNA which shows higher frequency of 5'-CG-3' (CpG) dinucleotides than other regions of genome DNA. Methylation of DNA at CpG dinucleotides, in particular, the addition of a methyl group to position 5 of the cytosine ring at CpG dinucleotides, is one of the epigenetic modifications in mammalian cells. CpG islands often harbor the promoters of genes and play a pivotal role in the control of gene expression. In normal tissues CpG islands are usually unmethylated, but a subset of islands becomes methylated during the development of a disease or condition (e.g., prostate cancer).

There are a number of methods that can be employed to measure, detect, determine, identify, and characterize the methylation status/level of a biomarker (i.e., a region/fragment of DNA or a region/fragment of genome DNA (e.g., CpG island-containing region/fragment)) in the development of a disease or condition (e.g., prostate cancer) and thus, diagnose the onset, presence or status of the disease or condition.

In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. Pat. Nos. 7,910,296; 7,901,880; and 7,459,274. In some embodiments, amplification can be performed using primers that are gene specific. Alternatively, adaptors can be added to the ends of the randomly fragmented DNA, the DNA can be digested with a methylation-dependent or methylation-sensitive restriction enzyme, intact DNA can be amplified using primers that hybridize to the adaptor sequences. In this case, a second step can be performed to determine the presence, absence or quantity of a particular gene in an amplified pool of DNA. In some embodiments, the DNA is amplified using real-time, quantitative PCR.

In other embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The quantity of methylation of a locus of DNA can be determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. Pat. No. 7,910,296.

Quantitative amplification methods (e.g., quantitative PCR or quantitative linear amplification) can be used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602, as well as in, e.g., DeGraves, et al., 34(1) BIOTECHNIQUES 106-15 (2003); Deiman B, et al., 20(2) MOL. BIOTECHNOL. 163-79 (2002); and Gibson et al., 6 GENOME RESEARCH 995-1001 (1996). Amplifications may be monitored in "real time."

Additional methods for detecting DNA methylation can involve genomic sequencing before and after treatment of the DNA with bisulfite. See, e.g., Frommer et al., 89 PROC. NATL. ACAD. SCI. USA 1827-31 (1992). When sodium bisulfite is contacted to DNA, unmethylated cytosine is converted to uracil, while methylated cytosine is not modified. In some embodiments, restriction enzyme digestion of PCR products amplified from bisulfite-converted DNA is used to detect DNA methylation. See, e.g., Xiong & Laird, 25 NUCLEIC ACIDS RES. 2532-34 (1997); and Sadri & Hornsby, 24 NUCL. ACIDS RES. 5058-59 (1996).

In some embodiments, a MethyLight assay is used alone or in combination with other methods to detect DNA methylation. See, Eads et al., 59 CANCER RES. 2302-06 (1999). Briefly, in the MethyLight process genomic DNA is converted in a sodium bisulfite reaction (the bisulfite process converts unmethylated cytosine residues to uracil). Amplification of a DNA sequence of interest is then performed using PCR primers that hybridize to CpG dinucleotides. By using primers that hybridize only to sequences resulting from bisulfite conversion of unmethylated DNA, (or alternatively to methylated sequences that are not converted) amplification can indicate methylation status of sequences where the primers hybridize. Similarly, the amplification product can be detected with a probe that specifically binds to a sequence resulting from bisulfite treatment of a unmethylated (or methylated) DNA. If desired, both primers and probes can be used to detect methylation status. Thus, kits for use with MethyLight can include sodium bisulfite as well as primers or detectably-labeled probes (including but not limited to Taqman or molecular beacon probes) that distinguish between methylated and unmethylated DNA that have been treated with bisulfite. Other kit components can include, e.g., reagents necessary for amplification of DNA including but not limited to, PCR buffers, deoxynucleotides; and a thermostable polymerase.

In other embodiments, a Methylation-sensitive Single Nucleotide Primer Extension (Ms-SNuPE) reaction is used alone or in combination with other methods to detect DNA methylation. See Gonzalgo & Jones, 25 NUCLEIC ACIDS RES. 2529-31 (1997). The Ms-SNuPE technique is a quantitative method for assessing methylation differences at specific CpG sites based on bisulfite treatment of DNA, followed by single-nucleotide primer extension. Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Typical reagents (e.g., as might be found in a typical Ms-SNuPE-based kit) for Ms-SNuPE analysis can include, but are not limited to: PCR primers for specific gene (or methylation-altered DNA sequence or CpG island); optimized PCR buffers and deoxynucleotides; gel extraction kit; positive control primers; Ms-SNuPE primers for a specific gene; reaction buffer (for the Ms-SNuPE reaction); and detectably-labeled nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

In further embodiments, a methylation-specific PCR reaction is used alone or in combination with other methods to detect DNA methylation. A methylation-specific PCR assay entails initial modification of DNA by sodium bisulfite, converting all unmethylated, but not methylated, cytosines to uracil, and subsequent amplification with primers specific for methylated versus unmethylated DNA. See, Herman et al., 93 PROC. NATL. ACAD. SCI. USA 9821-26, (1996); and U.S. Pat. No. 5,786,146.

Additional methylation detection methods include, but are not limited to, methylated CpG island amplification (see, Toyota et al., 59 CANCER RES. 2307-12 (1999)) and those methods described in, e.g., U.S. Pat. Nos. 7,553,627; 6,331,393; U.S. patent Ser. No. 12/476,981; U.S. Patent Publication No. 2005/0069879; Rein, et al., 26(10) NUCLEIC ACIDS RES. 2255-64 (1998); and Olek et al., 17(3) NAT. GENET. 275-6 (1997).

III. Determination of a Patient's Prostate Cancer Status

The present invention relates to the use of biomarkers to detect or predict prostate cancer. More specifically, the biomarkers of the present invention can be used in diagnostic tests to determine, qualify, and/or assess prostate cancer status, for example, to diagnose or predict prostate cancer, in an individual, subject or patient. More specifically, the biomarkers to be detected in diagnosing prostate cancer include, but are not limited to, one or more of EY A4, ADAMTS12, ESR1, ESR2 and TNFRSF10D. In more specific embodiments, biomarkers comprise a SNP located in the promoter region of one or more of GSTP1, ESR1, HCN1, ADAMTS12, ESR2, PDDC1, EY A4, TNFRSF10D, and PGR. In an alternative embodiment, the biomarkers comprise a SNP located in the promoter region of one or more of ALPL; EN1; PTGS2; NHLH2; NRAS; ALOX5; GST02; NKX2-3; BUB3; PAX5; NTRK2; ABCC8; CALCA; BDNF; MIR675,H19; WT1-AS; CD44; TDP1; C13 ORF 143; LOC400236; FOXN3; GSTP1; ESR2; SPA17 SIAE; SSTR1; SESN3; NFATC4; BCAT1; SSPN; HOXC13; SLC5A8; POU 4F1; PT PRR; LGR5; ZNF268; COL2A1; ESD; CDX2; SEPT9; NR0B1; OLIG2; ADAMTS51; CYP251; DPEP1; WFDC1; IRF8; HNF1B; MT1A MT1DP; IL21R; HS3ST2; TU BGCP4 ZSCAN29; SLC26A4.LOC28600_2; SULF1; EXT1; SOX17; FOXE1; TNFRSF10C; TNFRSF10D; SCIN; IGFBP3; CNR1; PT PN3; EY A4; SGK1; ESR1; ISL1; ADAMTS12; APC; PCDH10; WNT5A; CACNA2D3; SLIT2; NNT; UGT3A1; SV2C; CDO1; CRHBP; RASGRF2; and MIR9-2. Other biomarkers known in the relevant art may be used in combination with the biomarkers described herein.

A. Biomarker Panels

The biomarkers of the present invention can be used in diagnostic tests to assess, determine, and/or qualify (used interchangeably herein) prostate cancer status in a patient. The phrase "prostate cancer status" includes any distinguishable manifestation of the disease, including non-disease. For example, prostate cancer status includes, without limitation, the presence or absence of prostate cancer in a patient), the risk of developing prostate cancer, the stage of prostate cancer, the progress of prostate cancer (e.g., progress of prostate cancer over time) and the effectiveness or response to treatment of prostate cancer (e.g., clinical follow up and surveillance of prostate cancer after treatment). Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker panels of the present invention may show a statistical difference in different prostate cancer statuses of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9.

The biomarkers are differentially methylated in UI (or NC) and prostate cancer, and, therefore, are useful in aiding in the determination of prostate cancer status. In certain embodiments, the biomarkers are measured in a patient sample using the methods described herein and compared, for example, to predefined biomarker levels and correlated to prostate cancer status. In particular embodiments, the measurement(s) may then be compared with a relevant diagnostic amount(s), cut-off(s), or multivariate model scores that distinguish a positive prostate cancer status from a negative prostate cancer status. The diagnostic amount(s) represents a measured amount of a hypermethylated biomarker(s) above which or below which a patient is classified as having a particular prostate cancer status. For example, if the biomarker(s) is/are hypermethylated compared to normal during prostate cancer, then a measured amount(s) above the diagnostic cutoff(s) provides a diagnosis of prostate cancer. Alternatively, if the biomarker(s) is/are hypomethylated in a patient, then a measured amount(s) at or below the diagnostic cutoff(s) provides a diagnosis of non-prostate cancer. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarker hypermethylation in a statistically significant number of samples from patients with the different prostate cancer statuses, and drawing the cut-off to suit the desired levels of specificity and sensitivity.

Indeed, as the skilled artisan will appreciate there are many ways to use the measurements of the methylation status of two or more biomarkers in order to improve the diagnostic question under investigation. In a quite simple, but nonetheless often effective approach, a positive result is assumed if a sample is hypermethylation positive for at least one of the markers investigated.

Furthermore, in certain embodiments, the methylation values measured for markers of a biomarker panel are mathematically combined and the combined value is correlated to the underlying diagnostic question. Methylated biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating methylation status of a biomarker combination of the present invention, e.g. to diagnose prostate cancer, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al.,12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45

MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

B. Determining Risk of Developing Prostate Cancer

In a specific embodiment, the present invention provides methods for determining the risk of developing prostate cancer in a patient. Biomarker methylation percentages, amounts or patterns are characteristic of various risk states, e.g., high, medium or low. The risk of developing prostate cancer is determined by measuring the methylation status of the relevant biomarkers and then either submitting them to a classification algorithm or comparing them with a reference amount, i.e., a predefined level or pattern of methylated (and/or unmethylated) biomarkers that is associated with the particular risk level.

C. Determining Prostate Cancer Severity

In another embodiment, the present invention provides methods for determining the severity of prostate cancer in a patient. A particular stage or severity of prostate cancer may have a characteristic level of hypermethylation of a biomarker or relative hypermethylated levels of a set of biomarkers (a pattern). The severity of prostate cancer can be determined by measuring the methylation status of the relevant biomarkers and then either submitting them to a classification algorithm or comparing them with a reference amount, i.e., a predefined methylation level or pattern of methylated biomarkers that is associated with the particular stage.

D. Determining Prostate Cancer Prognosis

In one embodiment, the present invention provides methods for determining the course of prostate cancer in a patient. Prostate cancer course refers to changes in prostate cancer status over time, including prostate cancer progression (worsening) and prostate cancer regression (improvement). Over time, the amount or relative amount (e.g., the pattern) of hypermethylation of the biomarkers changes. For example, hypermethylation of biomarker "X" and "Y" may be increased with prostate cancer. Therefore, the trend of these biomarkers, either increased or decreased methylation over time toward prostate cancer or non-prostate cancer indicates the course of the disease. Accordingly, this method involves measuring the methylation level or status of one or more biomarkers in a patient at least two different time points, e.g., a first time and a second time, and comparing the change, if any. The course of prostate cancer is determined based on these comparisons.

E. Patient Management

In certain embodiments of the methods of qualifying prostate cancer status, the methods further comprise managing patient treatment based on the status. Such management includes the actions of the physician or clinician subsequent to determining prostate cancer status. For example, if a physician makes a diagnosis or prognosis of prostate cancer, then a certain regime of monitoring would follow. An assessment of the course of prostate cancer using the methods of the present invention may then require a certain prostate cancer therapy regimen. Alternatively, a diagnosis of non-prostate cancer might be followed with further testing to determine a specific disease that the patient might be suffering from. Also, further tests may be called for if the diagnostic test gives an inconclusive result on prostate cancer status.

F. Determining Therapeutic Efficacy of Pharmaceutical Drug

In another embodiment, the present invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of hypermethylation of one or more of the biomarkers of the present invention may change toward a non-prostate cancer profile. Therefore, one can follow the course of the methylation status of one or more biomarkers in the patient during the course of treatment. Accordingly, this method involves measuring methylation levels of one or more biomarkers in a patient receiving drug therapy, and correlating the levels with the prostate cancer status of the patient (e.g., by comparison to predefined methylation levels of the biomarkers that correspond to different prostate cancer statuses). One embodiment of this method involves determining the methylation levels of one or more biomarkers at at least two different time points during a course of drug therapy, e.g., a first time and a second time, and comparing the change in methylation levels of the biomarkers, if any. For example, the methylation levels of one or more biomarkers can be measured before and after drug administration or at two different time points during drug administration. The effect of therapy is determined based on these comparisons. If a treatment is effective, then the methylation status of one or more biomarkers will trend toward normal, while if treatment is ineffective, the methylation status of one or more biomarkers will trend toward prostate cancer indications.

G. Generation of Classification Algorithms for Qualifying Prostate Cancer Status In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., diseased versus non-diseased).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarker biomarkers already discovered, and for finding new biomarker biomarkers. The classification algorithms, in turn, form the base for diagnostic tests by providing diagnostic values (e.g., cut-off points) for biomarkers used singly or in combination.

H. Kits for the Detection of Prostate Cancer Biomarker Biomarkers

In another aspect, the present invention provides kits for qualifying prostate cancer status, which kits are used to detect or measure the methylation status/levels of the biomarkers described herein. Such kits can comprise at least one polynucleotide that hybridizes to at least one of the diagnostic biomarker sequences of the present invention and at least one reagent for detection of gene methylation. Reagents for detection of methylation include, e.g., sodium bisulfate, polynucleotides designed to hybridize to a sequence that is the product of a biomarker sequence of the invention if the biomarker sequence is not methylated (e.g., containing at least one C→U conversion), and/or a methylation-sensitive or methylation-dependent restriction enzyme. The kits can further provide solid supports in the form of an assay apparatus that is adapted to use in the assay. The kits may further comprise detectable labels, optionally linked to a polynucleotide, e.g., a probe, in the kit. Other materials useful in the performance of the assays can also be included in the kits, including test tubes, transfer pipettes, and the like. The kits can also include written instructions for the use of one or more of these reagents in any of the assays described herein.

In some embodiments, the kits of the invention comprise one or more (e.g., 1, 2, 3, 4, or more) different polynucleotides (e.g., primers and/or probes) capable of specifically amplifying at least a portion of a DNA region of a biomarker of the present invention including, but not limited to, EY A4, ADAMTS12, ESR1, ESR2 and TNFRSF10D. Optionally, one or more detectably-labeled polypeptides capable of hybridizing to the amplified portion can also be included in the kit. In some embodiments, the kits comprise sufficient primers to amplify 2, 3, 4, 5, 6, 7, 8, 9, 10, or more different DNA regions or portions thereof, and optionally include detectably-labeled polynucleotides capable of hybridizing to each amplified DNA region or portion thereof. The kits further can comprise a methylation-dependent or methylation sensitive restriction enzyme and/or sodium bisulfite.

In some embodiments, the kits comprise sodium bisulfite, primers and adapters (e.g., oligonucleotides that can be ligated or otherwise linked to genomic fragments) for whole genome amplification, and polynucleotides (e.g., detectably-labeled polynucleotides) to quantify the presence of the converted methylated and or the converted unmethylated sequence of at least one cytosine from a DNA region of a biomarker of the present invention including, but not limited to, EY A4, ADAMTS12, ESR1, ESR2 and TNFRSF10D.

In some embodiments, the kits comprise methylation sensing restriction enzymes (e.g., a methylation-dependent restriction enzyme and/or a methylation-sensitive restriction enzyme), primers and adapters for whole genome amplification, and polynucleotides to quantify the number of copies of at least a portion of a DNA region of a biomarker of the present invention including, but not limited to, EY A4, ADAMTS12, ESR1, ESR2 and TNFRSF10D.

In some embodiments, the kits comprise a methylation binding moiety and one or more polynucleotides to quantify the number of copies of at least a portion of a DNA region of a biomarker of the present invention including, but not limited to, EY A4, ADAMTS12, ESR1, ESR2 and TNFRSF10D. A methylation binding moiety refers to a molecule (e.g., a polypeptide) that specifically binds to methyl-cytosine. Examples include restriction enzymes or fragments thereof that lack DNA cutting activity but retain the ability to bind methylated DNA, antibodies that specifically bind to methylated DNA, etc.).

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Prostate specimens. Tissues from multiple anatomically distinct prostate cancer metastases and matched normal tissues from nonprostate tissues were obtained through the Project to Eliminate Lethal Prostate Cancer (PELICAN) rapid autopsy program at the Johns Hopkins Autopsy Study of Lethal Prostate Cancer, as previously described (16). Organ donor benign prostate tissues were obtained from 24 brain-dead organ donors with no evidence of prostate cancer. Tissue samples were snap-frozen, microdissected with a cryostat, and subjected to DNA isolation as described previously (19). Subject and sample data are provided in tables S5 and S6.

MBD-SNP approach. The methyl-binding domain of the MBD2 protein (MBD2-MBD) can bind methylated DNA fragments with exquisite selectivity and has been used to efficiently enrich methylated DNA fragments from genomic DNA (14, 15). Analyzing the resulting methylated DNA library with real-time PCR, tiling microarrays, and next-generation sequencing has allowed gene-specific, chromosome-wide, and genome-wide DNA methylation analysis previously (14, 15, 53). In the MBD-SNP assay described here, we use the MBD2-MBD polypeptide to isolate methylated DNA fragments from genomic DNA samples followed by analysis with Affymetrix SNP 6.0 high-density oligonucleotide microarrays. Comparison with an unenriched total input fraction then allows genomescale determination of TM and ASM and copy number in an integrated fashion for each specimen. Briefly, each genomic DNA specimen (1 mg) was divided into two equal fractions: (i) an enriched methylated fraction (EM) and (ii) a total input fraction (TI). Each of these fractions was further divided into two equal reactions, each of which was digested with either the Nsp I or Sty I restriction enzymes in separate reactions. Therefore, each fraction (EM or TI) and restriction enzyme digest (Nsp I or Sty I) received 250 ng of genomic DNA. The resulting genomic DNA fragments were then ligated with Affymetrix SNP 6.0 assay adaptors. These restriction digest and adaptor ligation steps were carried out following the Affymetrix SNP 6.0 assay protocols. Up to this point, the EM and TI fractions were treated identically. After adaptor ligation, the TI fraction was brought to a total volume of 100 ml with water and set aside on ice; the EM fraction was subjected to enrichment for methylated DNA fragments with MBD2-MBD polypeptides immobilized on magnetic beads as previously described (14, 15), except that the final DNA was eluted in 45 ml of EB1 buffer {0.2× NEBuffer 1 [New England Biolabs (NEB)], 0.2× bovine serum albumin (BSA) (NEB), 0.25× T4 DNA ligase buffer (NEB) in water} for the DNA previously digested by Nsp I and 35 ml of EB2 buffer [0.2× NEBuffer 3, 0.2× BSA (NEB), 0.25× T4 DNA ligase buffer (NEB) in water] for the DNA previously digested by Sty I. These elution buffers were formulated so that the DNA from the EM fractions would be in the same buffers as the DNA from the TI fraction. For the EM and TI fractions previously digested with Nsp I, four 10-ml aliquots of DNA were amplified in four separate 100-ml one-primer amplification reactions (30 cycles); for the EM and TI fractions previously digested with Sty I, three 10-ml aliquots of DNA were amplified in three separate one-primer amplification reactions (30 cycles), according to the Affymetrix SNP 6.0 microarray protocol. The seven amplification reactions for each fraction (EM and TI) were then pooled and subjected to cleanup, labeling, hybridization to Affymetrix SNP 6.0 microarrays, washing, and scanning according to the manufacturer's protocols.

Affymetrix SNP 6.0 microarray and MBD-SNP probe selection. The Affymetrix SNP 6.0 microarray contains copy number probes at ~900,000 nonpolymorphic loci and an additional 900,000 singlenucleotide polymorphism (SNP) probe sets at polymorphic loci. Our assay allows estimation of ASM at polymorphic loci and TM estimation at both polymorphic and nonpolymorphic loci. We restricted analysis to probes in regions with a CpG density of ≥2.5%. The CpG density for a given probe was calculated as the average of the CpG densities of the Nsp I and Sty I fragments containing the probe location. Nsp I and Sty I fragments that were not within the size-selected range of 100 to 2500 bp were excluded from the calculation of CpG density. The CpG density cutoff was chosen on the basis of preliminary analysis of the fully in vitro methylated control sample that determined that these regions allow for robust detection of methylation signals. With this filter, 7323 genes had at least one MBD-SNP TM probe within 5 kb upstream and 2 kb downstream of the transcription start site. Of these, 4295 genes had at least one MBD-SNP ASM probe within the same region.

MBD-SNP TM and ASM estimates. For a given sample, let $x_{iA}^E$ and $x_{iB}^E$ denote the enriched methylated fraction (E) signal intensity recorded at probe location i for alleles A and B, respectively. Similarly, $x_{iA}^T$ and $x_{iB}^T$ represent intensity values from the total input fraction (T) array. Taking the intensity ratio of enriched DNA to total DNA resulted in methylation estimates that are normalized for copy number and probe effects. ASM estimates were restricted to loci with heterozygous genotype calls.

The methylation signal is most directly assessed at non-polymorphic (copy number probe) loci, where it is given by $m_i = \log_2 x_i^E/x_i^T$. The nonpolymorphic probe signals are quantile-normalized between samples. Quantile normalization is typically inappropriate for methylation data because there can be significant differences in TM levels between samples. In this case, however, we take advantage of the fact that most of the probes on the array are in low-CpG density regions that are below the robust detection limit of the MBD assay. These probes, which dominate the signal distribution, are therefore expected to behave similarly across all samples in accordance with the quantile normalization assumption of equal between-sample signal intensity.

SNP loci methylation estimates are obtained by combining the signal from the two alleles: $m_i=\log_2[(x_{iA}^E+x_{iB}^E)/(x_{iA}^T+x_{iB}^T)]$. The polymorphic and nonpolymorphic probes are roughly evenly interspersed throughout the genome, and as a result, the methylation distributions of these two sets of probes are expected to be the same. We take advantage of this fact by quantile normalizing the polymorphic signal distribution to a target distribution defined by the nonpolymorphic probes, putting both types of probes on the same scale.

Probes on CpG-free restriction fragments were used as unmethylated control loci. As is common in many microarray applications, the unnormalized methylation values displayed a bias related to the probe GC content. This bias was corrected by adjusting values such that the GC-stratified, median control probe methylation value was set to zero.

The raw ASM signal at informative [heterozygous (A/B) genotype] loci was calculated as $\log_2[(x_{iA}^E/x_{iA}^T)/(x_{iB}^E/x_{iB}^T)]$. Because it is reasonable to assume that overall distribution of ASM is similar between samples, we quantile-normalized these ASM ratios. Because each SNP is represented by three replicate probes for the two alleles, the final SNP ASM ratio was calculated as the median of these ASM ratios.

Figure 26:
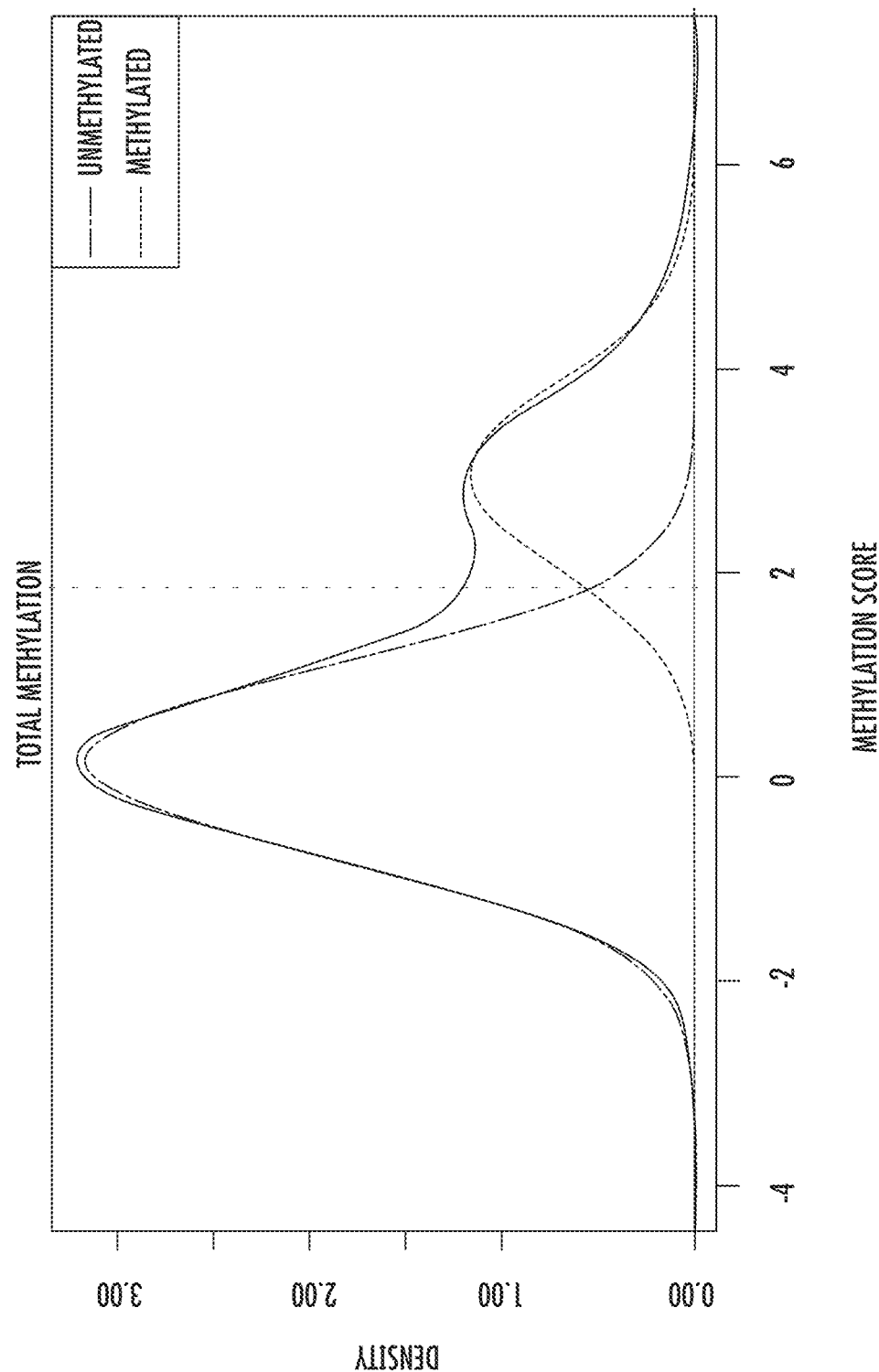
FIG. 26. Mixture model fit to the TM methylation score distribution. The mixture model was used to classify loci as methylated (right of the gray line) or unmethylated (left of the gray line).

Classification of MBD-SNP methylation status. The TM signal distribution had two clear modes, likely representing unmethylated and highly methylated loci, and could be modeled as a two-component normal mixture model (FIG. 26). This model was used to classify loci as methylated or unmethylated. ASM was similarly classified as being present or absent with a normal mixture model.

Identification of hyper-/hypomethylation and gain/loss of ASM. Hypermethylated loci were defined as being unmethylated in all organ donor normal samples and methylated in at least one prostate cancer metastasis. Hypomethylated loci were defined similarly, with all organ donor normal prostates showing methylation and at least one tumor showing lack of methylation. Regions of gain of ASM were defined as those that were classified as not having ASM in any of the organ donor normal prostate tissues and having ASM in at least one tumor sample. Regions of loss of ASM were defined as those that were classified as having ASM in all of the organ donor normal prostate tissues but classified as not having ASM in at least one tumor sample. To assess the number of alterations per subject, we restricted analysis to three randomly selected tumors per subject. This allowed comparison of number of alterations across subjects without bias to differences in the number of tumors available for a given subject.

Correlation analysis and hierarchical clustering by DNA methylation measures. Between-sample similarity was computed with the Pearson correlation coefficient. Average linkage Euclidean distance hierarchical clustering was carried out with 71 tissue samples from the 13 patient subjects with the 500 probes/probe sets with greatest variance across samples. Copy number had a minimal effect on methylation estimates because both TM and ASM estimates were calculated as the ratio of methylated DNA to total DNA. However, to exclude the possibility that observed methylation patterns were driven by residual copy number effects, we carried out a further two-step procedure before clustering. First, we restricted our analysis to probes in regions with a copy number of two as determined by Partek Genomic Suite (v6.4). Second, to account for any remaining subject-specific copy number variation, we fit probe-level models to adjust for continuous copy number estimates from CRLMM (v1.10.0).

Genotyping and copy number. Partek Genomic Suite (v6.4) was used to determine regions with gain or loss of copy number. The R/Bioconductor CRLMM package (v1.10.0) was used for genotyping and to generate raw (non-integer) copy number estimates.

Clonal maintenance R2. Loci with heterogeneous somatic alterations were identified by choosing probes with low variability among organ donor normal prostate samples (lowest 75%) but high variability among tumor samples (top 500 and top 5%). For copy number estimates, probes were excluded if the mean estimate among organ donor normal was outside the range (1.5 to 2.5). Methylation estimates with a single informative subject were excluded. Methylation estimates were adjusted for copy number effects, as described above in the "Correlation analysis and hierarchical clustering by DNA methylation measures" section. To quantify the fraction of ASM probes with R2 values comparable to copy number, we calculated the copy number mean R2 minus 1 SD and determined the fraction of ASM probes with an R2 value greater than this threshold.

Figure 15:
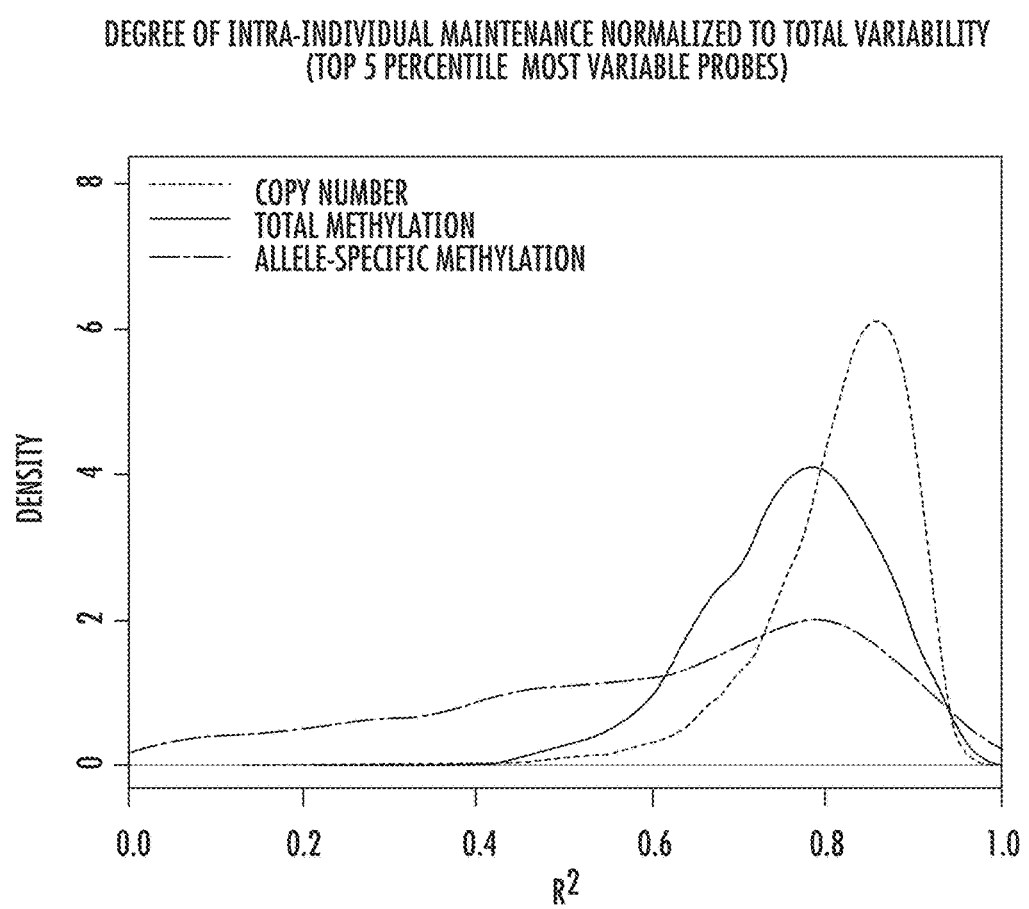
FIG. 15. Copy number, T M, and A SM distribution2 s using the top 5% most variable probes in each category. The distributions are nearly identical to those shown in FIG. 3A, in which the top 500 most variable probes were selected. This suggests that the results are not confounded by the large difference in the number of probes considered for each type of genome alteration.

To ensure that the difference in number of probes available for copy number (1,852,215) and TM (51,501) did not drive the observed similarity in maintenance, we repeated the analysis using the top 5% most variable probes and obtained the same result (FIG. 15). To exclude the possibility that the observed difference in R2 between hypermethylated and hypomethylated loci is related to differences in variability between large and small methylation log ratios, we discretized methylation values into unmethylated, partially methylated, or fully methylated categories. R2 values calculated with discretized methylation were very similar to those obtained from continuous methylation estimates.

Gene expression microarray data and analysis of correlation between DNA methylation and gene expression. Samples used for gene expression profiling included 18 metastases from five autopsy subjects, processed as described previously (16), and 21 normal prostate specimens from organ donors (54). Total RNA was extracted from cryostat sections and evaluated with the Agilent 2100 Bioanalyzer (Agilent Technologies) as described previously (55). Gene expression profiling was performed according to the guidelines provided by the Agilent Whole Genome Expression Microarray system (Agilent Technologies). Briefly, each of the 39 RNA samples was linearly amplified and labeled with Cy5, and cohybridized with a common reference RNA sample derived from benign prostatic hyperplasia that was similarly amplified but labeled with Cy3. For each sample, expression ratios of Cy5/Cy3 for each probe constituted the raw gene expression measure for the corresponding gene. Raw data were preprocessed with the R/Bioconductor limma package using within-sample standard locally weighted least squares regression (lowess) normalization and between-sample quantile normalization. Values from replicate probes were averaged. The raw and normalized data are available from the Gene Expression Omnibus (GEO) with accession number GSE38241. Probes differentially expressed between prostate cancer metastases and normal prostate tissues were identified by a linear mixed-effects model that accounts for within-subject correlation between tumor samples. The top 500 most variably expressed probes across all tissues were identified and subjected to average linkage Euclidean distance hierarchical clustering. For correlation analysis between DNA methylation and gene expression, methylation probes were assigned to genes if they were located within a 5-kb upstream to 2-kb downstream window around transcriptional start sites. In the case where multiple methylation probes were available for a given gene, one was selected at random. Gene-level linear regression models were used to assess statistical significance of the expression-methylation relationship. When assessing the strength of the intraindividual gene expression-methylation relationship, a subject specific term was added to the model. R2 values for log 2 gene expression values were calculated as described for DNA methylation.

DNA methylation cityscapes. Genomic cityscape plots were created to display regions with altered TM or ASM in the metastatic prostate cancer tissues compared to the organ donor normal prostate tissues. Within each cityscape, genomic loci were folded into neighborhoods in order of chromosomes along a Hilbert curve (39). Each address in the cityscape generally represents a single region of the genome that was interrogatable by the MBD-SNP approach. In rare circumstances, the position of adjacent structures was swapped when this improved visibility of a labeled structure. Because of dimensional constraints on the Hilbert curve layout, some addresses represent the maximal signal from two adjacent genomic loci. Each structure in the cityscape represents a region in which all of the organ donor normal prostate specimens conformed to the appropriate base state (for example, all classified as unmethylated for the hypermethylation cityscape or all classified as methylated for the hypomethylation cityscape), and at least one metastasis was altered in methylation state compared to the base state. The height of each structure in the cityscape indicates the fraction of tumors with a DNA methylation alteration. The tallest structures thus represent loci at which 100% of all tumors were classified as methylated and none of the organ donors were methylated (for example, GSTP1 in the hypermethylation cityscape). The color of each structure represents the somatic alteration maintenance metric (R2). In general, when multiple promoter-associated probes were available, all were used for plotting, but only the one with highest alteration frequency was labeled. In the case where multiple probes show the same alteration frequency, the one with the highest R2 was selected for labeling. For example, in the cityscape, all probes for GSTP1 are plotted, but only the probe showing the highest frequency (SNP A-4242162) is labeled as GSTP1. Cityscape plots were created with the Processing programming language.

Analysis software. R 2.14 (56), Bioconductor 2.8 (57), and Partek Genomic Suite 6.4 were used for all analyses. All code is available upon request.

Supplementary Materials and Methods

Figure 1B:
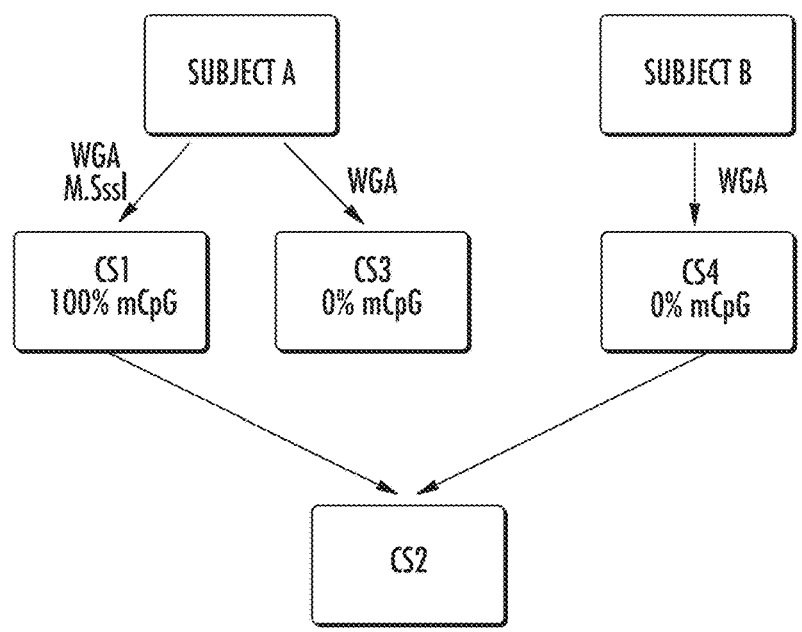

Validation of MBD-SNP methylation assay performance.
Validation using control samples with known methylation profiles. ROC curves were generated using a set of four control samples, denoted CS1-CS4, with known methylation levels (FIG. 1B). CS3 and CS4 were generated by taking 10 ng of normal human male genomic DNA from Subject A and Subject B respectively, and subjecting each to whole genome amplification using the Genomiphi DNA amplification kit according to the manufacturer's protocols (GE Healthcare). To prepare CS1, a portion of CS3 was completely methylated at all CpG dinucleotides using the M. SssI methyltransferase according to the manufacturer's instructions (New England Biolabs). CS2 was prepared by mixing a portion of CS1 and CS4 in a 1:1 ratio. Each control sample, CS1-CS4, was subjected to the entire MBD-SNP assay protocol. For total methylation, the ROC curve was generated by comparing total methylation estimates from the fully methylated sample (CS1) to the fully unmethylated sample (CS3). The allele-specific methylation (ASM) ROC curve is based on ASM estimates from the CS2 sample, generated by a 1:1 mix of a fully methylated (CS1) and a fully unmethylated (CS4) sample, giving a set of loci with known ASM status. Loci with genotype A1A1/B2B2 (i.e. genotype AA in the fully methylated sample, and BB in the fully unmethylated sample) comprised the ASM set. Loci with genotype A1B1/A2B2 comprised the lack-of-ASM set.

Validation by real-time methylation-specific PCR (RT-MSP). We previously determined the methylation status of 5 genes (MLH1, ESR1, EDNRB, APC and ABCB1) across 44 samples used in the current study by real-time methylation-specific PCR (RT-MSP), as reported previously (19). FIG. 1D shows the receiver operator characteristic curve (ROC) for MBDSNP methylation estimates at loci determined by RT-MSP as being either methylated or unmethylated (AUC=91%).

Figure 18:
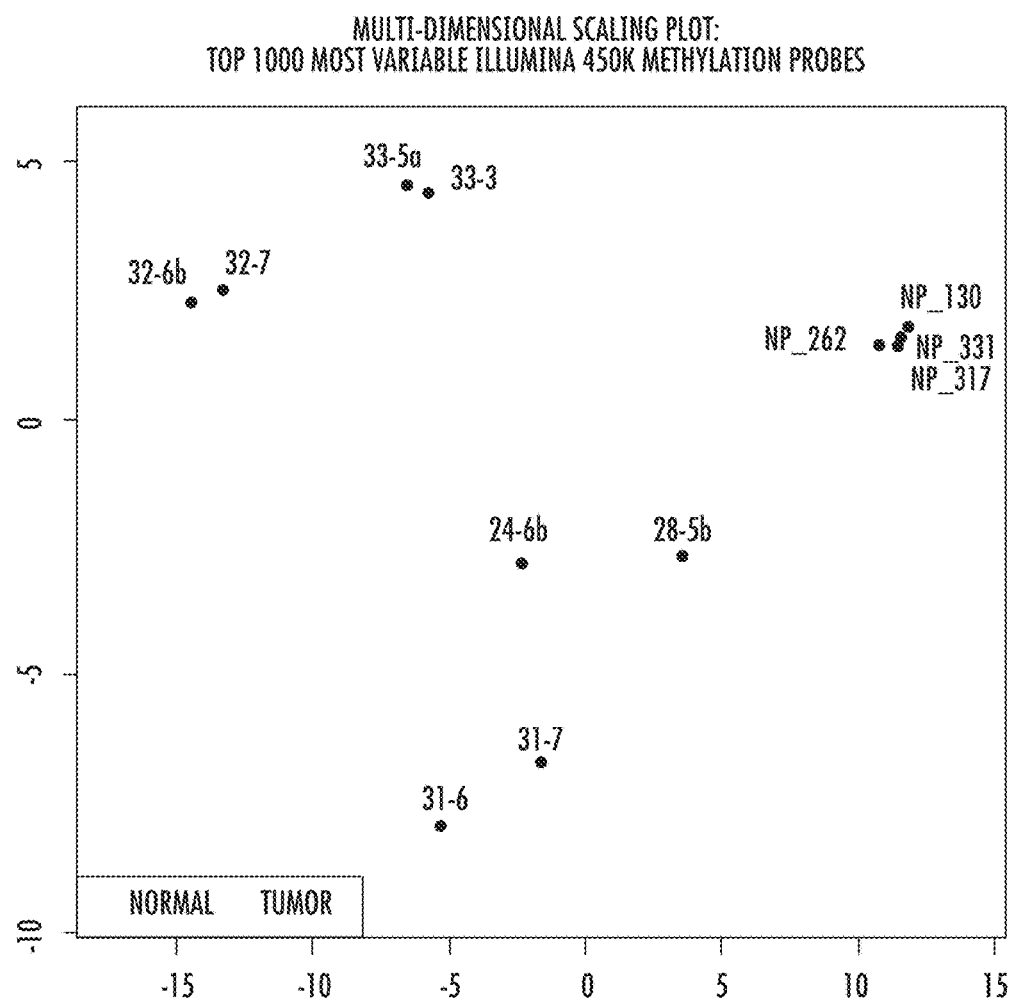
FIG. 18. Multidimensional scaling plot of DNA methylation profiles of eight prostate tumors (red) from five individuals and four benign prostate specimens (green) analyzed on the Illumina HumanMethylation 450 k microarray. The first two digits of the tumor labels represent the subject ID. Consistent with findings from the MBD-SNP platform, benign tissues from different individuals have considerably less heterogeneous methylation profiles than tumors from different individuals. In addition, tumors from the same individual are highly similar, relative to the large between-individual differences.

Validation by the Illumina HumanMethylation 450 k platform. We carried out bisulfate conversion-based validation assays on a subset of our study samples, including 8 metastases and 4 normal prostate specimens using the Illumina HumanMethylation 450 k platform. Raw data was preprocessed with the R/Bioconductor minfi package without background subtraction and with the Illumina scale normalization option. The raw and normalized data is available from the Gene Expression Omnibus (GEO) with accession number GSE38240. 13,426 MBD-SNP probes are located within 150 bp of an Illumina 450 k probe and could therefore be compared using this independent assay. Among the sites classified as highly methylated (Methylation Beta-value>0.8) or unmethylated (Methylation Beta-value<0.2) by the 450 k platform, 86.9% were concordant by MBD-SNP (FIG. 1E). In addition, we examined whether some of the conclusions from the MBD-SNP platform could be verified using the independent Illumina 450 k validation platform. A multi-dimensional scaling analysis showing correlation between samples on the Illumina 450 k replication platform recapitulates the dual findings of a high degree of similarity between normal prostate specimens from different people, and high clonal maintenance across metastases from the same person (FIG. 18). Taken together, these analyses validate both the individual sample-by-sample and gene-by-gene findings and also the overall conclusions using an entirely independent methodology. We note that this platform is not a replacement for the MBD-SNP approach since it does not allow measurement of allele-specific methylation and copy number analysis in the same platform.

Figure 16:
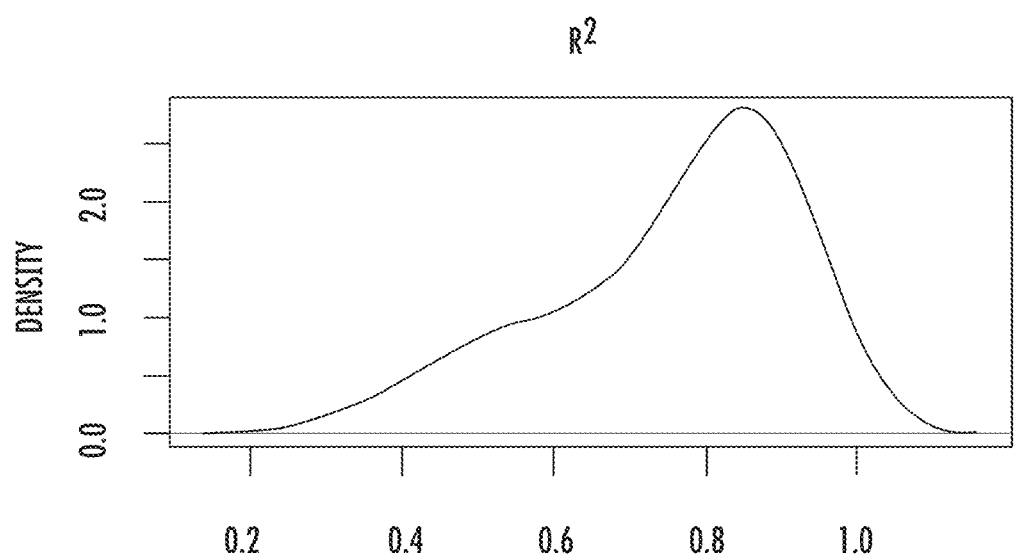
FIG. 16. Methylation R2 for the 44 MBD-SNP probes whose somatic hypermethylation status was verified in an independent dataset from Kobayashi et al Data was obtained from the Gene Expression Omnibus (Accession #GSE26126). (5 8).
Figure 17:
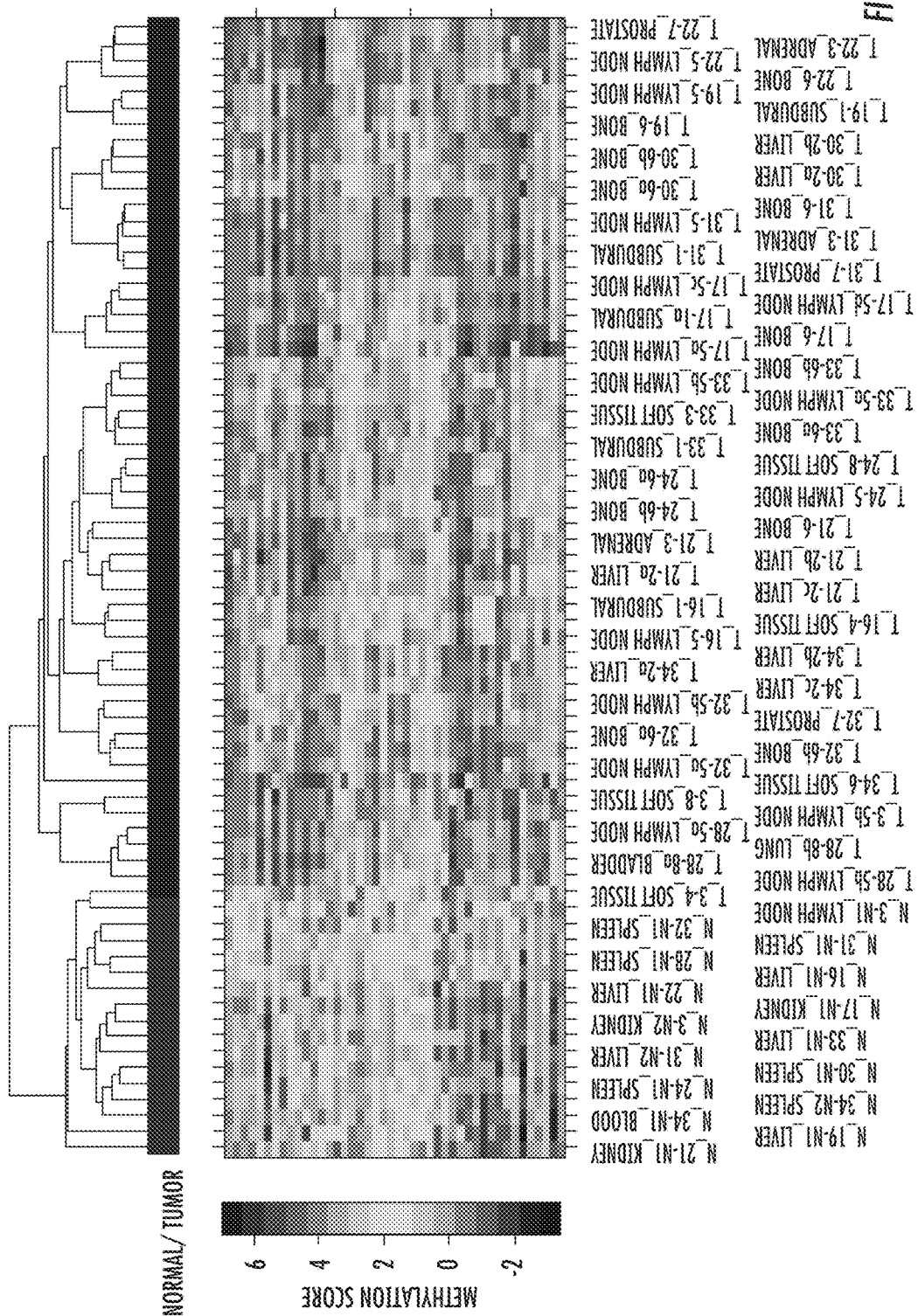
FIG. 17. DNA methylation hierarchical clustering showing high within-subject similarity and between-subject heterogeneity of metastases. These analyses were done on the subset of 44 MBD-SNP probes whose somatic hypermethylation status was verified in an independent dataset from Kobayashi et al. (Genome Res. 2011 July; 21(7):1017-27, GEO accession #GSE26126).

Validation of DNA methylation alterations in an independent study of primary prostate cancer and matched normal tissues. We sought to validate our somatic DNA methylation alteration findings through examination of an independent prostate cancer/normal DNA methylation dataset. Kobayashi et al. (58) profiled DNA methylation in matched tumor-normal prostate specimen pairs from 70 subjects using the Illumina 27 k Methylation Microarray platform (GEO accession #GSE26126). We identified 801 MBD-SNP probes that are located within 150 bp of an Illumina 27 k array probe and examined concordance between the studies. Of the 51 regions that we identified as hypermethylated in >50% of tumors by MDB-SNP, 44 (86%) showed statistically significant hypermethylation (p<0.05) in this independent dataset. As the validation data are from a matched tumor and adjacent benign tissue study design, the high concordance confirms that our findings represent true tumor-associated somatic alterations, and not simply a reflection of changes occurring with age or in tumor-adjacent benign tissues. We further observed a high degree of concordance in the functional annotation of hyper- and hypo-methylated promoter regions identified in the two studies. All NCI Cancer Gene Index Gene sets identified as significantly hypermethylated in our study were similarly significant in the Kobayashi et al data, as were 14 of the 17 development-associated Gene Ontology categories we identified as significantly enriched for hypermethylation. Conversely, and consistent with our results, the hypomethylated regions identified by Kobayashi et al. showed no enrichment for developmentally related gene sets. Additionally, the high degree of within-subject maintenance of DNA methylation patterns relative to between-subject and overall variability was also observed when subsetting to the 44 regions that could be verified as somatically hypermethylated in the Kobayashi et al. dataset (FIG. 16, S12). Therefore, the results from our study could be broadly validated using an independent prostate cancer DNA methylation dataset collected using a bisulfate-based microarray assay platform, thus indicating that the findings here are not simply attributable to study design- and platform-specific artifacts.

Genome annotation and assessment of enrichment of annotations. HG18 Refseq gene and CpG island track data were downloaded from the UCSC Table Browser on Feb. 15, 2011 and used to annotate probe locations. Probes in hypermethylated and hypomethylated regions were assessed for enrichment of overlap with CpG islands, CpG island shores (defined as 2 kbp upstream or downstream of CpG islands), promoters, introns, exons, and intergenic regions, by using the Fisher exact test.

Gene Set Analysis. The gene sets assessed included Gene Ontology categories (25), the Memorial Sloan Kettering prostate cancer pathway gene set (26) and gene sets from the NCI Cancer Gene Index (27). Genes were classified as somatically altered if there was an altered probe locus within the region 5 kb upstream to 2 kb downstream of the transcriptional start site. Loci were ranked by frequency of methylation or R2 and the Wilcoxon rank sum statistic was used to assess gene set enrichment among highly ranked genes. In order to reduce the dependence of the maintenance R2 metric on methylation frequency, we also examined a standardized metric calculated by subtracting the mean and dividing by the standard deviation within frequency bins. We verified that our results were robust to alternative promoter region definitions by repeating our hypermethylated gene set analysis with a region size of 2 kb upstream to 0 bp downstream of the TSS and confirming that our conclusions were unaffected.

Similarity of copy number and methylation clonal evolution patterns. Evidence for co-evolution of somatic copy number and methylation alterations is provided by examination of hierarchical clustering dendrograms. For each of the 13 subjects we identified the 500 most variable probes and performed average linkage hierarchical clustering of samples from that subject. The procedure was carried out for both copy number and total methylation data. In the case of copy number, we used probes where the normal samples exhibited a continuous copy number estimate within the range (1.5, 2.5), and in the lowest quartile of variance. To identify methylation effects independent of copy number, we excluded probes where a subject's samples had a copy number state other than 2. In addition, we corrected for residual copy number effects as described in the section "Hierarchical clustering by methylation status". We defined a metric of clustering similarity as the number of agglomeration events where the members of the two groups are identical between the copy number and methylation dendrogram: $S=\Sigma_i \Sigma_j I_{i,j}$ where i=1 ... 13 indexes subject, and j indexes the branch points in subject i's copy number dendrogram. $I_{i,j}$ is 1 if the same agglomeration exists in the subject's methylation dendrogram, and zero otherwise. An empirical p-value was obtained by comparing the statistic, S, to a null distribution generated by permuting sample labels and repeating the above procedure 10,000 times.

Identification of regions showing recurrent, intra-individual, metastatic-tumor heterogeneity in DNA methylation patterns. To identify regions of intra-individual, metastatic-tumor heterogeneity, we assessed the within-subject tumor methylation standard deviation normalized to the variation across all benign prostate samples studied, for each subject (n=13) at each locus that was either hypermethylated (n=3,943) or hypomethylated (n=22,267) in at least one subject. Levene's test, a robust statistical test for inequality in variances, was used to test whether the variance of methylation across each subject's metastases was greater than the variance observed among benign prostate specimens. Subjects were putatively classified as showing intra-individual metastatic-tumor heterogeneity at a given locus if: i) the Levene's test was significant at FDR=5%, and ii) the subject had at least one metastasis that showed evidence of methylation and at least one metastasis that showed evidence of lack of methylation at that locus. This resulted in identification of 512 hypermethylation and 4874 hypomethylation loci meeting these criteria for intra-individual metastatic tumor heterogeneity in at least one subject. We then identified those loci with evidence for recurrent intra-individual metastatic tumor heterogeneity in at least 2 subjects. Gene Ontology Gene Set enrichment analysis was carried out using the Wilcoxon rank sum test, after ranking genes by the number of individuals that displayed heterogeneity at the promoter locus.

Results

Performance of the MBD-SNP approach. We developed and applied a new technology and associated computational methods enabling simultaneous genome-scale analysis of genetic (copy number) and epigenetic (TM and ASM) alterations. This method, called MBD-SNP (see FIG. 1A for overview), features affinity enrichment of methylated genomic DNA fragments (13) using the methyl-binding domain polypeptide from the MBD2 protein (MBD2-MBD), which was previously shown to preferentially bind methylated DNA with >100-fold selectivity compared to unmethylated DNA (14, 15). The resulting library of methylated DNA fragments and an unenriched total input fraction from the same specimen were then processed and hybridized to Affymetrix SNP 6.0 high-density oligonucleotide microarrays. Comparison of the enriched methylated fraction with the total input using new statistical approaches allowed parallel genome-scale assessment of TM, ASM, and copy number in a rapid and cost-effective manner.

Figure 1C:
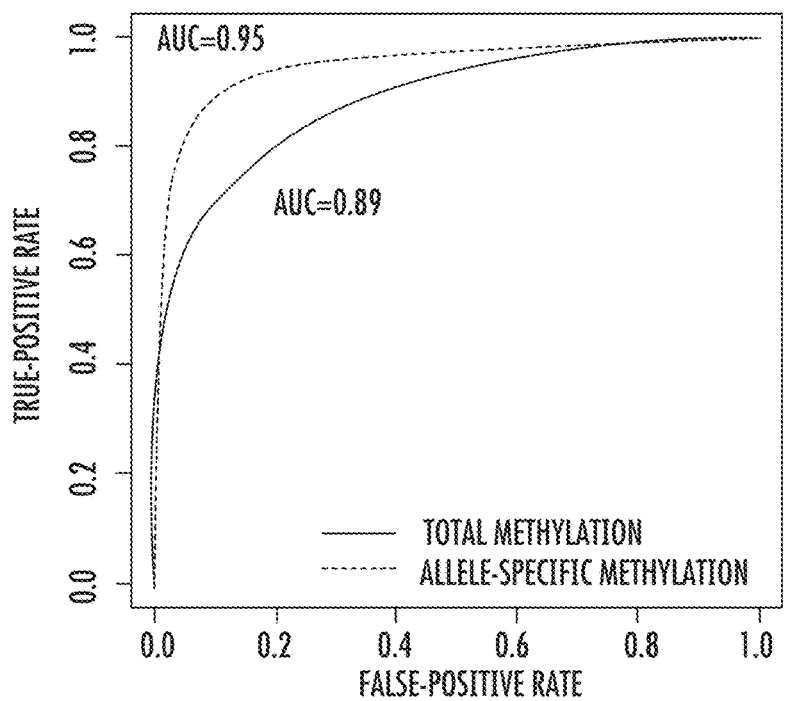
Figure 1D:
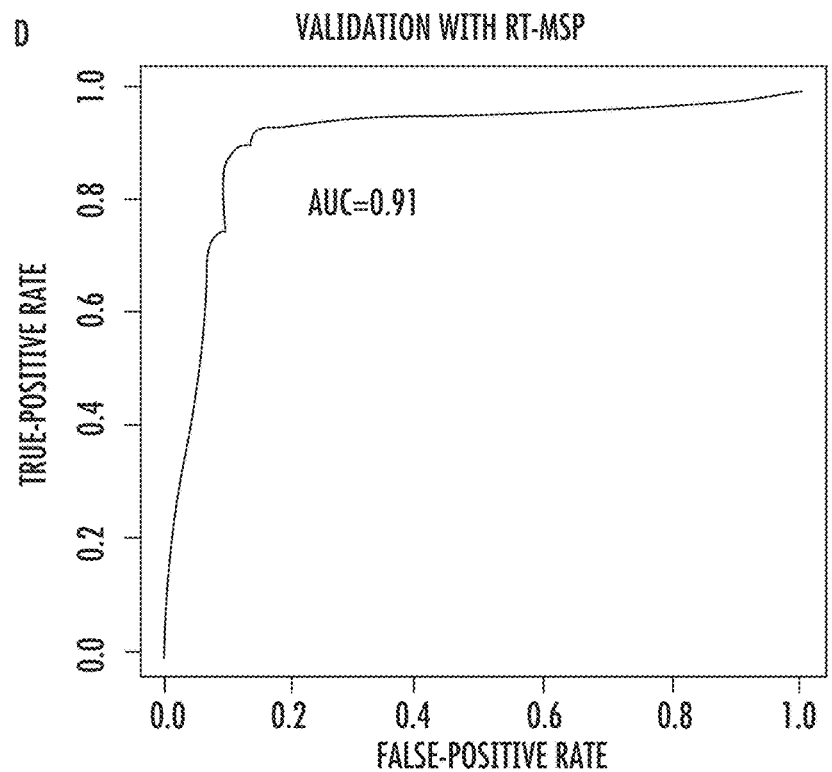
Figure 1E:
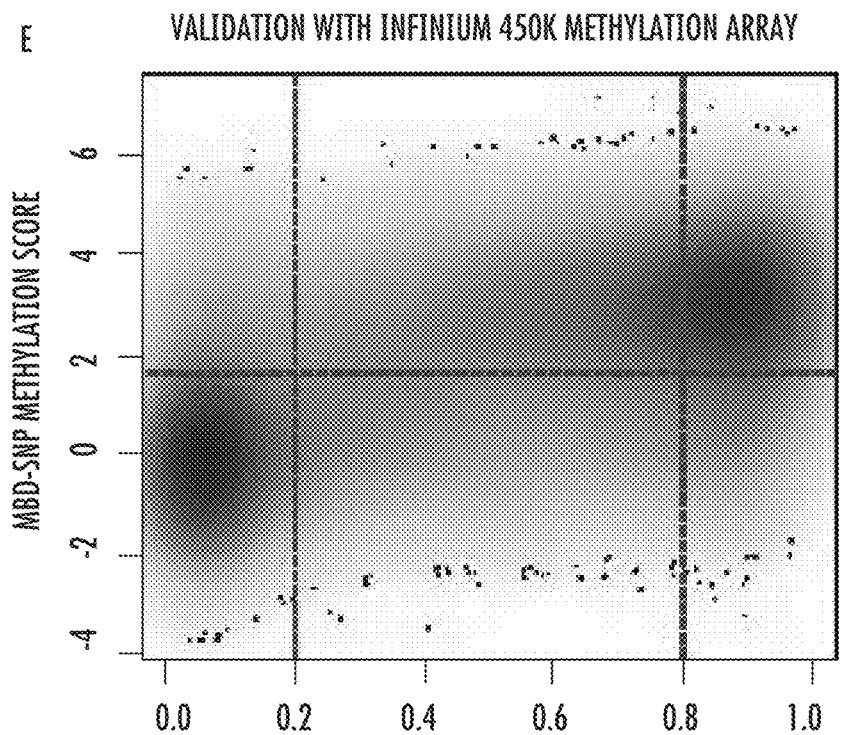
Figure 6:
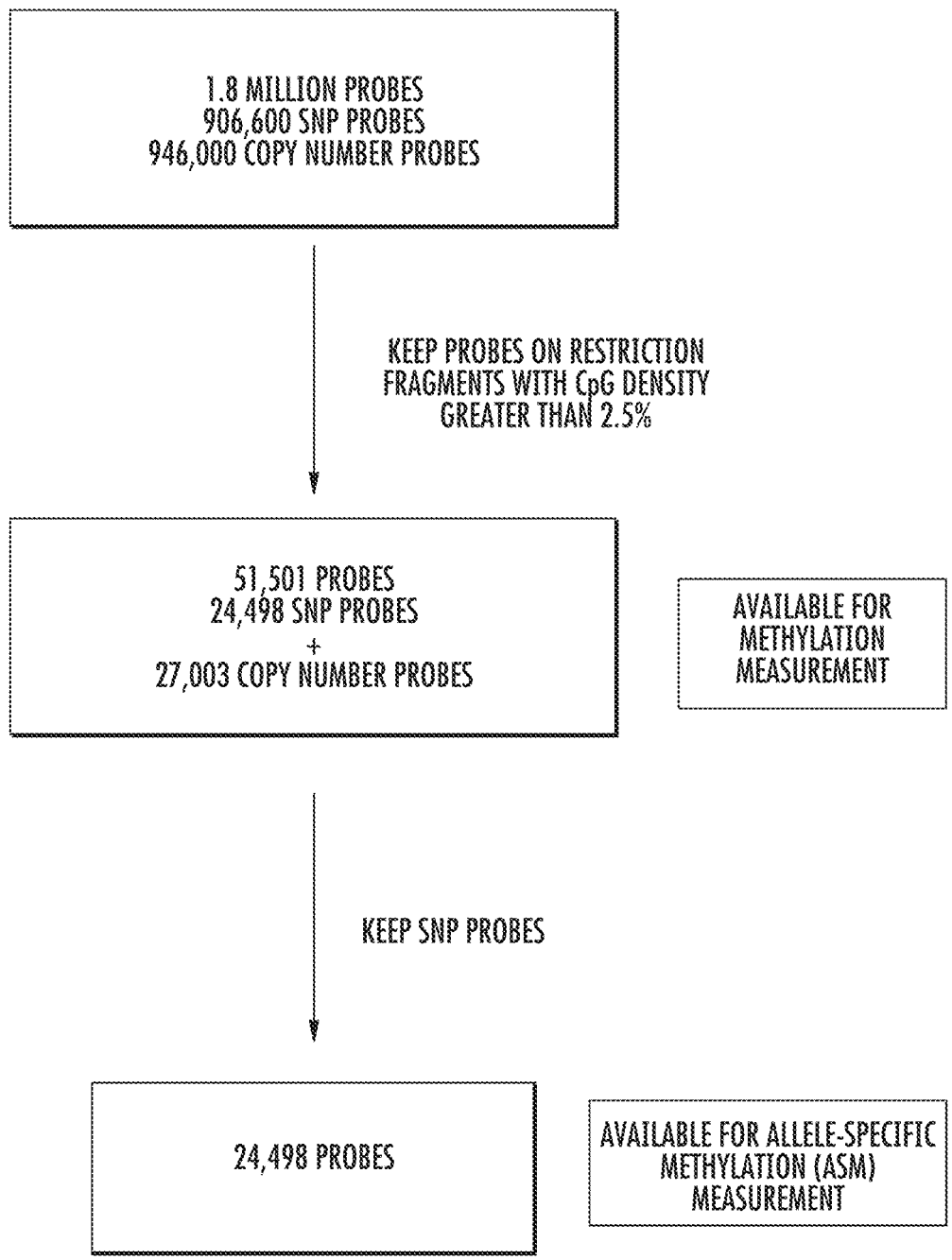
FIG. 6. Filtering procedure used to select MBD-SNP probes. Of the 1.8 million probes on the Affymetrix SNP 6 microarray, 51,501 are in regions with a CpG density greater than 2.5% (the detection threshold for the MBD-SNP assay). These comprise 24,498 SNP probes and 27,003 copy number probes, all of which can be used to assess total methylation. In addition, the SNP probes also provide estimates of allele-specific methylation.

Using a series of control specimens (FIG. 1B and SupplementaryMaterials and Methods), we determined that the MBD-SNP technology allowed accurate point estimates of TM [FIG. 1C, area under the receiver operator characteristic curve (AUC)=0.89] and ASM (FIG. 1C, AUC=0.95) for regions of the genome with ≥2.5% CpG density. Therefore, this platform allowed accurate interrogation of TM and ASM patterns at 51,501 (TM) and 24,498 (ASM) regions (FIG. 6), including 7323 (TM) and 4295 (ASM) gene promoter regions, 5766 (TM) and 4277 (ASM) CpG islands (CGIs), and 15,210 (TM) and 9969 (ASM) CGI shores (table S1).

Somatic alterations in TM and ASM patterns in lethal metastatic prostate cancer. Previous studies have used analysis of genetic alterations to examine the clonal evolution of cancer metastases (16-18). Using such a study design, featuring analysis of multiple metastatic deposits as well as matched normal tissues from each subject from a lethal metastatic prostate cancer rapid autopsy cohort, Liu et al. showed that prostate cancer metastases within an individual have monoclonal origins and display subsequent clonal evolution (16). We examined the same specimens from this rapid autopsy cohort (a total of 71 specimens, including 3 to 6 metastases and 1 to 2 normal tissues from each of 13 subjects) to understand whether DNA methylation alterations also showed clonal maintenance and evolution across metastatic dissemination. Additionally, we examined 24 normal prostate tissues from organ donors without evidence of prostate disease as reference samples.

Figure 7:
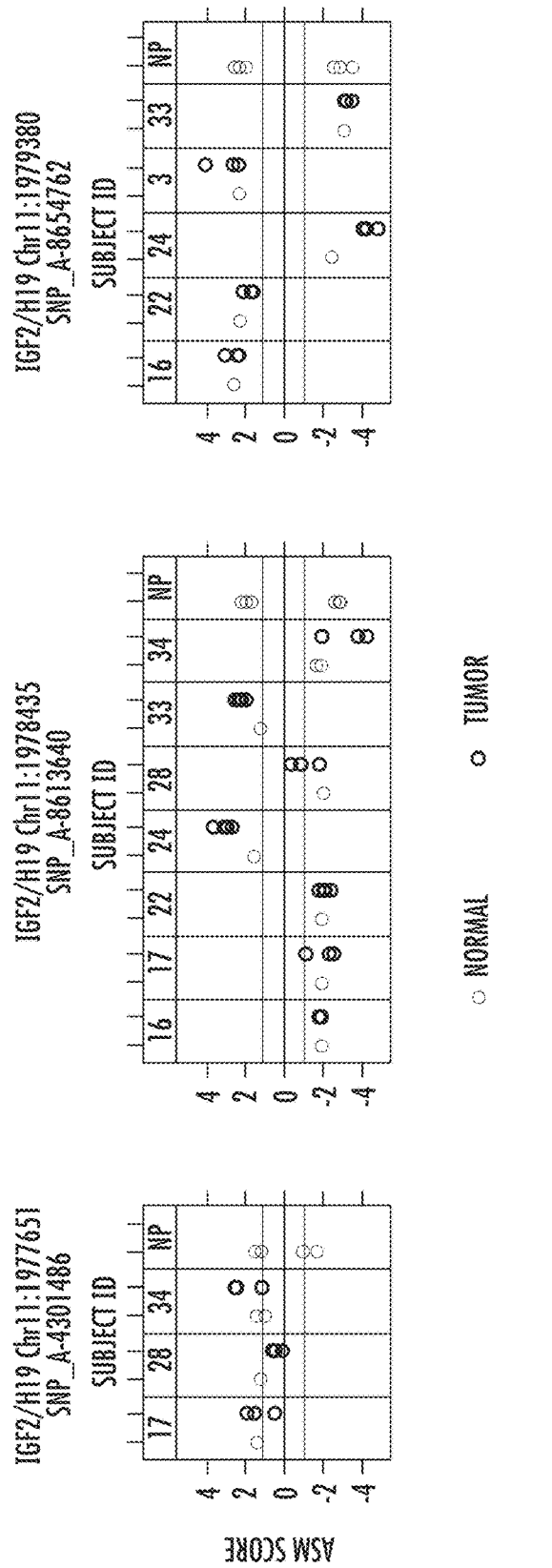
FIG. 7. ASM and loss of ASM at the IGF2/H19 locus. Three regions from the IGF2/H19 locus, close to known differentially methylated imprinting control regions (DMRs), are shown. Note that nearly all normal tissues including normal prostate tissues and subject-matched normal tissues, showed allele-specific methylation, denoted by ASM scores that are greater than the upper gray line, or below the lower gray line. Some of the tumors show evidence of loss of allele-specific methylation at these loci, consistent with loss of imprinting, denoted by ASM scores falling between the two gray lines. Organ donor normal prostate tissues are denoted by NP.
Figure 8:
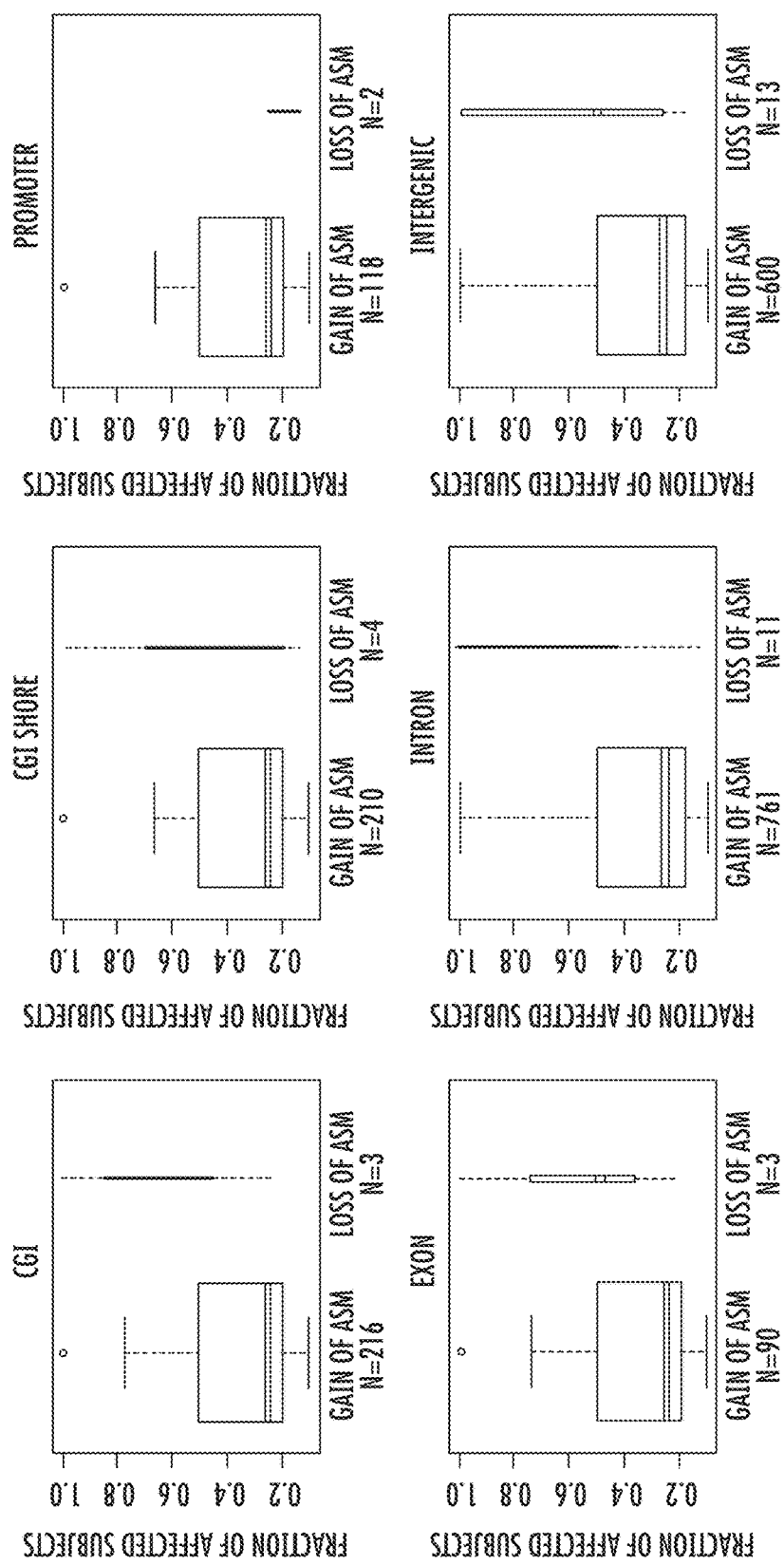
FIG. 8. Number of subjects affected by gains or losses of ASM falling within various genome annotations. The width of the box-and-whisker plots is proportional to the number of regions in the distribution. The top and bottom edges of the box represent the 75th and 25th percentile of the distribution, with the line inside the box representing the median. The ends of the whiskers represent the 5th and 95th percentiles. The relatively small number of loss-of-ASM compared gain-of-ASM alterations is largely due to the small number of regions that met stringent criteria for ASM in all prostate normal tissues (N=54 probes).
Figure 9:
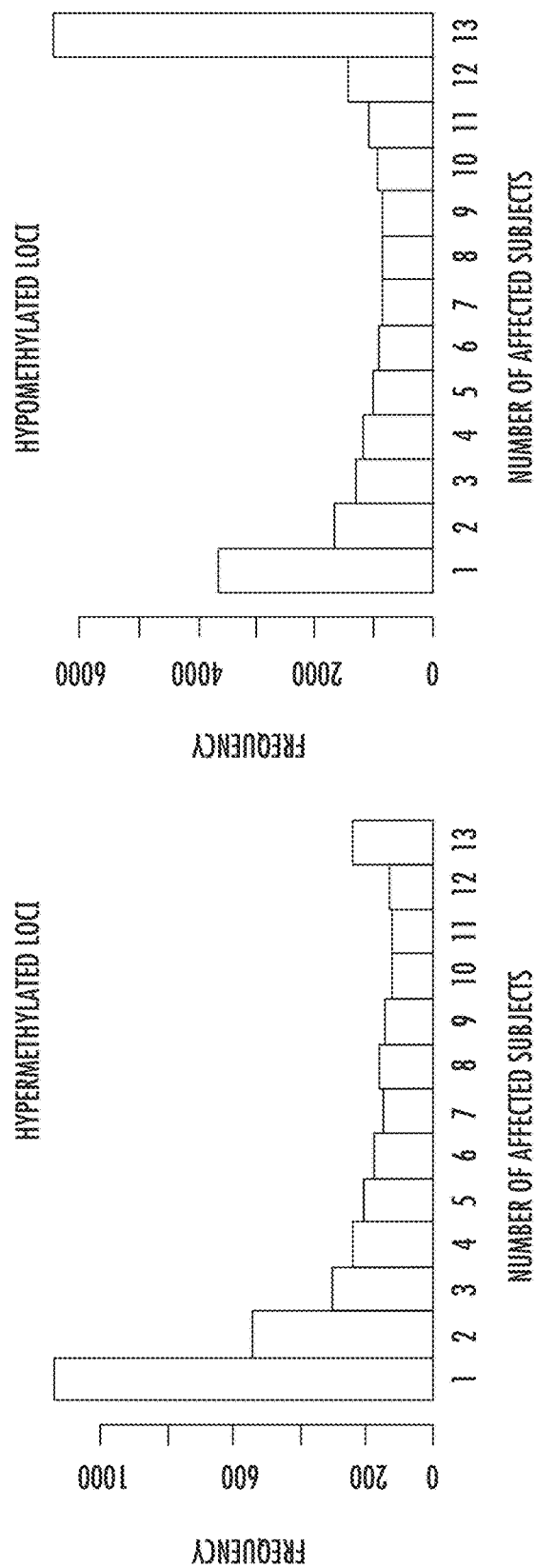
FIG. 9. Number of regions showing DNA methylation alterations stratified by number of affected subjects. Regions are classified as hypermethylated if they are unmethylated in all normal samples, but methylated in at least one tumor. Similarly, regions are classified as hypomethylated if they are methylated in all normal samples, but unmethylated in at least one tumor.
Figure 10:
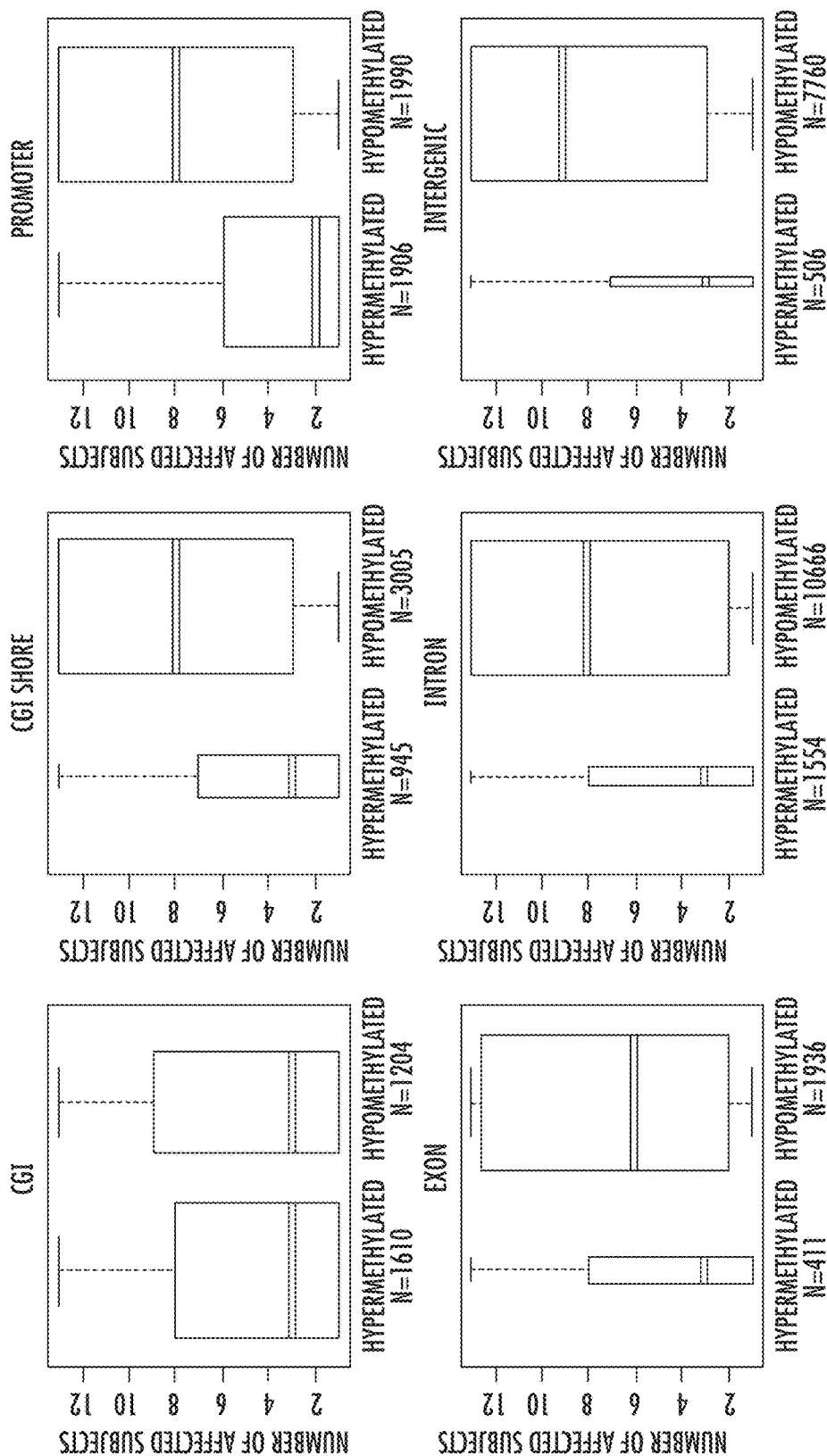
FIG. 10. Distribution of number of subjects showing alteration of a given region, stratified by genome annotation. The width of the box-and-whisker plots is proportional to the number of regions in the distribution. The top and bottom edges of the box represent the 75th and 25th percentile of the distribution, with the line inside the box representing the median. The ends of the whiskers represent the 5th and 95th percentiles.

Applying the MBD-SNP technology and our new computational approaches to the study samples, we computed normalized TM and ASM scores at all informative regions. We confirmed that the approach allowed highly accurate point estimates of TM across the study samples by validating the data in a subset of the study samples using both RTMSP [real-time methylation-specific polymerase chain reaction (PCR)] assays (19) and the bisulfite-based Illumina HumanMethylation 450k microarray platform (FIG. 1, D and E, and Supplementary Materials and Methods). To assess the ability to identify regions showing ASM across the study samples, we examined ASM signals at known imprinted loci including multiple known allele-specific differentially methylated regions at the IGF2/H19 imprinting control regions. The MBD-SNP-derived ASM scores were consistent with imprinting of these regions in all normal samples analyzed (FIG. 7). Some cancer specimens showed evidence for somatic loss of ASM of these regions, consistent with cancer specific IGF2/H19 loss of imprinting, a known hallmark of many cancers including prostate cancer (20, 21). We observed 1873 regions that showed gain or loss of ASM in at least one tumor compared to normal tissues (table S2 and FIG. 8), with 667 of these showing alterations in at least two subjects.

Figure 11A:
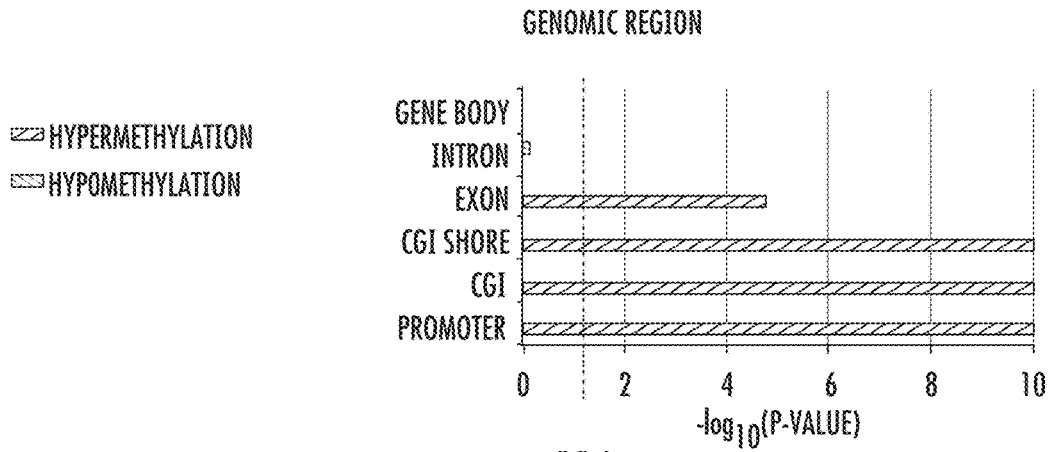
FIG. 11A-11C. Gene set enrichment analysis of hyper- and hypomethylated loci. 6,108 promoter loci were ranked by frequency of hyper- (blue) or hypo- (red) methylation. The Wilcoxon rank sum test was used to assess enrichment of various genome annotations (top). Probes in promoter regions were used to assess gene set enrichment of Memorial Sloan Kettering Prostate Cancer Pathways Gene Set, the NCI Cancer Gene Index (middle) and Gene Ontology (bottom) gene sets. Gene ontology gene sets with a false discovery rate q-value of less than 0.01 are shown. Dashed line indicates p/q=0.05.
Figure 11B:
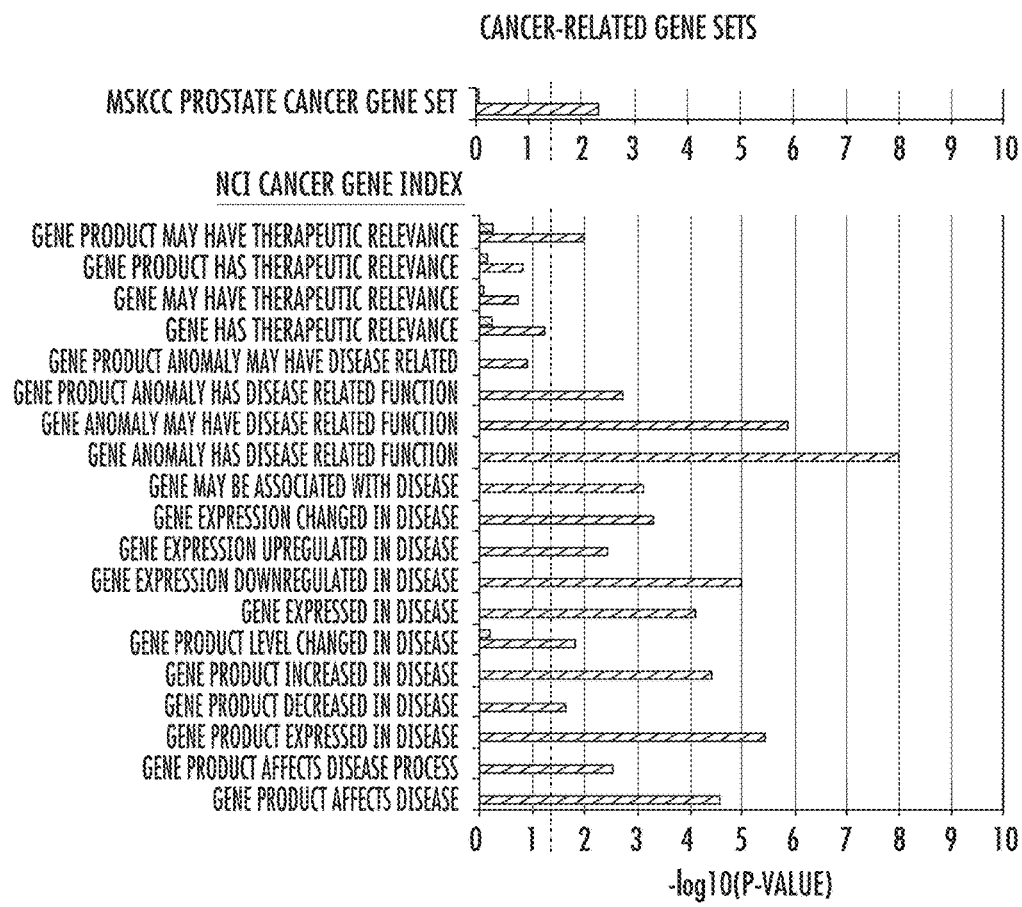
Figure 11C:
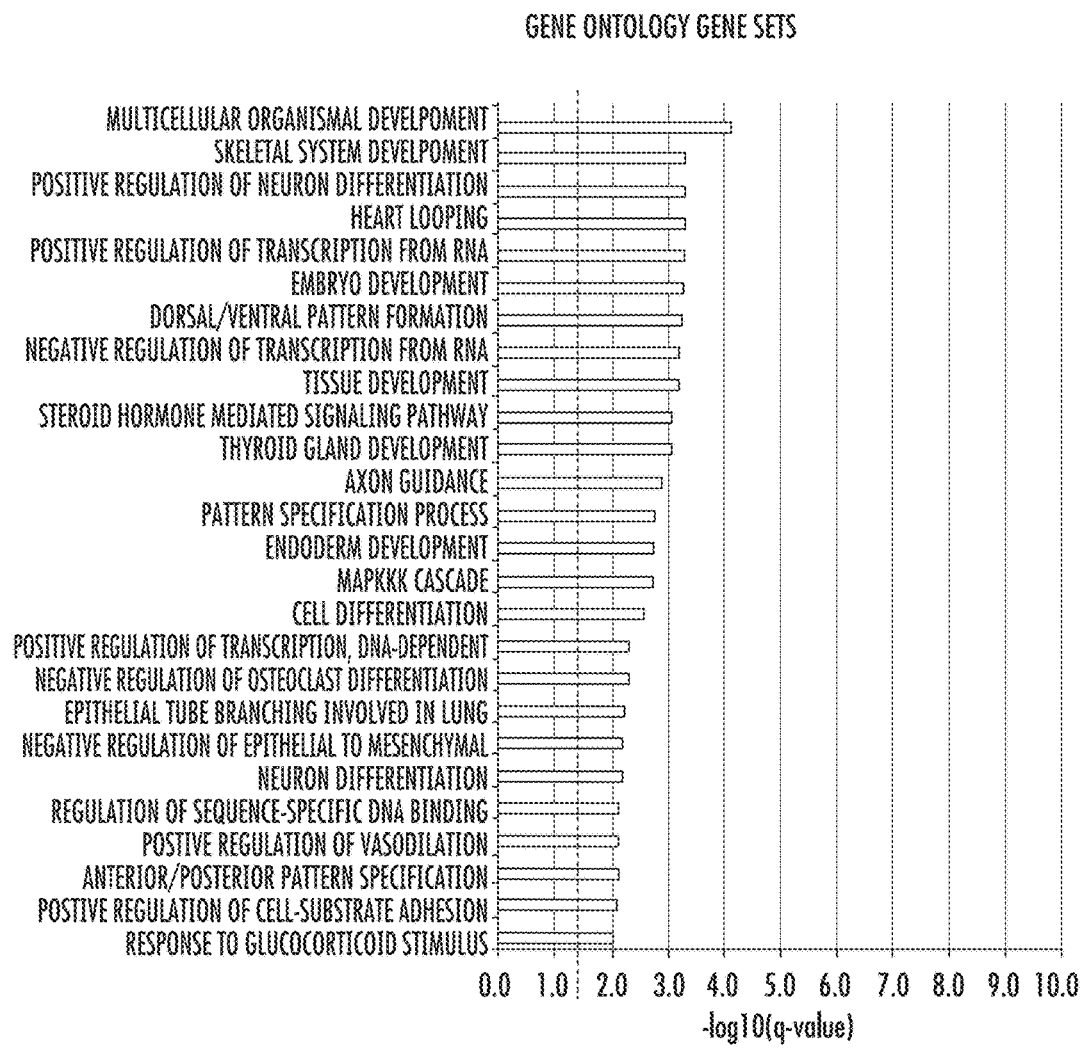
Figure 12:
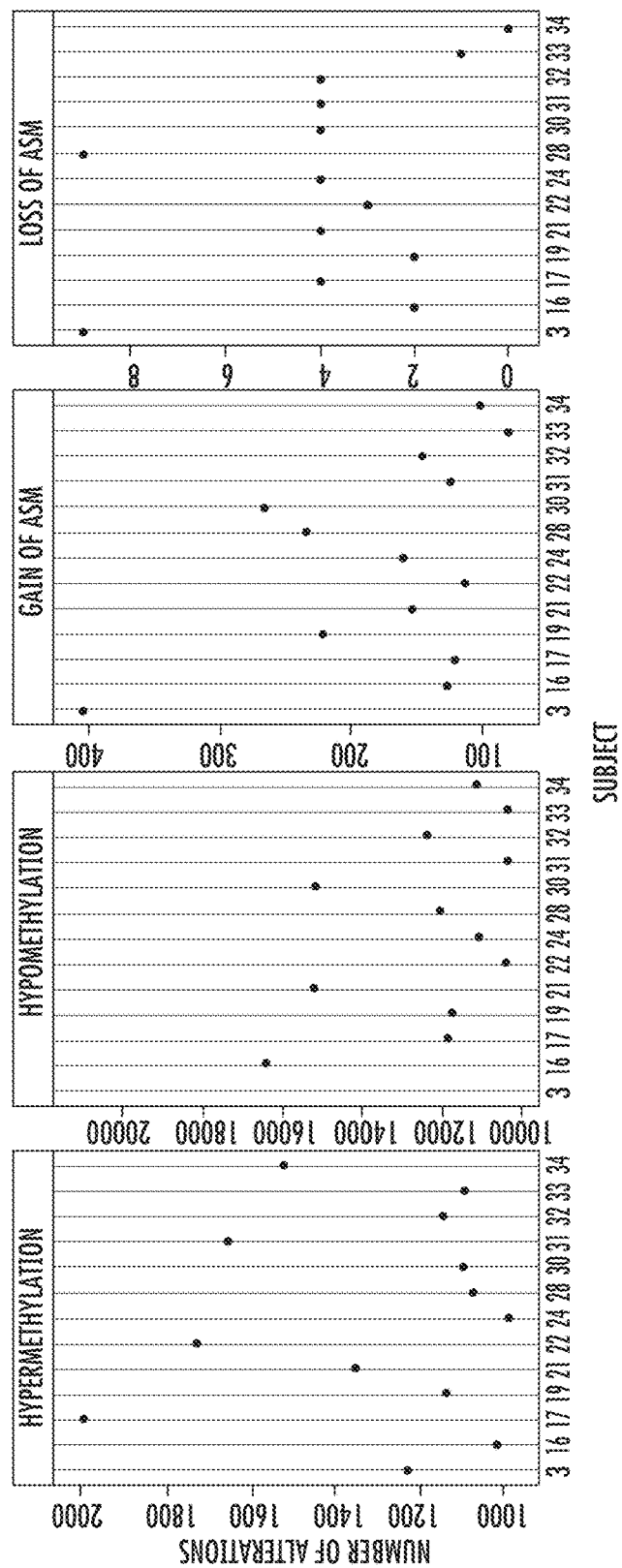
FIG. 12. Number of DNA methylation alterations in each subject. The number of alterations identified in each of the 13 subjects is shown.
Figure 13:
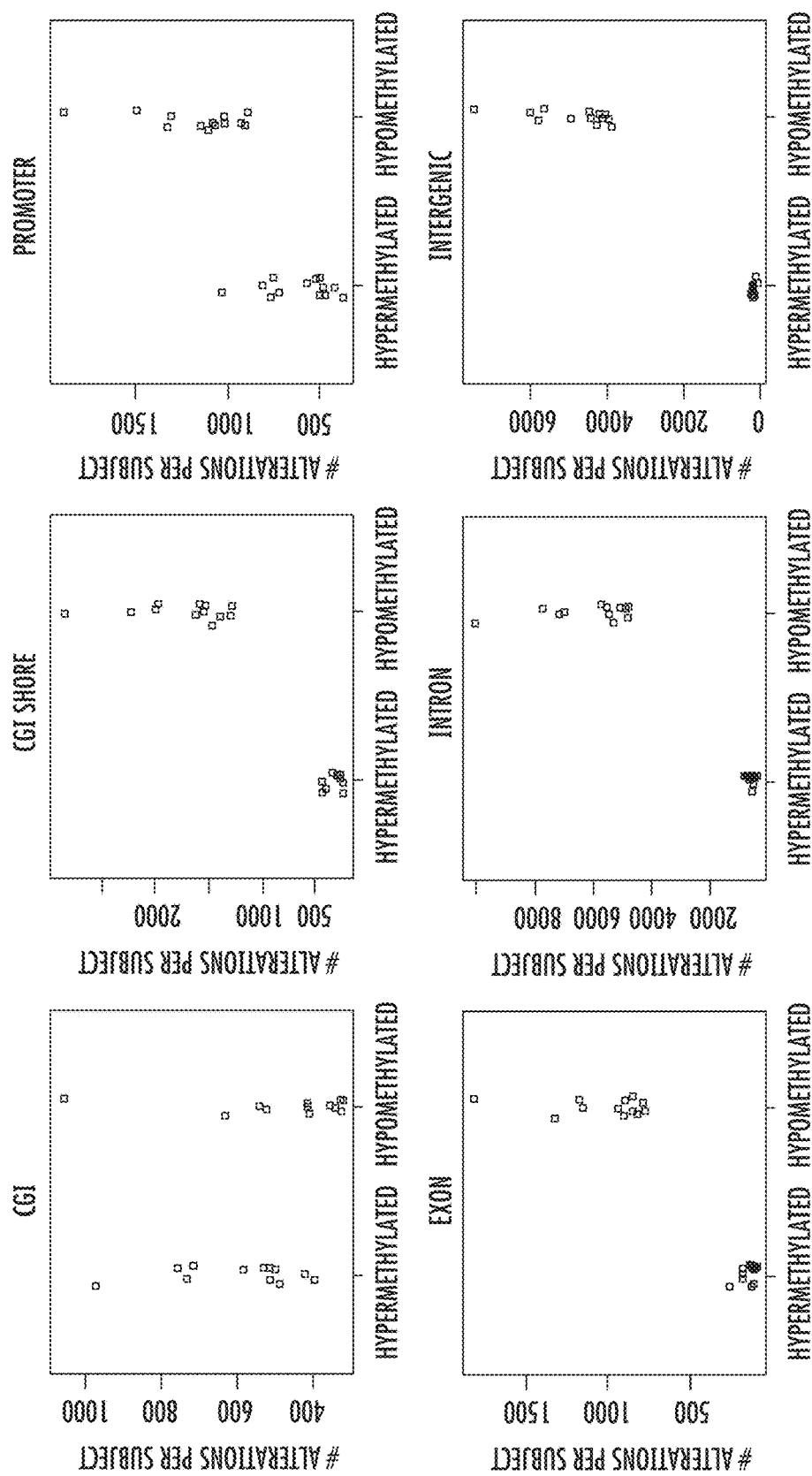
FIG. 13. Distribution of number of probes within various genome annotations showing DNA methylation alterations in each subject. The number of hyper- and hypo-methylated regions by subject are shown.
Figure 14:
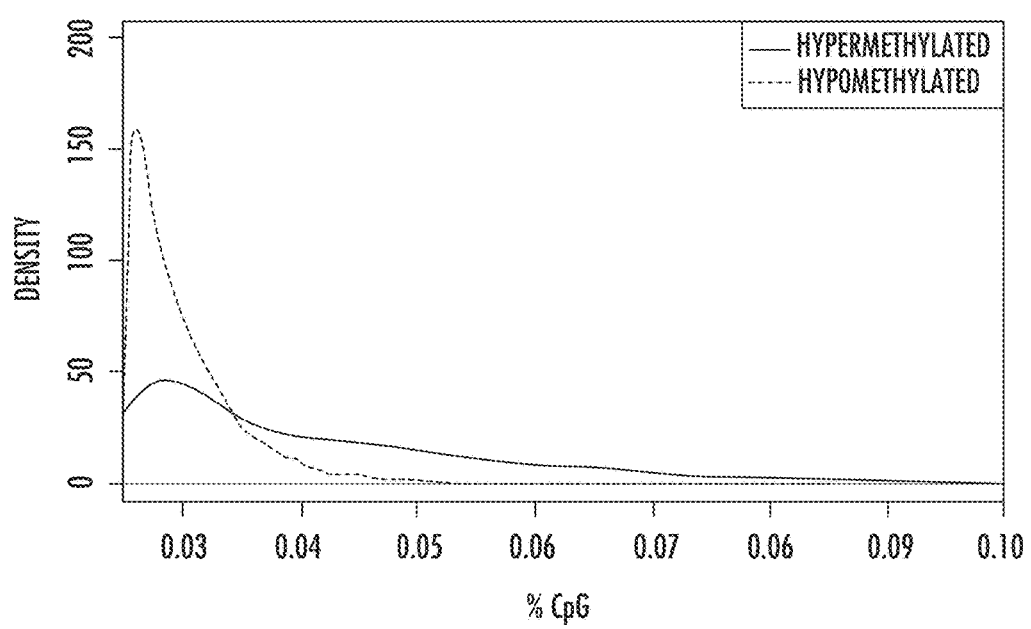
FIG. 14. Distribution of CpG content of regions showing DNA methylation alterations. CpG content is calculated for each restriction fragment containing a probe locus classified as hyper- or hypo-methylated.

Focusing on TM, we identified a total of 3943 regions that showed no evidence of methylation in any of the normal prostate tissues but were hypermethylated in at least one prostate cancer specimen (table S3). The frequency of these hypermethylation events ranged widely, from affecting just a single subject to being hypermethylated in all subjects analyzed (FIGS. S4 and S5); 1329 regions showed hypermethylation in at least 25% of the metastatic prostate cancer tissues. Among these were several gene promoters known to be frequently hypermethylated in primary and metastatic prostate cancer (19), such as those of the GSTP1 (100% of tumors) and APC (89% of tumors) genes (table S3). Regions showing hypermethylation in any tumor were highly enriched within gene promoter regions (FIG. 11). On average, each subject showed hypermethylation at 611 promoter probes (range, 372 to 1039) representing 498 gene promoter regions (~1500 when extrapolated to the whole genome) (FIGS. S7 and S8). Some subjects showed alteration of >700 gene promoter regions (~2100 when extrapolated to the whole genome), consistent with a CGI hypermethylator phenotype as has been suggested for colon and other cancer types (22-24). We investigated differences in methylation patterns associated with promoter proximity and found that promoter-associated CGIs are significantly more likely to be hypermethylated than nonpromoter CGIs (P<1×10-10). The genes associated with hypermethylated gene promoters were highly enriched for differentiation and development-associated Gene Ontology (GO) terms (25), as well as the Memorial Sloan Kettering Prostate Cancer Pathways gene set (26) and multiple gene sets from the National Cancer Institute (NCI) Cancer Gene Index (27) (FIG. 11 and Supplementary Materials and Methods). Thus, DNA hypermethylation events may be involved in reprogramming developmental and differentiation states and in activating carcinogenic pathways. In contrast, hypomethylation alterations, defined as those regions that were methylated in all normal prostate tissues but undermethylated in at least one of the metastatic cancer specimens, were more numerous than hypermethylation alterations (12,799 hypomethylated regions occurring in at least 25% of the cancer specimens) but did not show enrichment of promoter regions, any relevant GO terms, or cancer-related gene sets (FIG. 11). Additionally, the hypomethylated regions tended to have lower CpG content than the hypermethylated regions (FIG. 14). These results are consistent with previous reports showing global, widespread losses of DNA methylation, particularly at regions with lower CpG density, accompanied by focal gains of DNA hypermethylation at CpG-rich promoter regions in cancer cells (28-33).

Figure 2A:
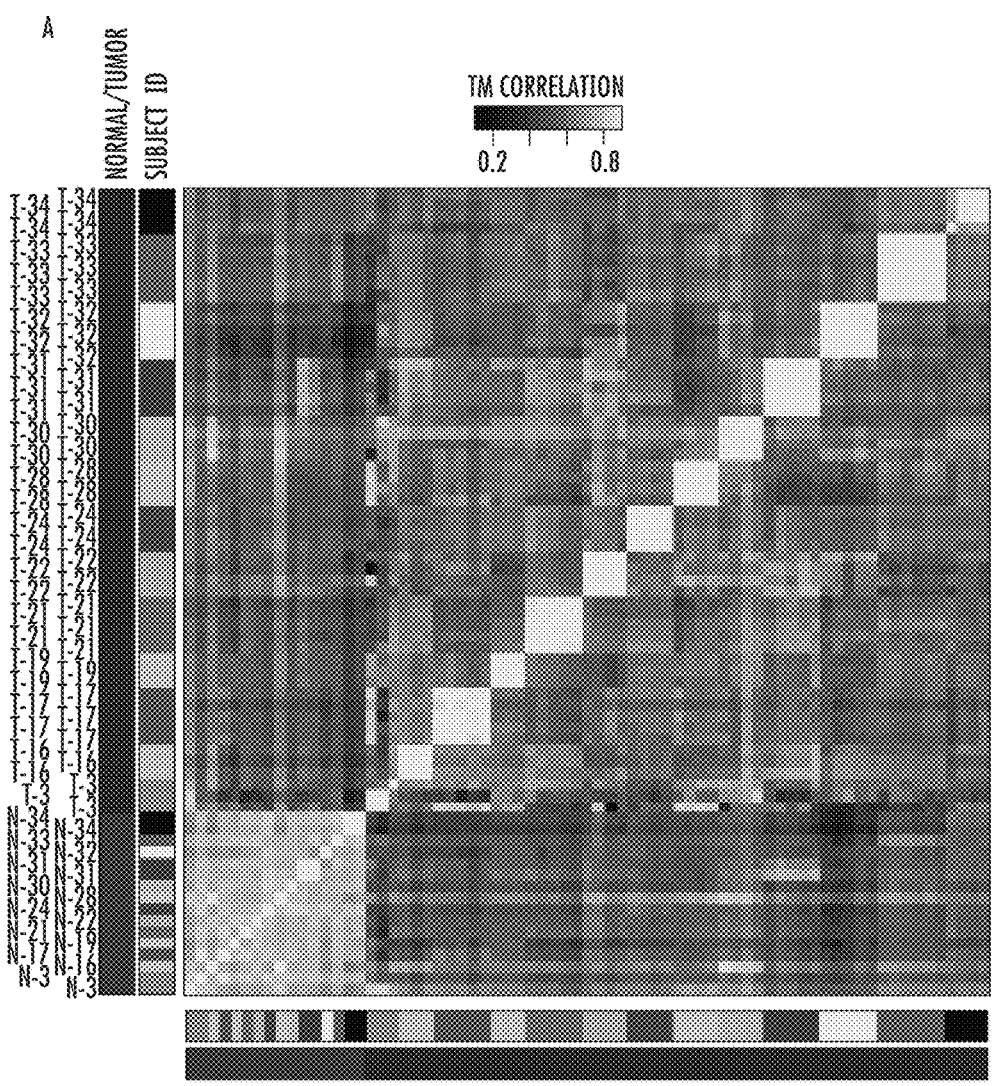
FIG. 2A-2C. DNA methylation alterations are heterogeneous across individuals but closely maintained in the metastases within each individual. (A and B) Between-sample correlation for (A) TM and (B) ASM. Axis labels indicate tissue type (tumor versus normal) and subject identifier. The light colored block diagonal structure shows high interindividual correlation for normal tissues (bottom left) and high intraindividual correlation and interindividual heterogeneity for metastases. (C) DNA methylation hierarchical clustering showing high within-subject similarity and between-subject heterogeneity of metastases. These analyses were done using the 500 probes showing greatest variability across all samples.
Figure 2B:
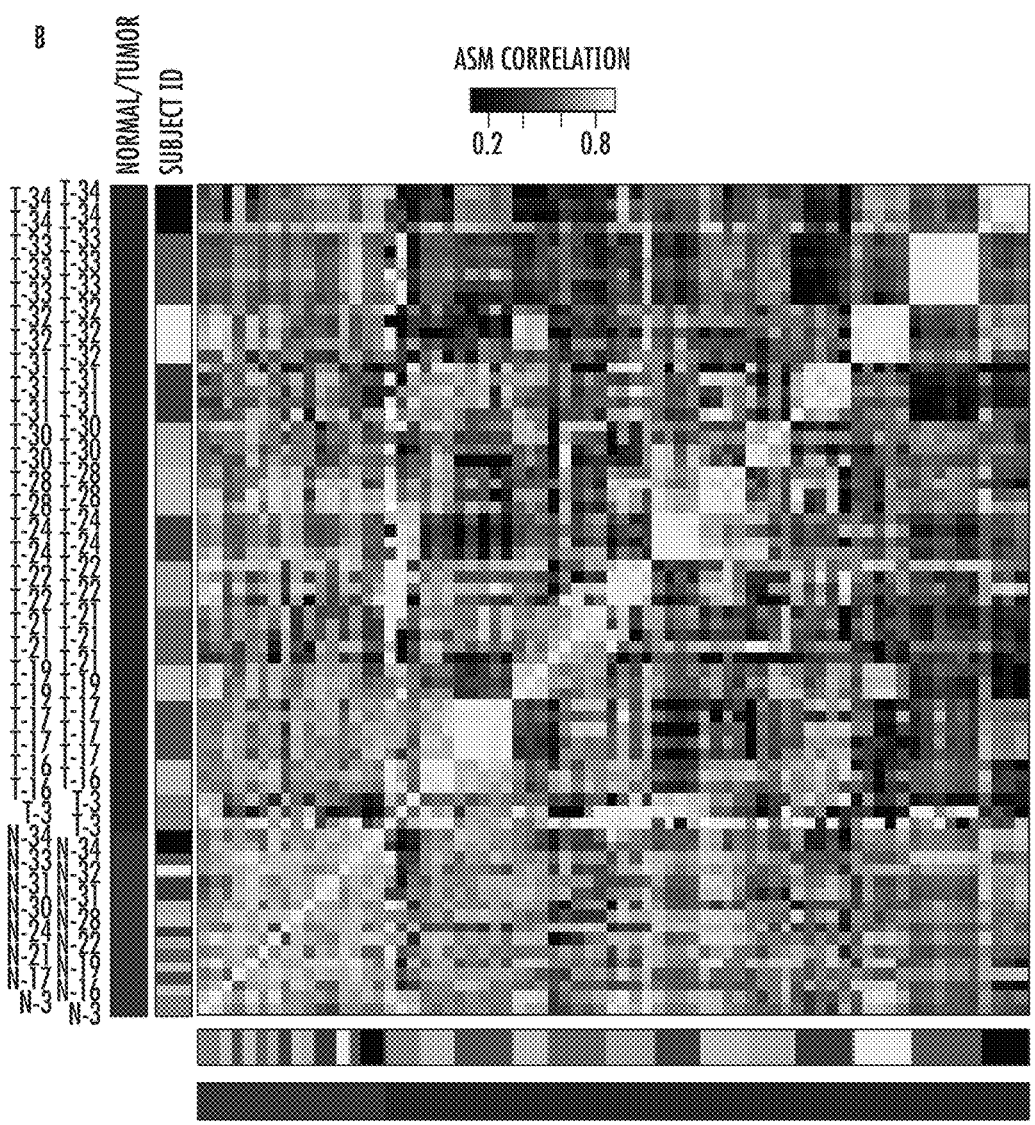
Figure 2C:
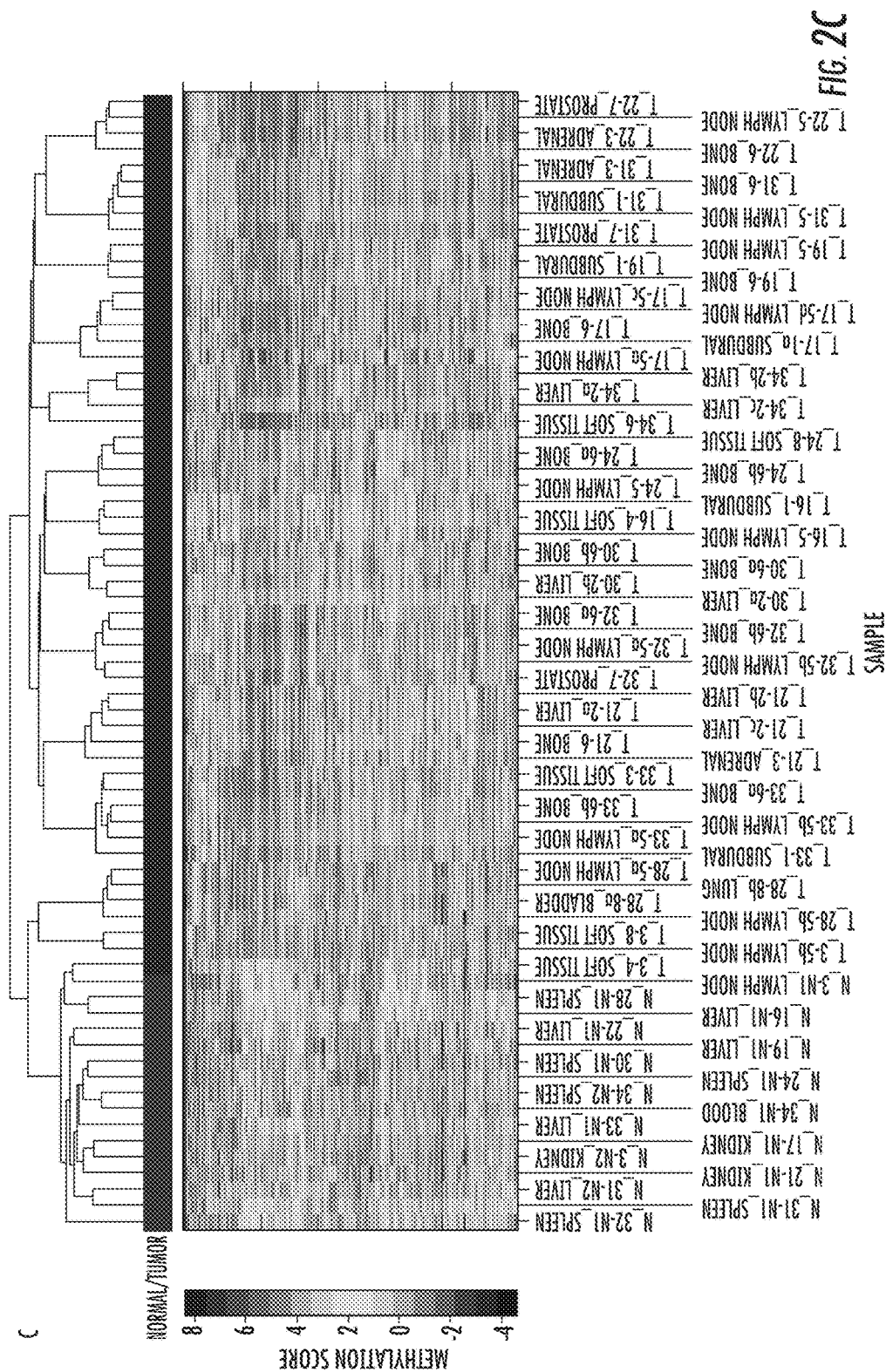

Clonal maintenance of DNA methylation alterations across metastatic dissemination. Having established genome-scale measurements of TM and ASM patterns in each specimen, we examined the degree to which these patterns were maintained across anatomically distinct metastases within each individual. TM patterns in metastases from any given individual showed very high pairwise correlations, with much lower pairwise correlations between metastases from different individuals (FIG. 2A). In contrast, the normal specimens showed high correlations between individuals. A similar but less pronounced pattern was observed for ASM patterns (FIG. 2B). Unsupervised hierarchical clustering using Euclidean distance confirmed that there was relatively little tumor heterogeneity in metastases within subjects compared to the significant tumor heterogeneity across subjects, resulting in clustering of tumors by subject, even after rigorously controlling for copy number effects (FIG. 2C). Together, these data suggest that the tumor/metastasis-initiating clone or subclone in each individual has a unique DNA methylation signature that is then closely maintained across metastatic dissemination.

Figure 3A:
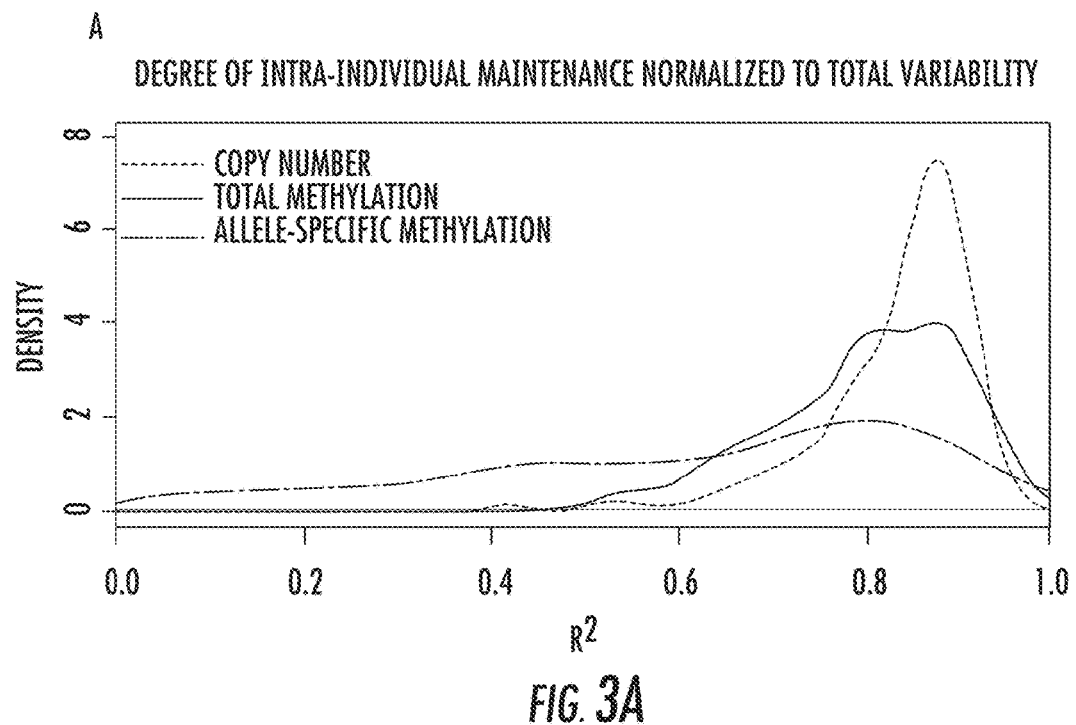
FIG. 3A-3D. Epigenetic DNA methylation changes are maintained to an extent comparable to genetic copy number alterations. (A) Degree of maintenance within subjects normalized to the overall variability (R2) for somatic copy number alterations, TM alterations, and ASM alterations. The 500 probes with highest overall tumor variability were analyzed. (B) A subject showing near-perfect similarity between copy number and DNA methylation hierarchical clustering dendrograms. (C) Degree of similarity between within subject hierarchical clustering of copy number and DNA methylation profiles is significantly greater than would be expected by random chance. (D) R2 distribution for somatically altered regions. The degree of maintenance normalized to overall variability is higher for somatically hypermethylated regions than hypomethylated regions.

Because genetic alterations in copy number are highly maintained across prostate cancer metastatic dissemination (16), we compared the extent of maintenance of epigenetic alterations in DNA methylation to that of copy number alterations. To facilitate comparisons between these genetic and epigenetic data sets, we fit probe-level analysis of variance (ANOVA) models to estimate the degree of maintenance of each type of somatic alteration normalized to the total variability of that alteration (represented by R2 from the model). This was done for those probes showing a low variability in the normal prostate tissues but a high degree of variability across metastases. The resulting R2 measures have values between 0 and 1, with values near 0 indicating high variability across different metastases from each subject and values near 1 indicating nearly perfect consistency of methylation levels across all metastases from each subject. These analyses confirmed that copy number alterations showed a high degree of clonal maintenance. Total DNA methylation alterations showed a degree of clonal maintenance that was comparable to that of copy number alterations (FIG. 3A, FIGS. S10 to S13, and Supplementary Materials and Methods). ASM alterations showed markedly less clonal maintenance, although about 17% of regions exhibited a level of clonal maintenance in ASM comparable to that of copy number alterations.

Figure 3B:
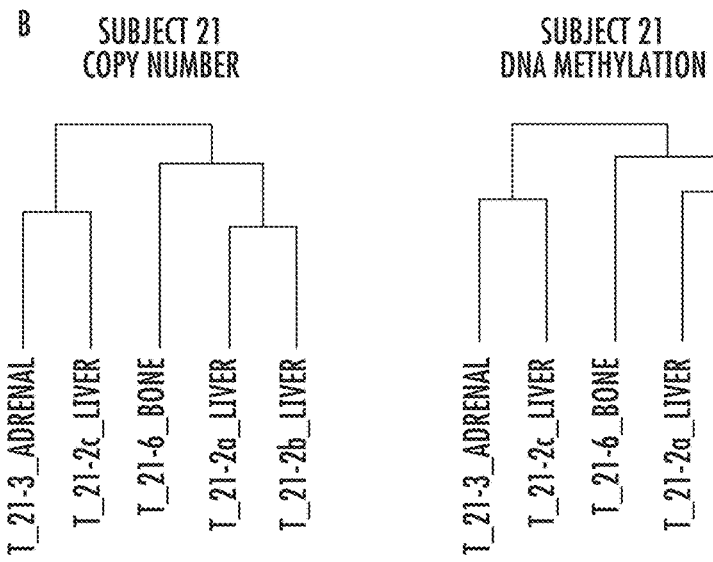
Figure 3C:
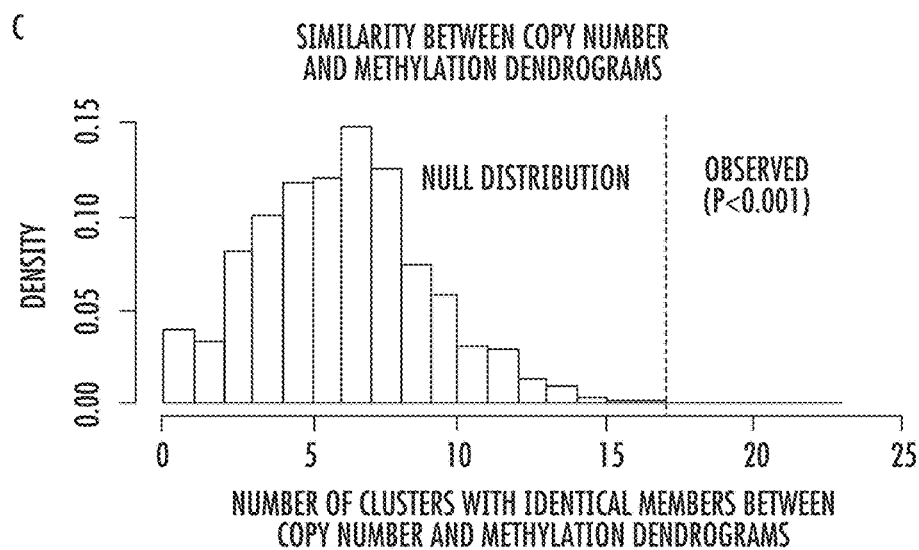

The observation that copy number and TM alterations were maintained to a similar extent across metastases from each subject suggested that these genetic and epigenetic changes may have developed through parallel clonal evolutionary processes. For instance, subject 21 showed a near-perfect coevolution of copy number and DNA methylation patterns (FIG. 3B). This similarity between the branching patterns from hierarchical clustering dendrograms generated from copy number data and that generated from the DNA methylation data was significant across all subjects (FIG. 3C; P<0.001; Supplementary Materials and Methods). Together, these analyses indicate that DNA methylation patterns can be as robustly maintained across metastatic dissemination as genetic copy number alterations.

Figure 3D:
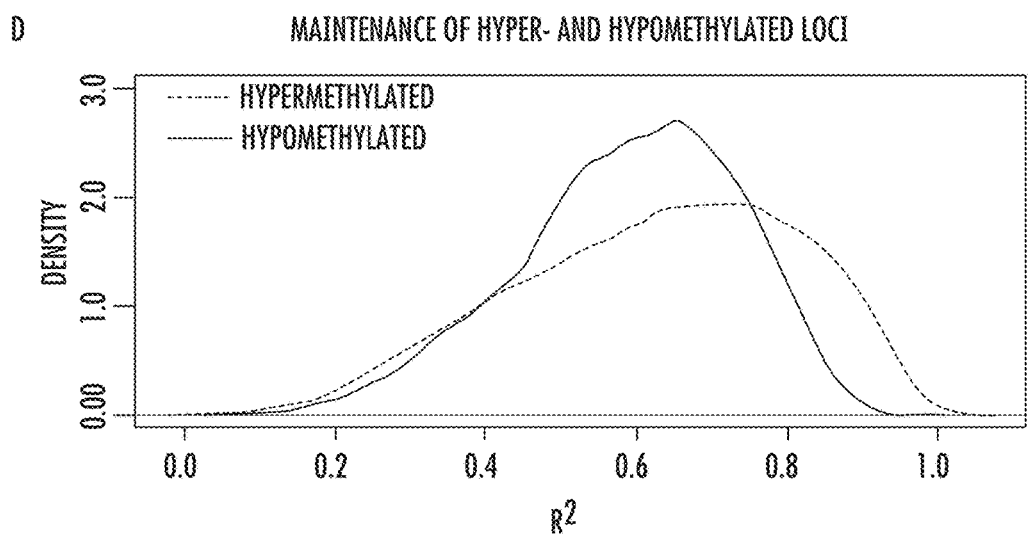
Figure 19:
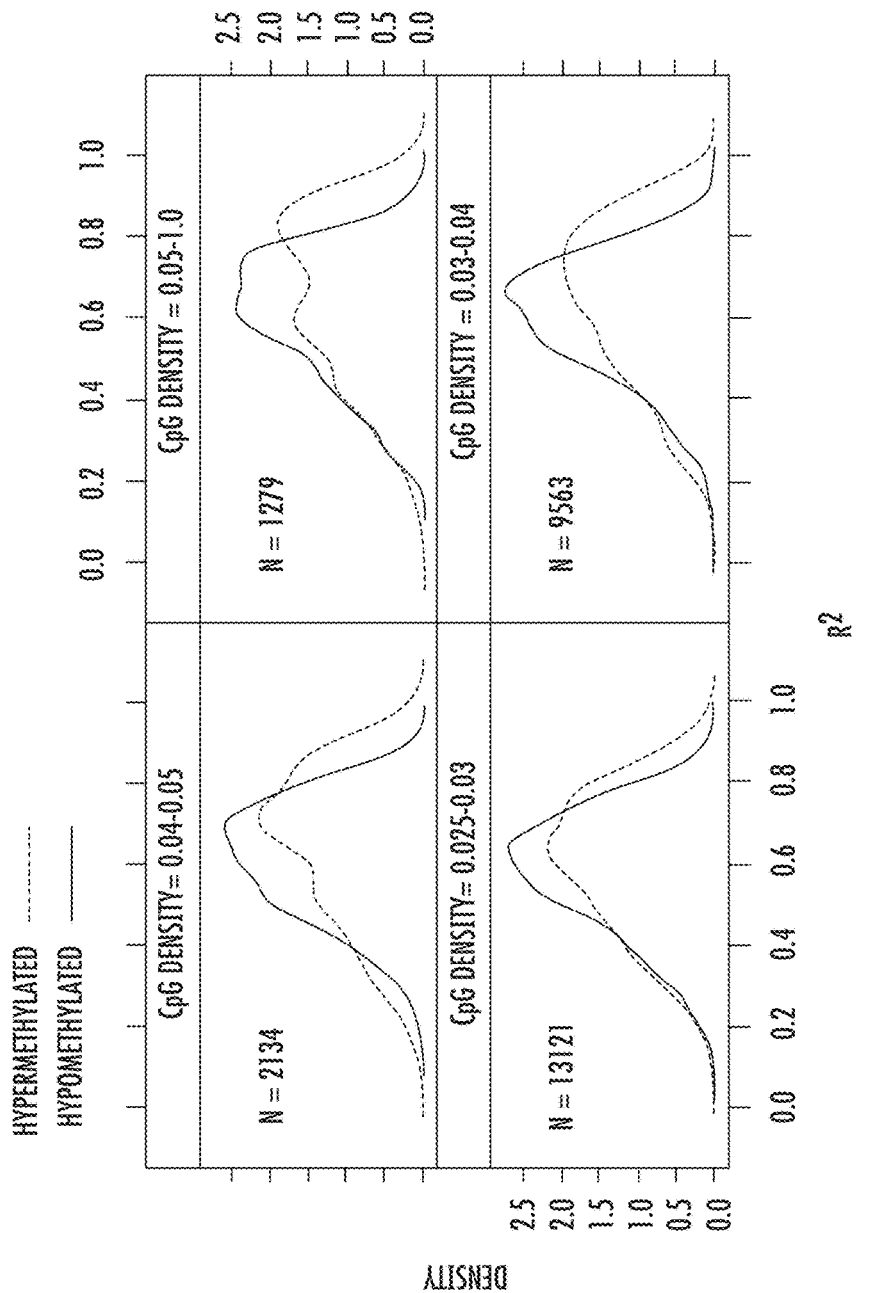
FIG. 19. Distribution of R2 for hyper- and hypomethylation alterations stratified by CpG density. The fraction of tumor heterogeneity explained by within-subject variability is consistently lower in hypermethylated regions than in hypomethylated regions independent of CpG density.

Given the differences in the functional annotations of hyper- and hypomethylation events in the prostate cancer specimens, we examined whether there were differences in the tendency to maintain hypermethylation versus hypomethylation alterations during metastatic dissemination. Hypermethylation alterations showed a higher degree of maintenance (R2) than hypomethylation alterations (FIG. 3D). This difference was evident even after controlling for CpG density (FIG. 19). Together with the enrichment of differentiation/ development and cancer-related gene sets in hypermethylated gene promoters, the high degree of maintenance of hypermethylation changes suggests that these events are enriched for driver alterations.

Figure 4A:
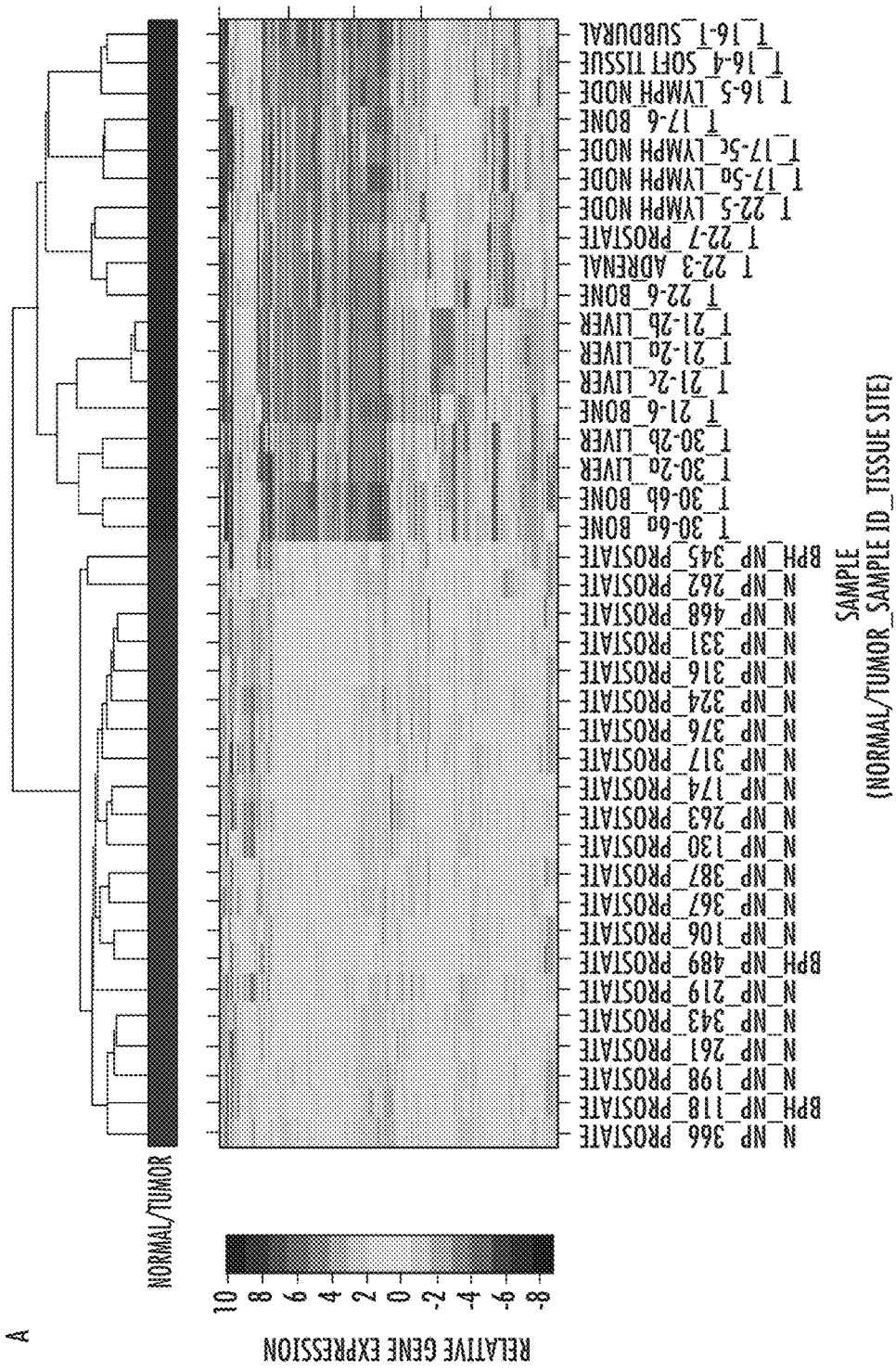
FIG. 4A-4C. Gene expression patterns show high within-subject maintenance and correlation with DNA hypermethylation. (A) Gene expression hierarchical clustering showing high within-subject similarity and between-subject heterogeneity of metastases. These analyses were done using the 500 genes showing greatest variability in gene expression across all 21 benign and 18 metastasis samples with gene expression microarray data. (B) DNA promoter hypermethylation shows significant correlation with down-regulation of gene expression (average fold decrease=1.33, P=5.87×10-38) and is more strongly correlated with gene expression than promoter hypomethylation (P=9.2×10-8). (C) Within subject maintenance (R2) of gene expression patterns for genes with significant correlation between DNA methylation and gene expression was stronger than for those having no evidence for methylation expression correlation.

Association of gene expression patterns with DNA methylation alterations. We next explored associations between DNA methylation alterations and gene expression patterns to understand the functional consequences of somatic DNA methylation alterations in the lethal metastatic prostate cancers. We measured genome-wide gene expression patterns for 18 metastases from 5 autopsy cohort subjects and 21 organ donor benign prostate samples, selected as an arbitrary subset of our overall study samples for which high-quality RNA was available, using the Agilent whole human genome gene expression microarray platform. Analysis of differential expression between the metastases and normal prostate tissues revealed 235 up-regulated and 1082 downregulated genes (at thresholds of |fold change|>2 and P<0.01; table S4), including several previously known prostate cancer differentially expressed genes [for example, AMACR, HPN, EZH2, and GSTP1 (34-37)]. Unsupervised hierarchical sample clustering by gene expression measures of the 500 most variably expressed genes across all samples showed the same patterns of within-subject maintenance and between-subject heterogeneity as was observed for DNA methylation (FIG. 4A).

Figure 4B:
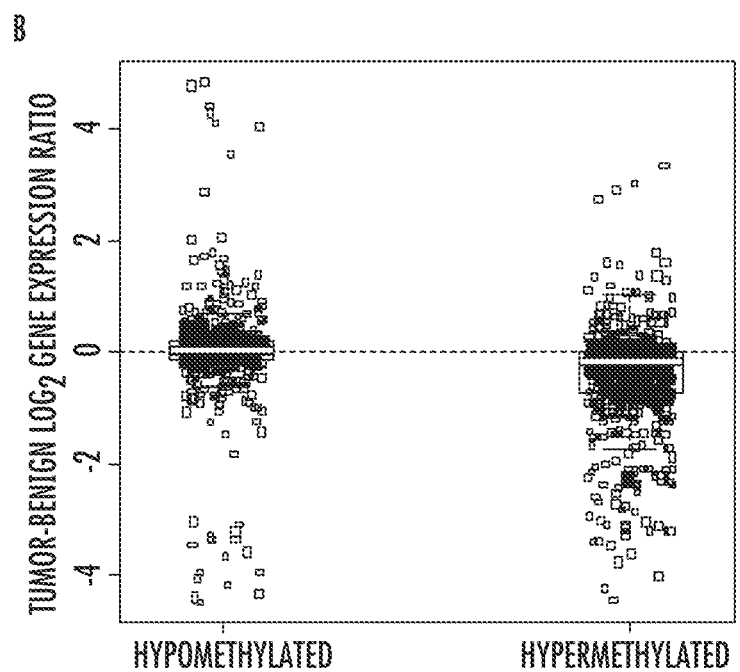
Figure 20:
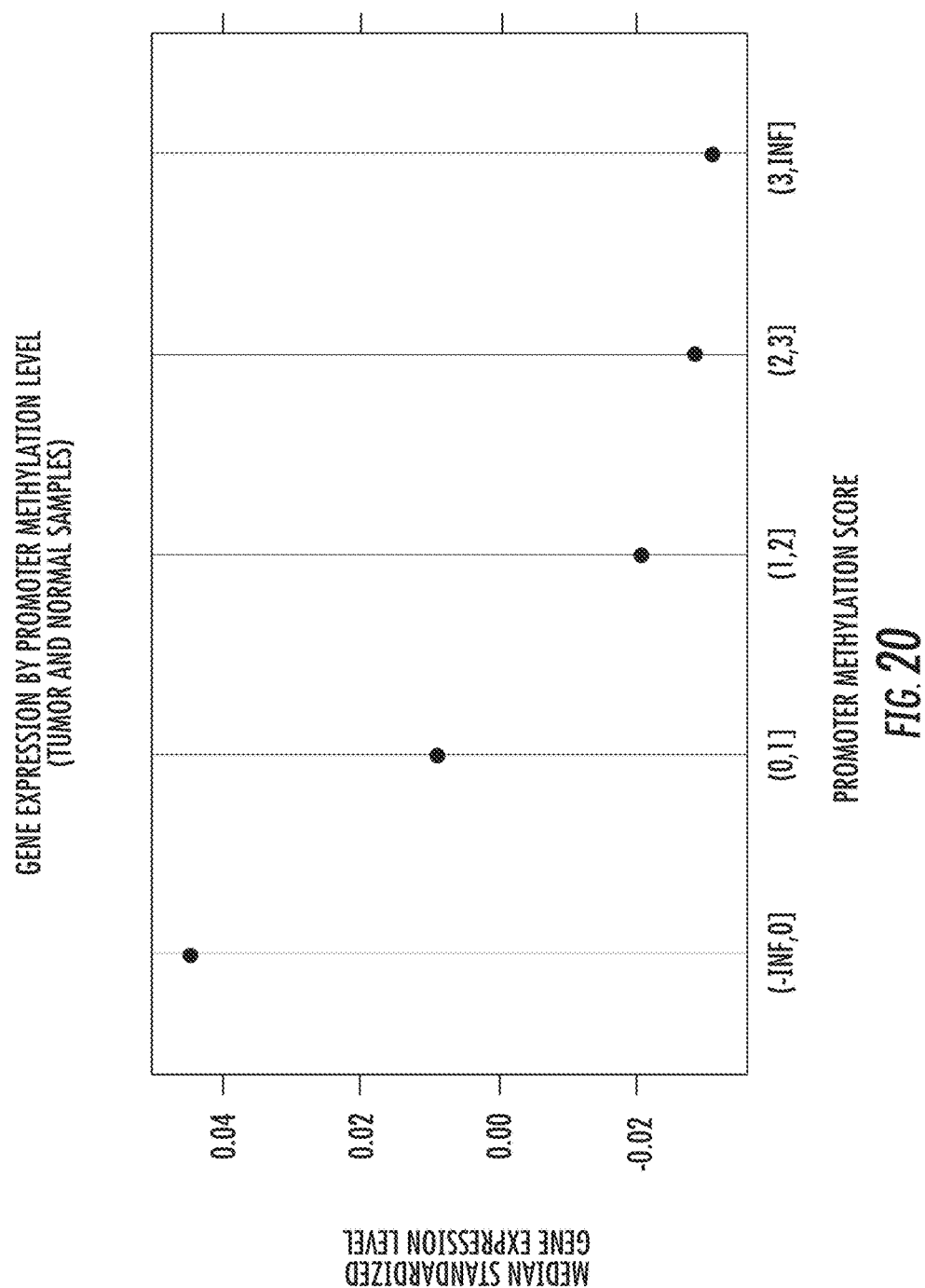
FIG. 20. Median gene expression by promoter methylation level. A total of 4194 genes had data for both gene expression and promoter methylation. Each gene's expression levels were standardized by dividing by the standard deviation across all subjects.

Given this similarity, we examined whether there was a correlation between the DNA methylation and expression patterns. Intersecting the coverage of the MBD-SNP platform with the gene expression microarray platform resulted in a set of 4194 genes for which both expression and promoter methylation data were available. We first examined whether DNA methylation alterations were correlated with gene expression at these genes. There was a weak but significant inverse correlation overall between gene promoter methylation and gene expression measures across all samples and all 4194 genes (FIG. 20). Because we previously found that there were differences in the degree of maintenance (R2) between the hypermethylated and hypomethylated loci, we now assessed whether there were differences in the correlation between DNA methylation and expression at each of these types of somatic methylation alterations. Regions showing promoter hypermethylation in the metastases were strongly associated with reduced levels of gene expression (average fold decrease=1.33, P=5.87× 10-38, FIG. 4B), including at genes in the development/ differentiation pathways, which were enriched for hypermethylation. Such genes include SFRP1, EFEMP1, CD44, RERG, NTN4, CCK, GPX3, COL9A3, DPYSL3, ALOX5, EY A4, and SFN. These genes show at least a 1.2-fold decrease in gene expression in hypermethylated tumors relative to benign prostate tissue and are part of Gene Ontology categories significantly enriched in hypermethylation (FDR=5%). See FIG. S16 (not provided herein) of the Supplemental Materials, available in Aryee et al., 5(169) SCI. TRANSL. MED. 169ra10 (2013). The Supplemental Materials are herein incorporated by reference. Additionally, promoter hypermethylation was significantly more associated with gene expression differences than was promoter hypomethylation (P=9.2×10-8), which generally had negligible association with gene expression.

We next identified the individual loci that showed evidence for significant correlation between gene expression and DNA methylation in the metastatic prostate cancer tissues. For these analyses, we were restricted to the 3158 loci that were in the top 50th percentile of variability for either gene expression or promoter methylation to exclude regions that showed little or no variation in either data set. We found that 452 of these 3158 loci showed a nominally significant correlation between gene expression and DNA methylation at P<0.05, of which most showed the expected negative correlation (FIG. S16 of the Supplemental Materials (data not shown herein)). The positive correlation between DNA methylation and gene expression in a minority of regions (FIG. S16 of the Supplemental Materials (data not shown herein)) may be due to our definition of promoter regions, which includes portions of gene bodies and insulator regions, or might be due to complex cis and trans regulation leading to activation of hypermethylated genes (38).

Figure 4C:
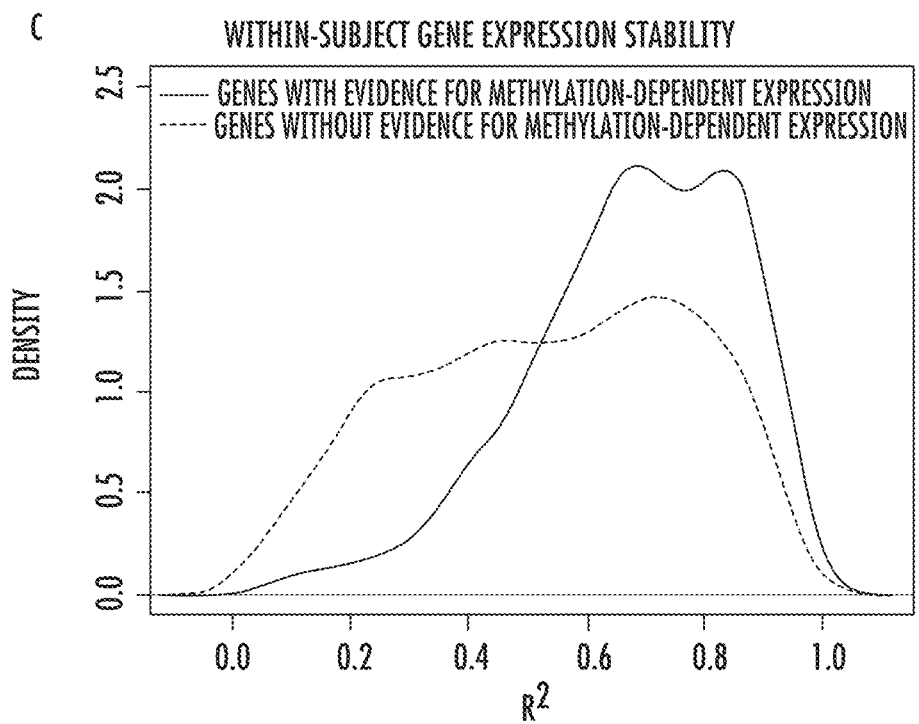
Figure 21:
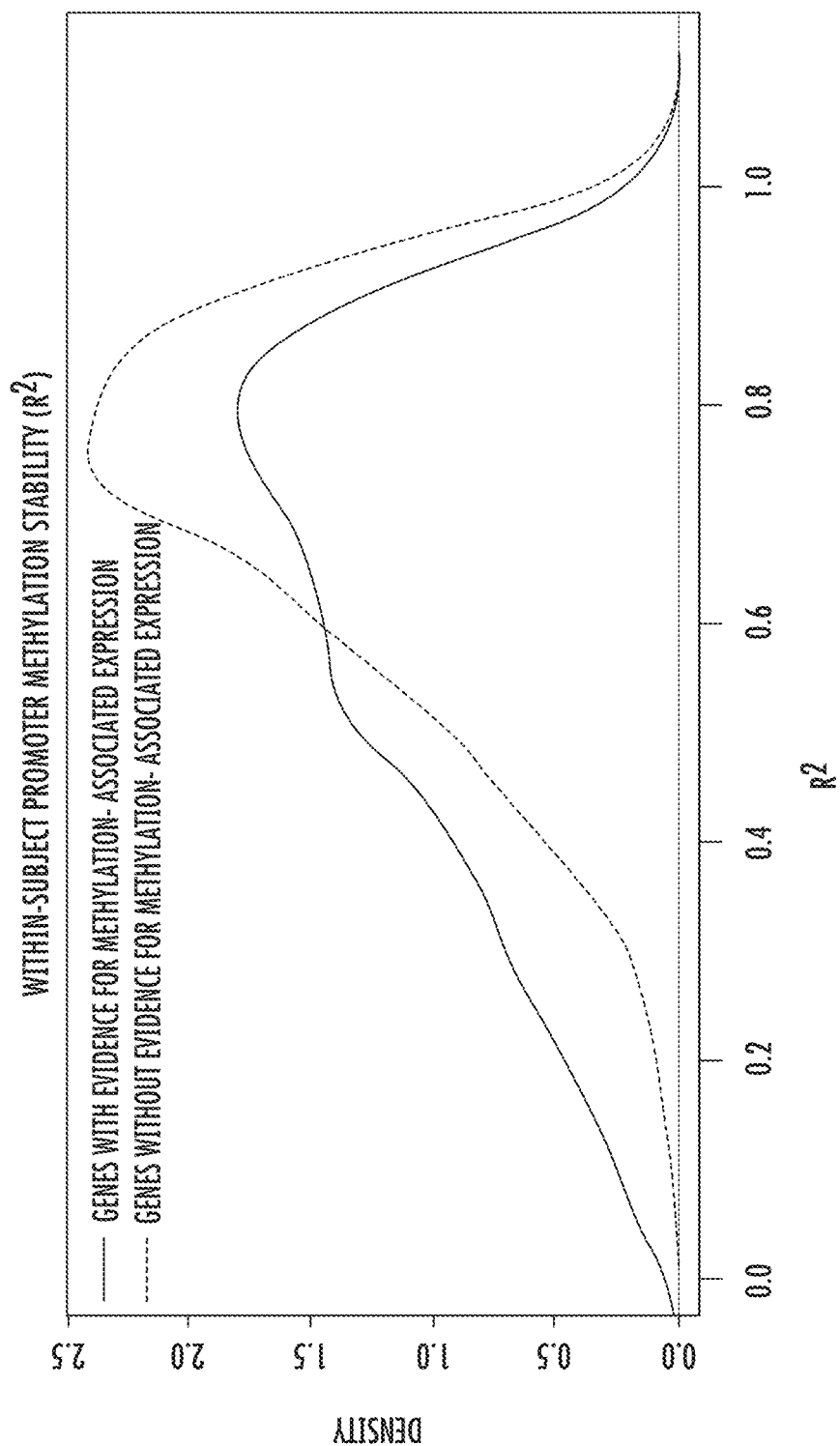
FIG. 21. Promoter DNA methylation R2 representing the degree of within-subject stability of methylation across anatomically distinct tumors. Genes whose promoter methylation levels are associated with gene expression level ($p<0.05$, red line) are more stably maintained across tumors than those without a significant gene expression association (blue line).

Although there was an overall strong pattern of within-subject stability in gene expression (see FIG. 4A), this intraindividual stability (R2) was strongest for those 452 genes whose expression level was associated with promoter DNA methylation (FIG. 4C). Similarly, those promoter methylation loci that were associated with gene expression changes were more stably maintained within subjects than those whose methylation did not show significant correlation with gene expression (FIG. 21). These observations suggest that DNA methylation alterations that are associated with phenotypic changes in gene expression have a greater tendency to be maintained within individuals, perhaps due to selection of those phenotypes, leading to maintenance of both the DNA methylation and gene expression patterns.

Figure 22:
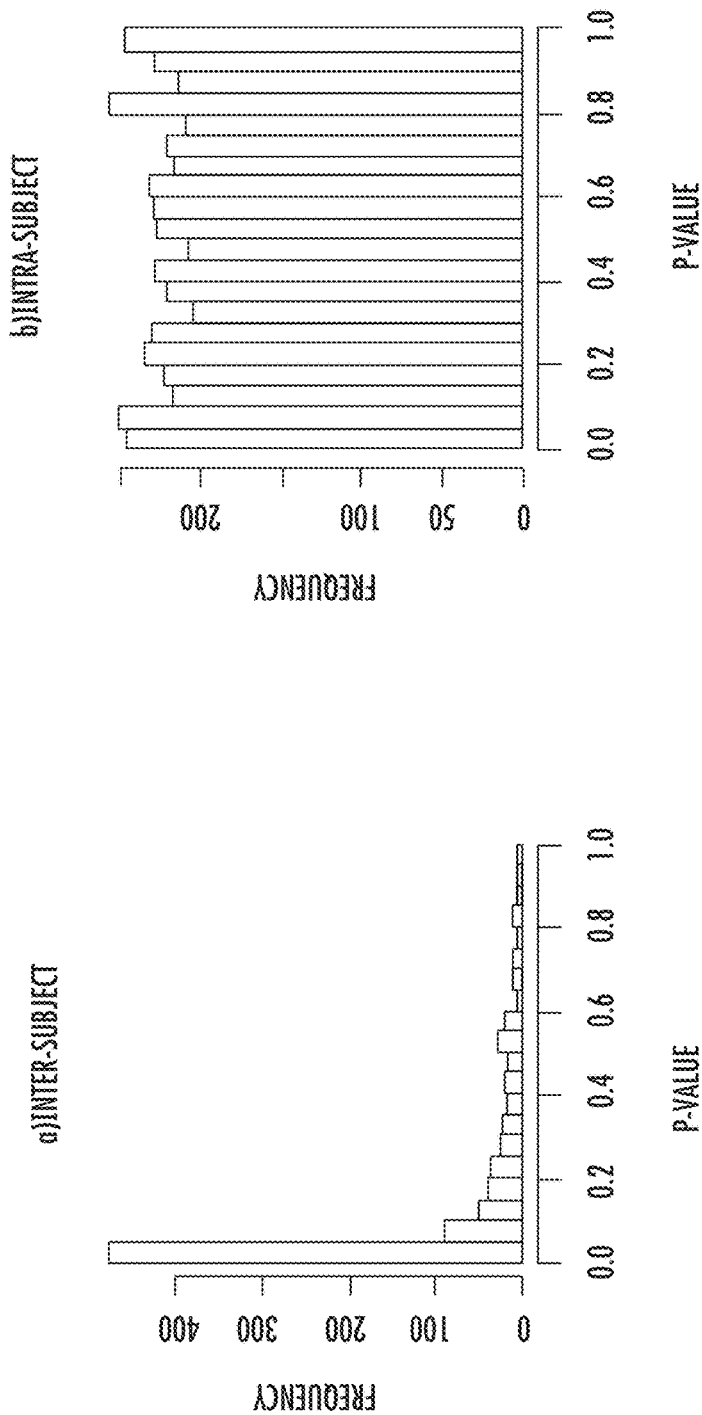
FIG. 22. P values for association between gene expression and promoter DNA methylation in 18 prostate cancer tumor samples from five patients. (a) Differences in DNA methylation between general not associated with gene expression differences. individuals correlate strongly with gene expression. (b) Intra-subject differences in DNA methylation are in general not associated with gene expression differences.

A careful examination of FIG. 2C shows that although intraindividual heterogeneity in DNA methylation is much smaller than interindividual heterogeneity, different metastases within each individual show clear patterns of clonal evolution and tumor heterogeneity in their methylation patterns. We next explored whether this intraindividual tumor heterogeneity in DNA methylation was correlated with phenotypic changes in gene expression. At a general level, we found that although there was a strong correlation between DNA methylation and gene expression at the interindividual level, this general correlation was absent at the intraindividual level (FIG. 22). To focus this analysis further, we assessed the correlation between methylation and expression at specific regions that showed evidence of significant intraindividual tumor heterogeneity in DNA methylation across multiple subjects. We identified 74 hypermethylated loci (1.9% of all hypermethylated regions), including 30 gene promoters, and 1255 hypomethylated loci (5.6% of all hypomethylated regions), including 115 promoters, that showed such a pattern of recurrent intraindividual tumor heterogeneity in DNA methylation (see Supplementary Materials and Methods and FIGS. S19 and S20 (S19 and S20 not shown herein)). The supplementary figures are available in Aryee et al., 5(169) SCI. TRANSL. MED. 169ra10 (2013),and are herein incorporated by reference as if fully reproduced herein.

We found no correlation between DNA methylation and gene expression at the intraindividual level even at these loci, showing significant and recurrent DNA methylation heterogeneity in different metastases within individuals. Furthermore, such regions were not enriched for any GO gene sets. Together, these analyses suggest that DNA methylation alterations showing within-subject tumor heterogeneity are not significantly correlated with gene expression patterns across different metastases within the same individual.

Genomic "cityscapes" of DNA methylation alterations in lethal metastatic prostate cancer. To visualize both frequency andmaintenance of DNA methylation alterations by position across the genome, we constructed cityscapes of DNA methylation changes in lethal metastatic prostate cancer. Such cityscape plots were constructed for regions showing gains and losses in TM (hyper- and hypomethylated regions; FIG. 5) and in ASM (FIG. 23) in the metastases compared to normal prostate tissues. Within each cityscape, chromosomes were folded into neighborhoods along a Hilbert curve (39); the area of each chromosome neighborhood was proportional to the number of informative probes. Within these neighborhoods, each "address" represents a single locus in the genome (tables S2 and S3 list the location and annotation of all interrogated addresses for ASM and TM, respectively). The height of each structure in the cityscape represents the number of tumors showing a somatic DNA methylation alteration. The color of each structure represents the degree of maintenance of methylation across all metastases within each individual as measured by R2 from our ANOVA model, with red indicating a high degree of somatic alteration maintenance (highR2) and white indicating a low degree of maintenance (low R2) relative to total variability. Note that the R2 maintenance metric is not meaningful at loci where overall variability is negligible due to all tumors being fully methylated (for example, the GSTP1 promoter).

Figure 5A:
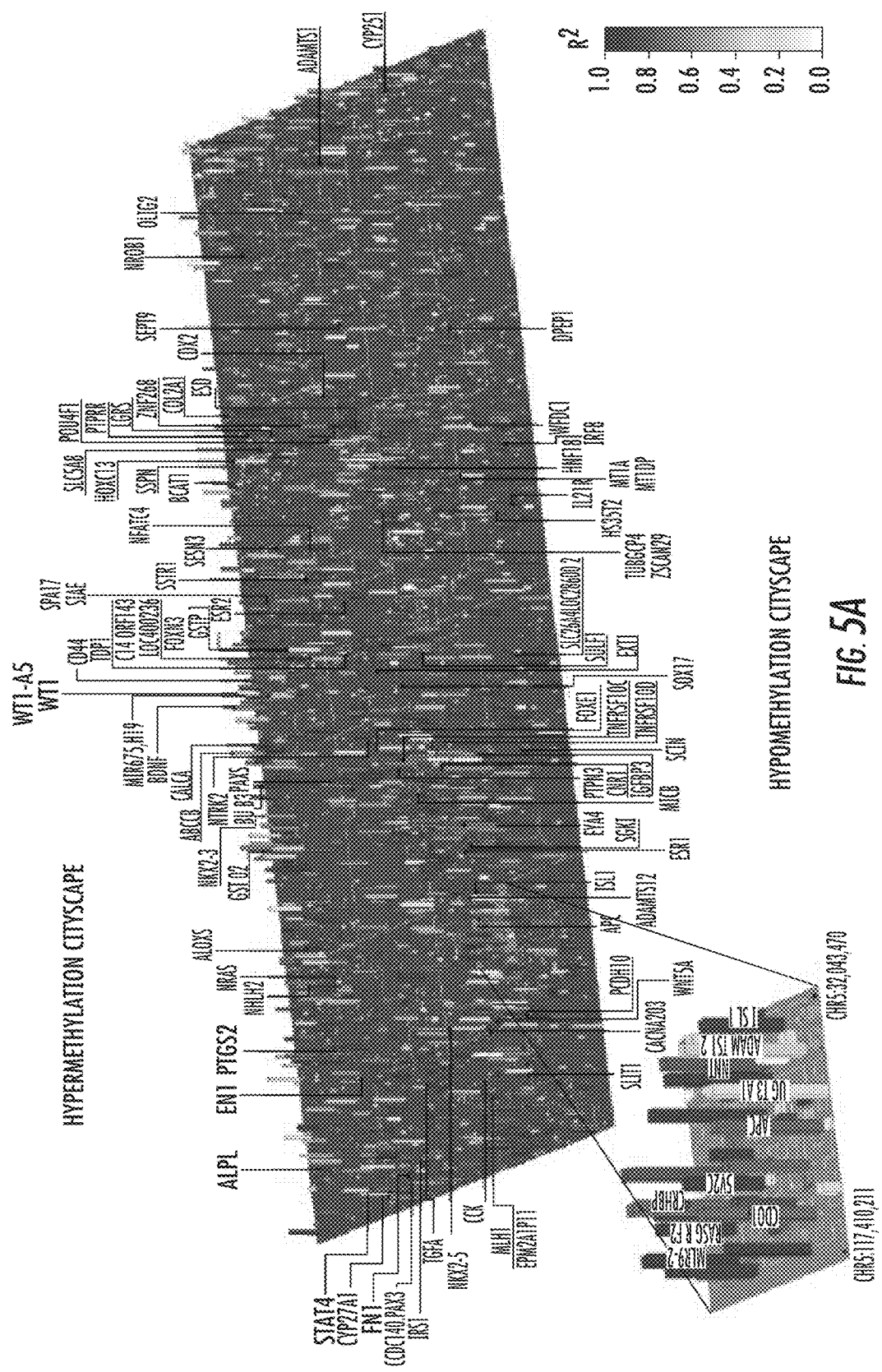
FIG. 5A-5C. DNA methylation cityscape plots of lethal metastatic prostate cancer highlight frequent and highly maintained alterations. (A and B) Genomic cityscapes of somatic (A) hypermethylation and (B) hypomethylation. (C) Each chromosome is folded into neighborhoods along a Hilbert curve. Each structure represents a region showing alteration in TM compared to the normal prostate tissues. The height of each structure indicates the number of tumors showing alteration. The color scale represents the degree of maintenance of these alterations across metastases within individuals normalized to the overall variability (R2). Hypermethylated promoter regions of genes from the NCI Cancer Gene Index that fell in the top 10th percentile of frequency of alteration or R2 are labeled. The magnified region in (A) illustrates a representative chromosomal segment showing clustering of frequently hypermethylated regions (skyscrapers). The white path shows the Hilbert curve "folding" of this genomic segment.
Figure 5B:
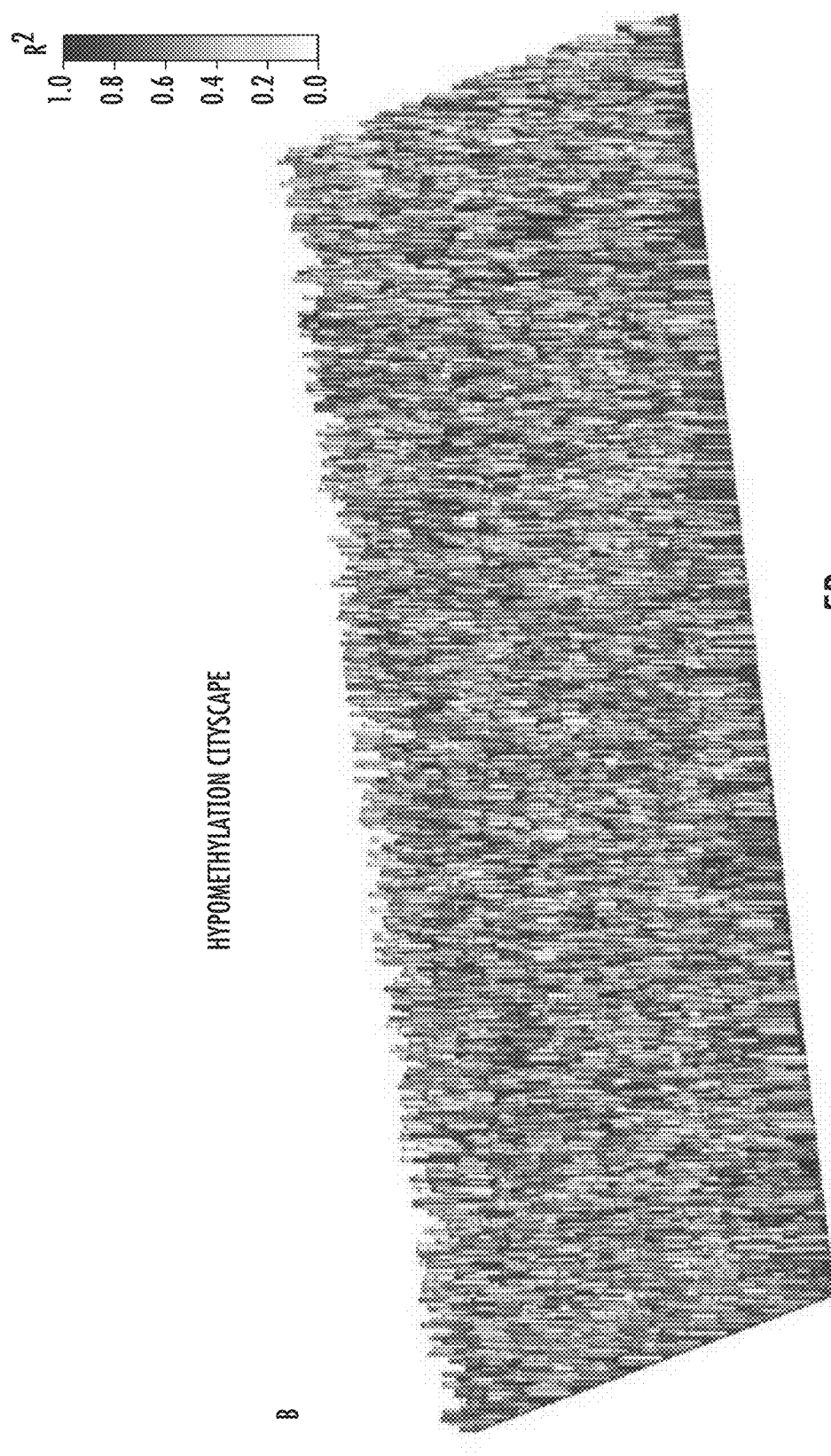
Figure 5C:
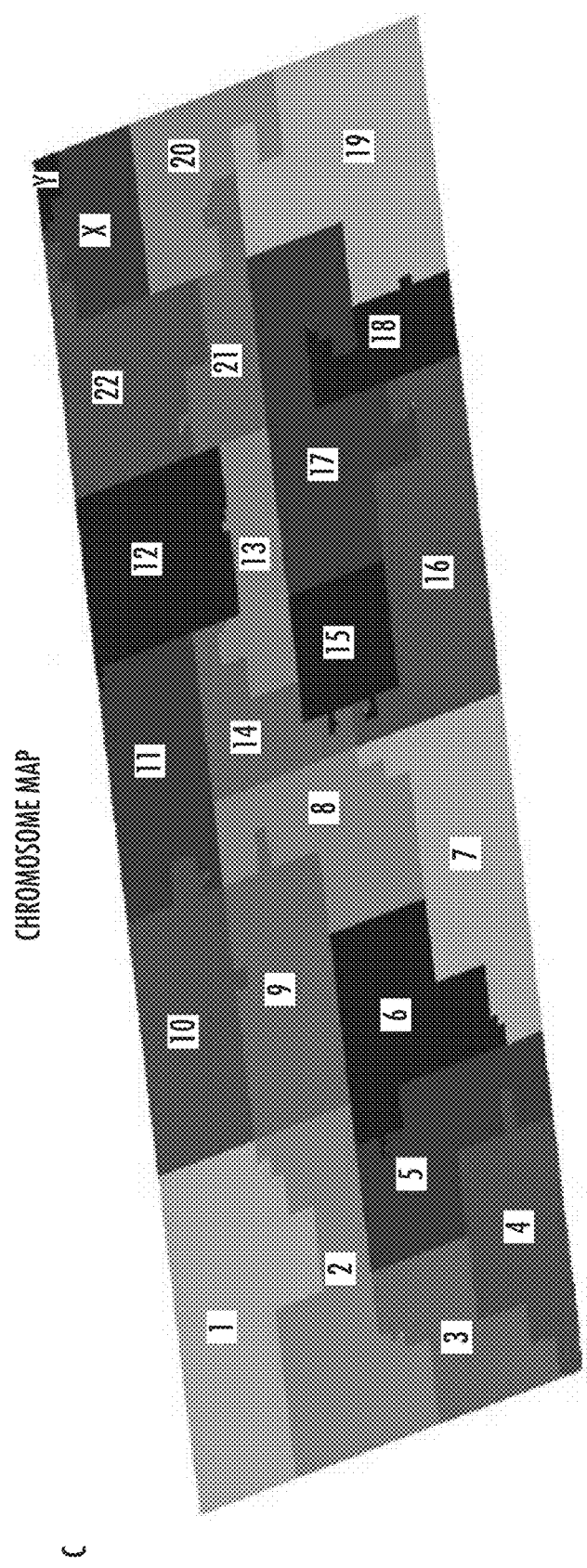
Figure 24A:
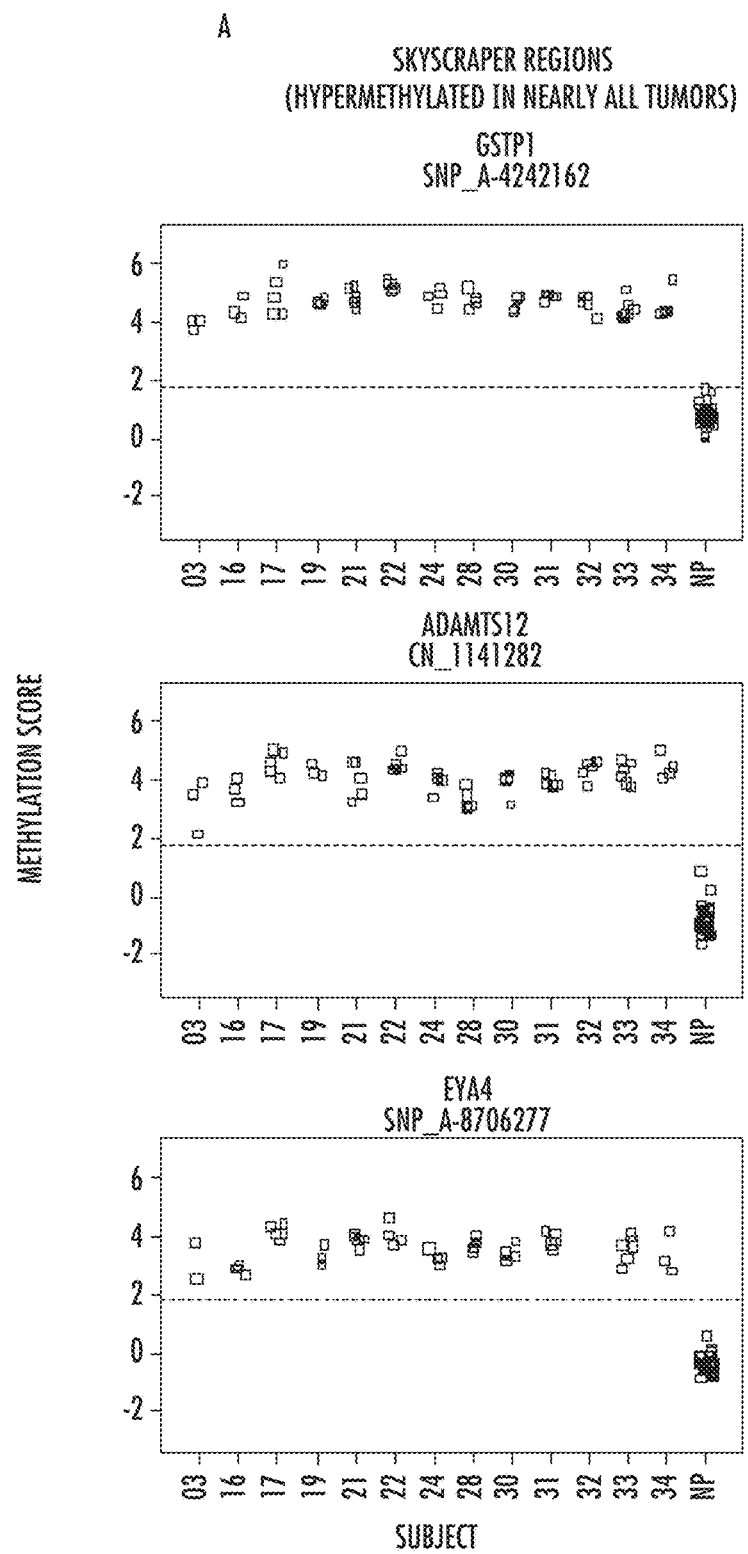
Figure 24B:
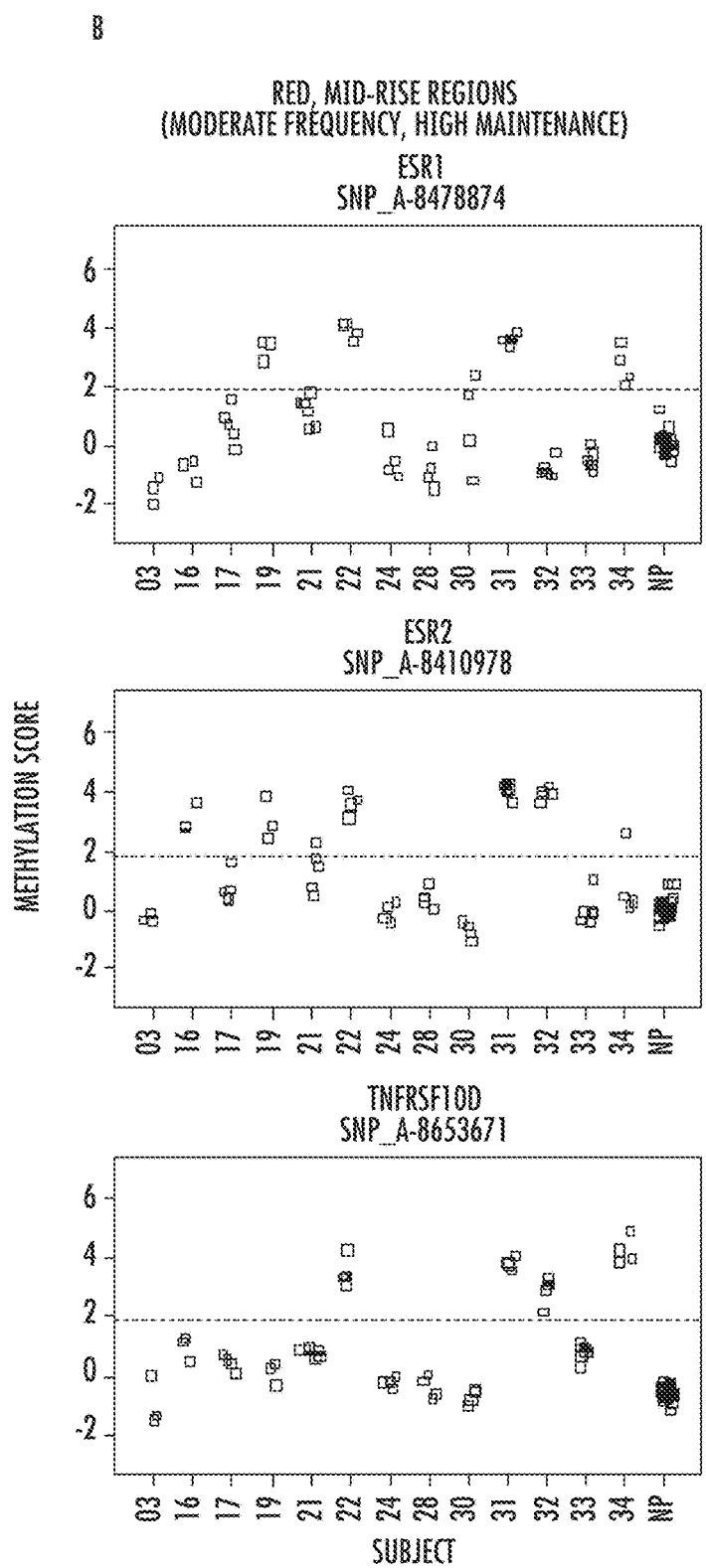
Figure 25:
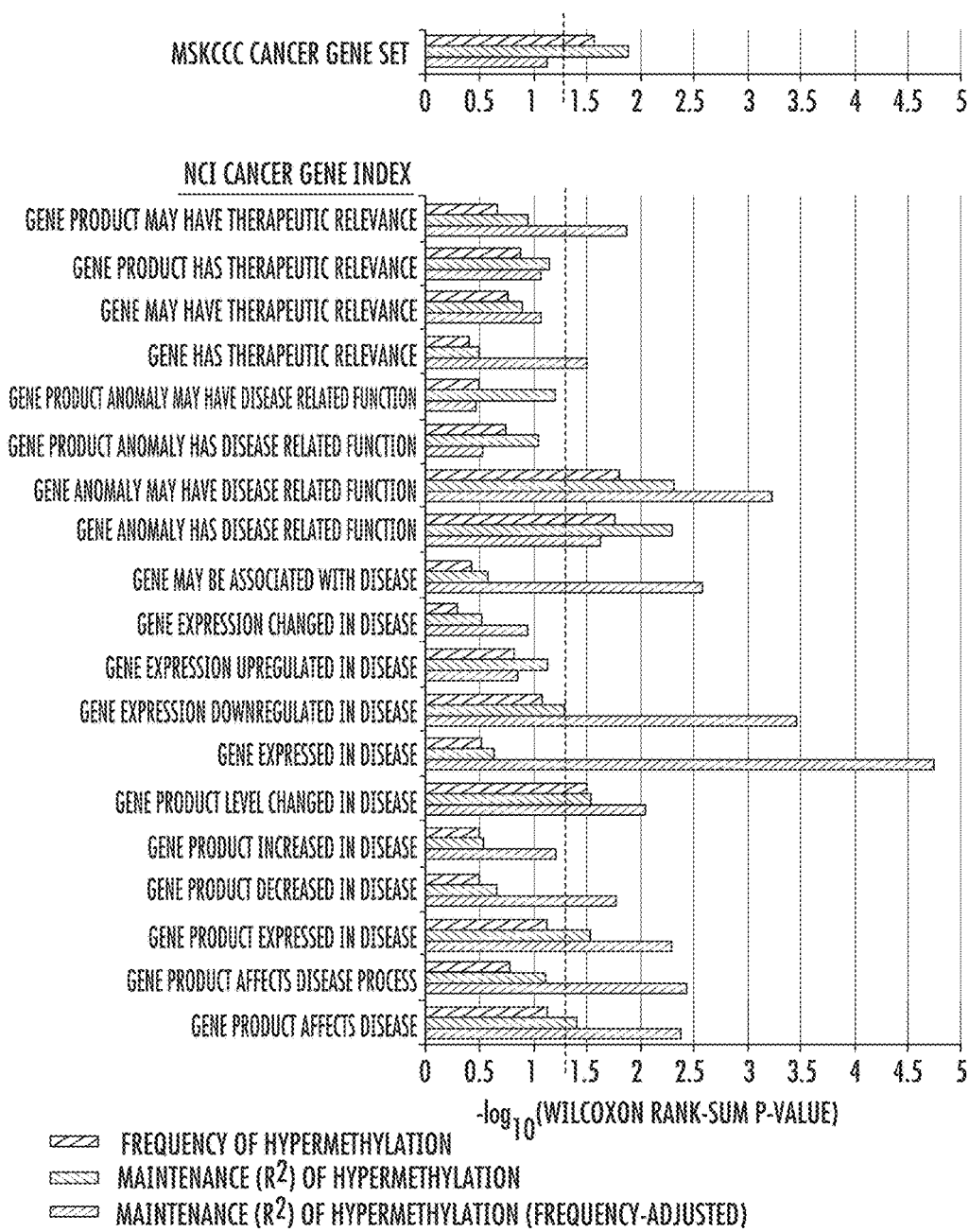
FIG. 25. NCI cancer gene set enrichment for structures in the hypermethylation cityscape. Structures in the hypermethylation cityscape (loci where at least one tumor was methylated) were ranked by number of affected tumors, or maintenance (R2). The Wilcoxon rank-sum test was used to assess gene set enrichment. Dashed line indicates $p=0.05$.

For DNA hypermethylation alterations, several regions appeared as "skyscrapers" in the cityscape, indicating regions that were frequently hypermethylated (FIG. 5A and FIG. 24). Such skyscrapers were highly enriched for the Memorial Sloan Kettering Prostate Cancer Pathways gene set (26) and several sets from the NCI Cancer Gene Index (27) (FIG. 25). The cityscape contains several densely populated neighborhoods with clustered skyscrapers, suggesting contiguous chromosomal segments frequently prone to hypermethylation (FIG. 5A). This observation is consistent with previous findings of long-range epigenetic silencing in large chromosomal tracts (40). We also observed several "low- and mid-rises" in the cityscape, indicating regions that were hypermethylated in only one or a few subjects. Among these low- to mid-rise regions, we found that those that were red, indicating high maintenance of hypermethylation, showed enrichment for cancer-related genes (FIG. 25) relative to white-yellow regions. This cityscape of hypermethylation alterations in lethal metastatic prostate cancer revealed an unexpected importance of low frequency but highly maintained DNA methylation alterations as potential driver epigenome alterations.

Figure 23:
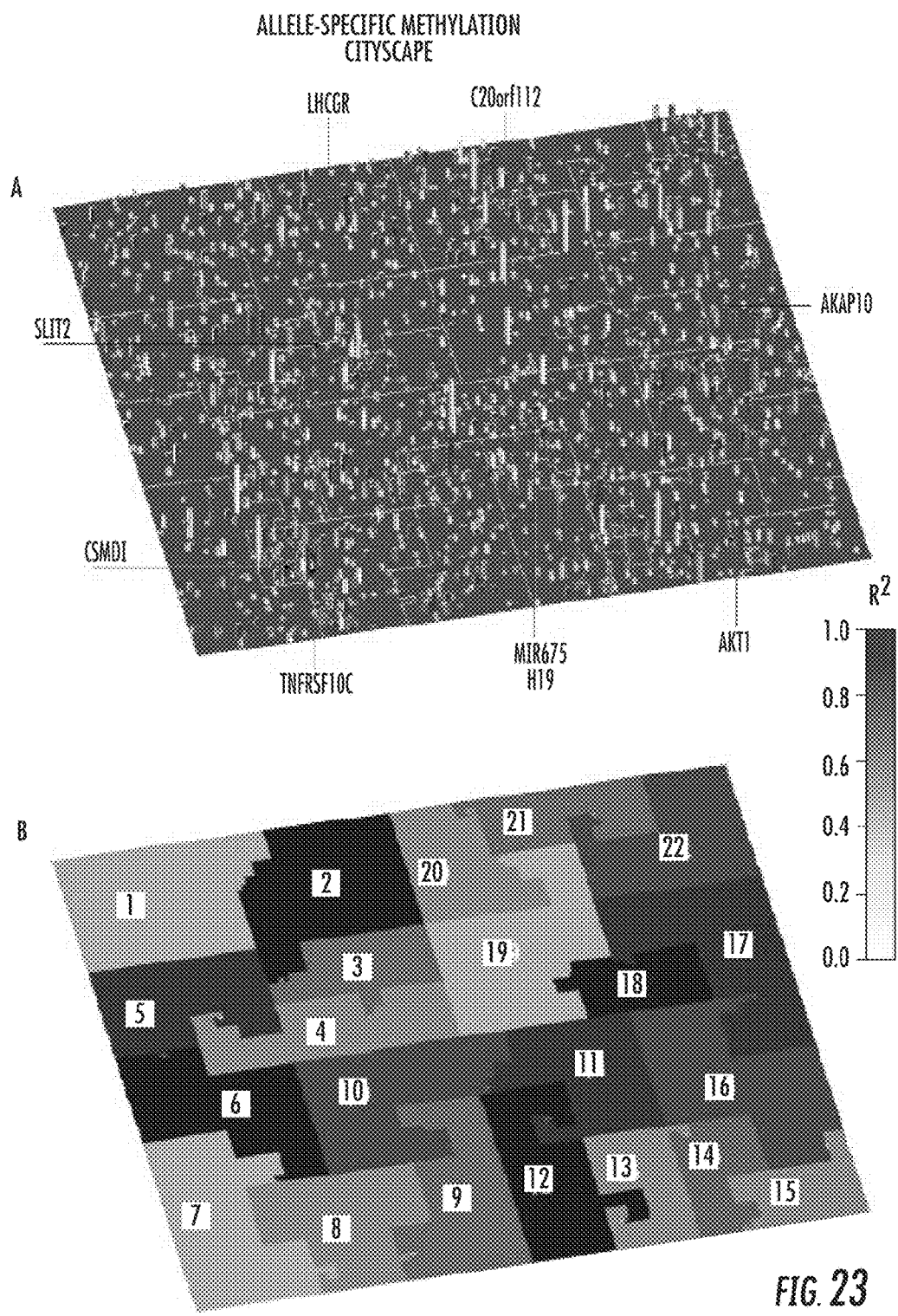
FIG. 23. Cityscape of gains and losses of A SM in lethal metastatic prostate cancer. The bar height represents the fraction of subjects showing an alteration. The bar color represents the R2 clonal maintenance metric. At each locus, analysis is restricted to those subjects with a heterozygous genotype.

The hypomethylation cityscape (FIG. 5B) differed from the hypermethylation cityscape in two major ways: (i) it contained many more structures, representing extensive regions of frequent hypomethylation, and (ii) it showed a much higher fraction of white and yellow structures, where intraindividual variation represented a much greater fraction of overall tumor heterogeneity. These findings are consistent with those from a recent report showing large blocks of highly variable hypomethylation in human cancers (41). Such widespread regions of hypomethylation may contribute to genomic instability by multiple mechanisms, including insertion of transposable elements (42). Finally, somatic ASM alterations were much less numerous than TM alterations and were significantly less consistently maintained compared to hypermethylation alterations (FIG. 23 and table S2).

Discussion

Given that epigenetic alterations can be labile, it has been questioned whether DNA methylation alterations can even be stable enough to be subject to selection during the clonal expansion events occurring during carcinogenesis, disease progression, and metastatic dissemination. With our study design of examining multiple metastases with a monoclonal origin within the same individual, we were able to examine distinct clonal expansion events within individuals (each metastasis) to assess the extent to which DNA methylation alterations were maintained across these metastases. We found that, overall, epigenetic alterations in DNA methylation were maintained to a similar extent as genetic alterations in copy number, suggesting that they have a similar potential as genetic alterations in serving as selectable driver events during clonal expansion/metastatic dissemination. This suggests that DNA methylation alterations could serve as a valuable source of targets for development of markers for cancer detection and prognosis and for development of new therapeutic strategies. However, this marked stability of DNA methylation alterations also implies that it will be important to distinguish between driver and passenger DNA methylation alterations, just as it has been important to do so for genetic alterations.

In this regard, our ability to survey different types of DNA methylation alterations, including DNA hypermethylation, DNA hypomethylation, and ASM, has provided several new insights. First, we found a general tendency for widespread but somewhat variable loss of methylation at normally methylated regions in metastases within individuals (see the large number of hypomethylation events in the hypomethylation cityscape in FIG. 5B). These hypomethylation events were not strongly correlated with any functional gene sets or with cis activation of gene expression. Therefore, if DNA hypomethylation played a driver role, it would likely be through promotion of genetic instability, for example, through promotion of retrotransposition (42), rather than through direct cis regulation of specific genes. In contrast, somatic acquisition of DNA hypermethylation at regions that were normally unmethylated (see hypermethylation cityscape) were less numerous but showed a greater tendency to stay methylated across all metastases. This staunch maintenance of newly acquired hypermethylation events in the metastases against the backdrop of a tendency to lose methylation at normally methylated regions in a widespread fashion across the genome suggests that most of the hypermethylation events were likely subject to specific selection across metastatic dissemination and expansion. This observation, combined with the strong correlation with cis regulation of gene expression and enrichment of hypermethylation at development/differentiation and cancer genes, suggests that DNA hypermethylation events may be highly enriched for driver epigenetic events.

Given the parallel evolution of DNA methylation and copy number alterations, it is possible that the DNA methylation alterations may be caused by genetic alterations in the cancers or vice versa. However, even in the former case, the DNA methylation alterations may still be part of the causal chain in cancer progression—for example, genetic alterations lead to epigenetic alterations, which are required for carcinogenesis or metastatic dissemination. Although this would need to be investigated in future functional studies, there is emerging evidence to implicate this chain of causation involving epigenetic alterations. For example, in the Apc Min mouse model (43), which typically develops dozens of intestinal polyps by 3 to 6 months of age, disruption of DNMT1 or MBD2, key mediators of DNA methylation-induced gene silencing, leads to pronounced reduction of polyp formation (44-46). Additionally, malignant transformation via activation of a variety of oncogenes often involves widespread epigenome alterations that have also been implicated in the causal chain (23, 47-49). Such somatic epigenetic alterations resulting from genetic mutations may be of particular interest because they may be more targetable/reversible through pharmacological manipulation than the upstream genetic alterations.

Our studies also reveal important insights on prostate tumor heterogeneity. There is a considerable amount of interindividual tumor heterogeneity at both the genetic (16, 26, 50, 51) and epigenetic levels. This interindividual heterogeneity challenges "one-size-fits-all" approaches for cancer management and highlights the need for individualized medicine approaches. Second, although the amount of intraindividual heterogeneity across metastases is considerably less than the interindividual variability for both genetic and epigenetic alterations, there is clonal evolution leading to appreciable intraindividual metastatic tumor heterogeneity in DNA methylation patterns. However, despite the strong relationship between heterogeneity in promoter methylation, particularly hypermethylation, and gene expression at the interindividual level, there was essentially no correlation between DNA methylation and gene expression at the intraindividual level. On the basis of these results, we can speculate that DNA methylation heterogeneity between different metastases within individuals arises in a largely stochastic manner, without much impact on cis regulation of gene expression phenotypes. It is therefore possible that lethal metastatic prostate cancer arises after passing through a very narrow but individual-specific clonal gate, with very little functional heterogeneity developing afterward. In a similar vein, a recent whole-genome analysis of primary and metastatic renal carcinoma showed that the degree of heterogeneity across different metastases within the same individual was much lower than the degree of heterogeneity across different portions of the primary tumor from the same individual (52). On an optimistic note, this marked intraindividual homogeneity across the lethal metastatic clonal gate, now observed at both the genetic (16) and epigenetic levels, may therefore represent a window of opportunity for effectively treating the lethal metastatic prostate cancer cell clone systemically. Studies such as the ones presented here could potentially focus target selection to the most promising genomic loci, exhibiting consistent somatic genome alterations across all metastases in affected individuals.

REFERENCES

1. D. Hanahan, R. A. Weinberg, Hallmarks of cancer: The next generation. Cell 144, 646-674 (2011).
2. P. A. Jones, S. B. Baylin, The epigenomics of cancer. Cell 128, 683-692 (2007).
3. B. Vogelstein, K. W. Kinzler, The Genetic Basis of Human Cancer (McGraw-Hill, Medical Pub. Division, New York, 2002).
4. A. V. Probst, E. Dunleavy, G. Almouzni, Epigenetic inheritance during the cell cycle. Nat. Rev. Mol. Cell Biol. 10, 192-206 (2009).
5. A. P. Feinberg, R. A. Irizarry, D. Fradin, M. J. Aryee, P. Murakami, T. Aspelund, G. Eiriksdottir, T. B. Harris, L. Launer, V. Gudnason, M. D. Fallin, Personalized epigenomic signatures that are stable over time and covary with body mass index. Sci. Transl. Med. 2, 49ra67 (2010).
6. M. Hemberger, W. Dean, W. Reik, Epigenetic dynamics of stem cells and cell lineage commitment: Digging Waddington's canal. Nat. Rev. Mol. Cell Biol. 10, 526-537 (2009).
7. S. Kangaspeska, B. Stride, R. Métivier, M. Polycarpou-Schwarz, D. Ibberson, R. P. Carmouche, V. Benes, F. Gannon, G. Reid, Transient cyclical methylation of promoter DNA. Nature 452, 112-115 (2008).
8. R. Métivier, R. Gallais, C. Tiffoche, C. Le Péron, R. Z. Jurkowska, R. P. Carmouche, D. Ibberson, P. Barath, F. Demay, G. Reid, V. Benes, A. Jeltsch, F. Gannon, G. Salbert, Cyclical DNA methylation of a transcriptionally active promoter. Nature 452, 45-50 (2008).
9. S. Rainier, A. P. Feinberg, Genomic imprinting, DNA methylation, and cancer. J. Natl. Cancer Inst. 86, 753-759 (1994).
10. E. Li, C. Beard, R. Jaenisch, Role for DNA methylation in genomic imprinting. Nature 366, 362-365 (1993).
11. B. Tycko, Allele-specific DNA methylation: Beyond imprinting. Hum. Mol. Genet. 19, R210-R220 (2010).
12. K. E. Schuebel, W. Chen, L. Cope, S. C. Glöckner, H. Suzuki, J. M. Yi, T. A. Chan, L. Van Neste, W. Van Criekinge, S. van den Bosch, M. van Engeland, A. H. Ting, K. Jair, W. Yu, M. Toyota, K. Imai, N. Ahuja, J. G. Herman, S. B. Baylin, Comparing the DNA hypermethylome with gene mutations in human colorectal cancer. PLoS Genet. 3, 1709-1723 (2007).
13. S. H. Cross, J. A. Charlton, X. Nan, A. P. Bird, Purification of CpG islands using a methylated DNA binding column. Nat. Genet. 6, 236-244 (1994).
14. S. Yegnasubramanian, X. Lin, M. C. Haffner, A. M. DeMarzo, W. G. Nelson, Combination of methylated-DNA precipitation and methylation-sensitive restriction enzymes (COMPARE-MS) for the rapid, sensitive and quantitative detection of DNA methylation. Nucleic Acids Res. 34, e19 (2006).
15. S. Yegnasubramanian, Z. Wu, M. C. Haffner, D. Esopi, M. J. Aryee, R. Badrinath, T. L. He, J. D. Morgan, B. Carvalho, Q. Zheng, A. M. De Marzo, R. A. Irizarry, W. G. Nelson, Chromosomewide mapping of DNA methylation patterns in normal and malignant prostate cells reveals pervasive methylation of gene-associated and conserved intergenic sequences. BMC Genomics 12, 313 (2011).

16. W. Liu, S. Laitinen, S. Khan, M. Vihinen, J. Kowalski, G. Yu, L. Chen, C. M. Ewing, M. A. Eisenberger, M. A. Carducci, W. G. Nelson, S. Yegnasubramanian, J. Luo, Y. Wang, J. Xu, W. B. Isaacs, T. Visakorpi, G. S. Bova, Copy number analysis indicates monoclonal origin of lethal metastatic prostate cancer. Nat. Med. 15, 559-565 (2009).

17. S. Yachida, S. Jones, I. Bozic, T. Antal, R. Leary, B. Fu, M. Kamiyama, R. H. Hruban, J. R. Eshleman, M. A. Nowak, V. E. Velculescu, K. W. Kinzler, B. Vogelstein, C. A. Iacobuzio-Donahue, Distant metastasis occurs late during the genetic evolution of pancreatic cancer. Nature 467, 1114-1117 (2010).

18. P. J. Campbell, S. Yachida, L. J. Mudie, P. J. Stephens, E. D. Pleasance, L. A. Stebbings, L. A. Morsberger, C. Latimer, S. McLaren, M. L. Lin, D. J. McBride, I. Varela, S. A. Nik-Zainal, C. Leroy, M. Jia, A. Menzies, A. P. Butler, J. W. Teague, C. A. Griffin, J. Burton, H. Swerdlow, M. A. Quail, M. R. Stratton, C. Iacobuzio-Donahue, P. A. Futreal, The patterns and dynamics of genomic instability in metastatic pancreatic cancer. Nature 467, 1109-1113 (2010).

19. S. Yegnasubramanian, J. Kowalski, M. L. Gonzalgo, M. Zahurak, S. Piantadosi, P. C. Walsh, G. S. Bova, A. M. De Marzo, W. B. Isaacs, W. G. Nelson, Hypermethylation of CpG islands in primary and metastatic human prostate cancer. Cancer Res. 64, 1975-1986 (2004).

20. A. P. Feinberg, R. Ohlsson, S. Henikoff, The epigenetic progenitor origin of human cancer. Nat. Rev. Genet. 7, 21-33 (2006).

21. D. F. Jarrard, M. J. Bussemakers, G. S. Bova, W. B. Isaacs, Regional loss of imprinting of the insulin-like growth factor II gene occurs in human prostate tissues. Clin. Cancer Res. 1, 1471-1478 (1995).

22. J. P. Issa, CpG island methylator phenotype in cancer. Nat. Rev. Cancer 4, 988-993 (2004).

23. D. J. Weisenberger, K. D. Siegmund, M. Campan, J. Young, T. I. Long, M. A. Faasse, G. H. Kang, M. Widschwendter, D. Weener, D. Buchanan, H. Koh, L. Simms, M. Barker, B. Leggett, J. Levine, M. Kim, A. J. French, S. N. Thibodeau, J. Jass, R. Haile, P. W. Laird, CpG islandmethylator phenotype underlies sporadic microsatellite instability and is tightly associated with BRAF mutation in colorectal cancer. Nat. Genet. 38, 787-793 (2006).

24. H. Noushmehr, D. J. Weisenberger, K. Diefes, H. S. Phillips, K. Pujara, B. P. Berman, F. Pan, C. E. Pelloski, E. P. Sulman, K. P. Bhat, R. G. Verhaak, K. A. Hoadley, D. N. Hayes, C. M. Perou, H. K. Schmidt, L. Ding, R. K. Wilson, D. Van Den Berg, H. Shen, H. Bengtsson, P. Neuvial, L. M. Cope, J. Buckley, J. G. Herman, S. B. Baylin, P. W. Laird, K. Aldape; Cancer Genome Atlas Research Network, Identification of a CpG island methylator phenotype that defines a distinct subgroup of glioma. Cancer Cell 17, 510-522 (2010).

25. M. Ashburner, C. A. Ball, J. A. Blake, D. Botstein, H. Butler, J. M. Cherry, A. P. Davis, K. Dolinski, S. S. Dwight, J. T. Eppig, M. A. Harris, D. P. Hill, L. Issel-Tarver, A. Kasarskis, S. Lewis, J. C. Matese, J. E. Richardson, M. Ringwald, G. M. Rubin, G. Sherlock, Gene ontology: Tool for the unification of biology. The Gene Ontology Consortium. Nat. Genet. 25, 25-29 (2000).

26. B. S. Taylor, N. Schultz, H. Hieronymus, A. Gopalan, Y. Xiao, B. S. Carver, V. K. Arora, P. Kaushik, E. Cerami, B. Reva, Y. Antipin, N. Mitsiades, T. Landers, I. Dolgalev, J. E. Major, M. Wilson, N. D. Socci, A. E. Lash, A. Heguy, J. A. Eastham, H. I. Scher, V. E. Reuter, P. T. Scardino, C. Sander, C. L. Sawyers, W. L. Gerald, Integrative genomic profiling of human prostate cancer. Cancer Cell 18, 11-22 (2010).

27. National Cancer Institute, NCI Cancer Gene Index (2009)

28. S. Yegnasubramanian, M. C. Haffner, Y. Zhang, B. Gurel, T. C. Cornish, Z. Wu, R. A. Irizarry, J. Morgan, J. Hicks, T. L. DeWeese, W. B. Isaacs, G. S. Bova, A. M. De Marzo, W. G. Nelson, DNA hypomethylation arises later in prostate cancer progression than CpG island hypermethylation and contributes to metastatic tumor heterogeneity. Cancer Res. 68, 8954-8967 (2008).

29. M. Esteller, Epigenetics in cancer. N. Engl. J. Med. 358, 1148-1159 (2008).

30. J. G. Herman, S. B. Baylin, Gene silencing in cancer in association with promoter hypermethylation. N. Engl. J. Med. 349, 2042-2054 (2003).

31. A. P. Feinberg, B. Vogelstein, Hypomethylation distinguishes genes of some human cancers from their normal counterparts. Nature 301, 89-92 (1983).

32. S. E. Goelz, B. Vogelstein, S. R. Hamilton, A. P. Feinberg, Hypomethylation of DNA from benign and malignant human colon neoplasms. Science 228, 187-190 (1985).

33. M. A. Gama-Sosa, V. A. Slagel, R. W. Trewyn, R. Oxenhandler, K. C. Kuo, C. W. Gehrke, M. Ehrlich, The 5-methylcytosine content of DNA from human tumors. Nucleic Acids Res. 11, 6883-6894 (1983).

34. J. Luo, S. Zha, W. R. Gage, T. A. Dunn, J. L. Hicks, C. J. Bennett, C. M. Ewing, E. A. Platz, S. Ferdinandusse, R. J. Wanders, J. M. Trent, W. B. Isaacs, A. M. De Marzo, a-Methylacyl-CoA racemase: A new molecular marker for prostate cancer. Cancer Res. 62, 2220-2226 (2002).

35. J. Luo, D. J. Duggan, Y. Chen, J. Sauvageot, C. M. Ewing, M. L. Bittner, J. M. Trent, W. B. Isaacs, Human prostate cancer and benign prostatic hyperplasia: Molecular dissection by gene expression profiling. Cancer Res. 61, 4683-4688 (2001).

36. S. Varambally, S. M. Dhanasekaran, M. Zhou, T. R. Barrette, C. Kumar-Sinha, M. G. Sanda, D. Ghosh, K. J. Pienta, R. G. Sewalt, A. P. Otte, M. A. Rubin, A. M. Chinnaiyan, The polycomb group protein EZH2 is involved in progression of prostate cancer. Nature 419, 624-629 (2002).

37. W. H. Lee, R. A. Morton, J. I. Epstein, J. D. Brooks, P. A. Campbell, G. S. Bova, W. S. Hsieh, W. B. Isaacs, W. G. Nelson, Cytidine methylation of regulatory sequences near the p-class glutathione S-transferase gene accompanies human prostatic carcinogenesis. Proc. Natl. Acad. Sci. U.S.A. 91, 11733-11737 (1994).

38. S. A. Bert, M. D. Robinson, D. Strbenac, A. L. Statham, J. Z. Song, T. Hulf, R. L. Sutherland, M. W. Coolen, C. Stirzaker, S. J. Clark, Regional activation of the cancer genome by long-range epigenetic remodeling. Cancer Cell 10.1016/j.ccr.2012.11.006 (2012).

39. S. Anders, Visualization of genomic data with the Hilbert curve. Bioinformatics 25, 1231-1235 (2009).

40. M. W. Coolen, C. Stirzaker, J. Z. Song, A. L. Statham, Z. Kassir, C. S. Moreno, A. N. Young, V. Varma, T. P. Speed, M. Cowley, P. Lacaze, W. Kaplan, M. D. Robinson, S. J. Clark, Consolidation of the cancer genome into domains of repressive chromatin by longrange epigenetic silencing (LRES) reduces transcriptional plasticity. Nat. Cell Biol. 12, 235-246 (2010).

41. K. D. Hansen, W. Timp, H. C. Bravo, S. Sabunciyan, B. Langmead, O. G. McDonald, B. Wen, H. Wu, Y. Liu, D. Diep, E. Briem, K. Zhang, R. A. Irizarry, A. P. Feinberg, Increased methylation variation in epigenetic domains across cancer types. Nat. Genet. 43, 768-775 (2011).

42. E. Lee, R. Iskow, L. Yang, O. Gokcumen, P. Haseley, L. J. Luquette III, J. G. Lohr, C. C. Harris, L. Ding, R. K. Wilson, D. A. Wheeler, R. A. Gibbs, R. Kucherlapati, C. Lee, P. V. Kharchenko, P. J. Park; Cancer Genome Atlas Research Network, Landscape of somatic retrotransposition in human cancers. Science 337, 967-971 (2012).

43. L. K. Su, K. W. Kinzler, B. Vogelstein, A. C. Preisinger, A. R. Moser, C. Luongo, K. A. Gould, W. F. Dove, Multiple intestinal neoplasia caused by a mutation in the murine homolog of the APC gene. Science 256, 668-670 (1992).

44. P. W. Laird, L. Jackson-Grusby, A. Fazeli, S. L. Dickinson, W. E. Jung, E. Li, R. A. Weinberg, R. Jaenisch, Suppression of intestinal neoplasia by DNA hypomethylation. Cell 81, 197-205 (1995).

45. C. A. Eads, A. E. Nickel, P. W. Laird, Complete genetic suppression of polyp formation and reduction of CpG-island hypermethylation in ApcMin/+Dnmt1-hypomorphic mice. Cancer Res. 62, 1296-1299 (2002).

46. O. J. Sansom, J. Berger, S. M. Bishop, B. Hendrich, A. Bird, A. R. Clarke, Deficiency of Mbd2 suppresses intestinal tumorigenesis. Nat. Genet. 34, 145-147 (2003).

47. A. V. Bakin, T. Curran, Role of DNA 5-methylcytosine transferase in cell transformation by fos. Science 283, 387-390 (1999).

48. J. Peli, M. Schröter, C. Rudaz, M. Hahne, C. Meyer, E. Reichmann, J. Tschopp, Oncogenic Ras inhibits Fas ligand-mediated apoptosis by downregulating the expression of Fas. EMBO J. 18, 1824-1831 (1999).

49. C. Gazin, N. Wajapeyee, S. Gobeil, C. M. Virbasius, M. R. Green, An elaborate pathway required for Ras-mediated epigenetic silencing. Nature 449, 1073-1077 (2007).

50. M. F. Berger, M. S. Lawrence, F. Demichelis, Y. Drier, K. Cibulskis, A. Y. Sivachenko, A. Sboner, R. Esgueva, D. Pflueger, C. Sougnez, R. Onofrio, S. L. Carter, K. Park, L. Habegger, L. Ambrogio, T. Fennell, M. Parkin, G. Saksena, D. Voet, A. H. Ramos, T. J. Pugh, J. Wilkinson, S. Fisher, W. Winckler, S. Mahan, K. Ardlie, J. Baldwin, J. W. Simons, N. Kitabayashi, T. Y. MacDonald, P. W. Kantoff, L. Chin, S. B. Gabriel, M. B. Gerstein, T. R. Golub, M. Meyerson, A. Tewari, E. S. Lander, G. Getz, M. A. Rubin, L. A. Garraway, The genomic complexity of primary human prostate cancer. Nature 470, 214-220 (2011).

51. M. A. Rubin, C. A. Maher, A. M. Chinnaiyan, Common gene rearrangements in prostate cancer. J. Clin. Oncol. 29, 3659-3668 (2011).

52. M. Gerlinger, A. J. Rowan, S. Horswell, J. Larkin, D. Endesfelder, E. Gronroos, P. Martinez, N. Matthews, A. Stewart, P. Tarpey, I. Varela, B. Phillimore, S. Begum, N. Q. McDonald, A. Butler, D. Jones, K. Raine, C. Latimer, C. R. Santos, M. Nohadani, A. C. Eklund, B. Spencer-Dene, G. Clark, L. Pickering, G. Stamp, M. Gore, Z. Szallasi, J. Downward, P. A. Futreal, C. Swanton, Intratumor heterogeneity and branched evolution revealed by multiregion sequencing. N. Engl. J. Med. 366, 883-892 (2012).

53. D. Serre, B. H. Lee, A. H. Ting, MBD-isolated genome sequencing provides a highthroughput and comprehensive survey of DNA methylation in the human genome. Nucleic Acids Res. 38, 391-399 (2010).

54. K. Prakash, G. Pirozzi, M. Elashoff, W. Munger, I. Waga, R. Dhir, Y. Kakehi, R. H. Getzenberg, Symptomatic and asymptomatic benign prostatic hyperplasia: Molecular differentiation by using microarrays. Proc. Natl. Acad. Sci. U.S.A. 99, 7598-7603 (2002).

55. T. A. Dunn, S. Chen, D. A. Faith, J. L. Hicks, E. A. Platz, Y. Chen, C. M. Ewing, J. Sauvageot, W. B. Isaacs, A. M. DeMarzo, J. Luo, A novel role of myosin VI in human prostate cancer. Am. J. Pathol. 169, 1843-1854 (2006).

56. R Development Core Team, R: A Language and Environment for Statistical Computing (R Foundation for Statistical Computing, Vienna, Austria, 2011).

57. R. C. Gentleman, V. J. Carey, D. M. Bates, B. Bolstad, M. Dettling, S. Dudoit, B. Ellis, L. Gautier, Y. Ge, J. Gentry, K. Hornik, T. Hothorn, W. Huber, S. Iacus, R. Irizarry, F. Leisch, C. Li, M. Maechler, A. J. Rossini, G. Sawitzki, C. Smith, G. Smyth, L. Tierney, J. Y. Yang, J. Zhang, Bioconductor: Open software development for computational biology and bioinformatics. Genome Biol. 5, R80 (2004).

58. Y. Kobayashi, D. M. Absher, Z. G. Gulzar, S. R. Young, J. K. McKenney, D. M. Peehl, J. D. Brooks, R. M. Myers, G. Sherlock, DNA methylation profiling reveals novel biomarkers and important roles for DNA methyltransferases in prostate cancer. Genome Res. 21, 1017-1027 (2011).

We claim:

1. A method comprising the step of measuring in genomic DNA obtained from a prostate tissue sample of an individual the methylation level of the promoter region of each gene in a panel of genes consisting of APC, GSTP1, POU4F1, OLIG2, EYA4, ADAMTS12, PTGS2, SLC26A4, SSTR1, FOXE1, UGT3A1, RASGRF2, and SSPN.

* * * * *